United States Patent [19]
Neville et al.

[11] Patent Number: 6,103,235
[45] Date of Patent: Aug. 15, 2000

[54] METHODS OF INDUCING IMMUNE TOLERANCE USING IMMUNOTOXINS

[75] Inventors: David M. Neville, Bethesda, Md.; Stuart Knechtle, Oregon, Wis.

[73] Assignees: The United States of America as represented by the Department of Health and Human Services, Washington, D.C.; The UAB Research Foundation, Birmingham, Ala.

[21] Appl. No.: 08/843,409

[22] Filed: Apr. 15, 1997

Related U.S. Application Data

[63] Continuation-in-part of application No. 08/739,703, Oct. 29, 1996.
[60] Provisional application No. 60/015,459, Apr. 15, 1996, abandoned, and provisional application No. 60/008,104, Oct. 30, 1995, abandoned.

[51] Int. Cl.⁷ .......................... A61K 39/395; A61K 39/00
[52] U.S. Cl. ...................................... 424/183.1; 424/184.1
[58] Field of Search .............................. 424/183.1, 173.1, 424/184.1

[56] References Cited

U.S. PATENT DOCUMENTS 5,167,956 12/1992 Neville, Jr. ............................. 424/85.1

OTHER PUBLICATIONS

Ma, et al. Expression and Characterization of a Divalent Chimeric Anti–Human CD3 Single Chain Antibody *Scand. J. Immunol.* 43, 134–139, 1996.
Lu et al (J. Am. Soc. Neprol., 4:1239–1256, 1993.
Nemoto et al (Agents Actions, 36:306–311, 1992.
Koehler et al (Bone Marrow Transplantation, 13:571–575, 1994.
Neville et al. *J. Immunotherapy* 19(2):85–92, 1996.
Thompson et al. *J. Biol. Chem.* 270(47):28037–28041, Nov. 24, 1995.
Neville et al. *J. Controlled Release* 24(1–3):133–144, May 1993.
Neville et al. *Proc. Natl. Acad. Sci. USA* 89:2585–2589, 1992.
Pastan et al. *Science* 254:1173–1177, Nov. 22, 1991.
Parlevliet et al. *Transplantation* 50:889–892, Nov., 1990.
Kappler et al. *Science* 244:811–813, May 19, 1989.
Greenfield et al. Science 238:536–539, 1987.
Nooij and Jonker *Eur. J. Immunol.* 17:1089–1093, 1987.
Thomas et al. *Transplantation* (1994) 57:101–115.
Thomas et al. *Transplantation Proceedings* (1995) 27:3167.
Traunecker, et al. Bispecific single chain molecules (Janusins) target cytotoxic lymphocytes on HIV infected cells. *The EMBO Journal* (1)12:3655–3659 (1991).
Hayden et al. Single–chain mono–and bispecific antibody derivatives with novel biological properties and antitumor activity from a COS cell transient expression system. *Therapeutic Immunology*(1):3–15 (1994).

*Primary Examiner*—Paula K. Hutzell
*Assistant Examiner*—Susan Ungar
*Attorney, Agent, or Firm*—Needle & Rosenberg, P.C.

[57] ABSTRACT

Provided is a method of treating an immune system disorder not involving T cell proliferation, comprising administering to the animal an immunotoxin comprising a mutant diphtheria toxin moiety linked to an antibody moiety which routes by the anti-CD3 pathway, or derivatives thereof under conditions such that the disorder is treated. Thus, the present method can treat graft-versus-host disease. Also provided is a method of inhibiting a rejection response by inducing immune tolerance in a recipient to a foreign mammalian donor tissue or cells, comprising the steps of: a) exposing the recipient to an immunotoxin so as to reduce the recipients's peripheral blood T-cell lymphocyte population by at least 80%, wherein the immunotoxin is anti-CD3 antibody linked to a diphtheria protein toxin, wherein the protein has a binding site mutation; and b) transplanting the donor cells into the recipient, whereby a rejection response by the recipient to the donor organ cell is inhibited, and the host is tolerized to the donor cell.

8 Claims, 22 Drawing Sheets

SEQUENCE LISTING

<160> NUMBER OF SEQ ID NOS: 14

<210> SEQ ID NO 1
<211> LENGTH: 67
<212> TYPE: DNA
<213> ORGANISM: Artificial Sequence
<220> FEATURE:
<223> OTHER INFORMATION: leader sequence

<400> SEQUENCE: 1
atgaaatacc tattgcctac ggcagccgct ggattgttat tactcgctg cccaaccagc    60
gatggcc                                                             67

<210> SEQ ID NO 2
<211> LENGTH: 54
<212> TYPE: DNA
<213> ORGANISM: Artificial Sequence
<220> FEATURE:
<223> OTHER INFORMATION: oligonucleotide primer

<400> SEQUENCE: 2
atgaaatacc tattgcctac ggcagccgct ggattgttat tactcgctgc ccaa          54

<210> SEQ ID NO 3
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 3
ggattgttat tactcgctgc ccaacaagcg atggccggcg ctgatgatgt tgttgattc     59

<210> SEQ ID NO 4
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 4
cggtactata aaactctttc caatcatcgt c                                   31

<210> SEQ ID NO 5
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 5
gacgatgatt ggaaagagtt ttatagtacc g                                   31

<210> SEQ ID NO 6
<211> LENGTH: 40
<212> TYPE: DNA
<213> ORGANISM: Artificial Sequence
<220> FEATURE:
<223> OTHER INFORMATION: oligonucleotide primer
<223> OTHER INFORMATION: m is a or c

<400> SEQUENCE: 6
agatctgtcg mtcatcagct tttgatttca aaaatagcg                           40

```
<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 7
gacatccaga tgacccagac c                                      21

<210> SEQ ID NO 8
<211> LENGTH: 56
<212> TYPE: DNA
<213> ORGANISM: Artificial Sequence
<220> FEATURE:
<223> OTHER INFORMATION: oligonucleotide primer
<223> OTHER INFORMATION: k is g or t
<223> OTHER INFORMATION: s is c or g

<400> SEQUENCE: 8
cctcccgagc caccgcctcc gctgcctccg cctccttta tctccagctt kgtscc   56

<210> SEQ ID NO 9
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 9
gcagcggagg cggtggctcg ggaggggag gctcggaggt gcagcttcag cagtct   56

<210> SEQ ID NO 10
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 10
gcaagcttga agactgtgag agtggtgcct tg                           32

<210> SEQ ID NO 11
<211> LENGTH: 36
<212> TYPE: DNA
<213> ORGANISM: Artificial Sequence
<220> FEATURE:
<223> OTHER INFORMATION: oligonucleotide primer
<223> OTHER INFORMATION: y is c or t

<400> SEQUENCE: 11
gtctcttcaa agcttattgc ygagctgcct cccaaa                       36

<210> SEQ ID NO 12
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 12
gcatctagat cagtagcagg tgccagctgt gt                           32

<210> SEQ ID NO 13
<211> LENGTH: 59
<212> TYPE: DNA
<213> ORGANISM: Artificial Sequence
```

-continued

```
<220> FEATURE:
<223> OTHER INFORMATION: oligonucleotide primer

<400> SEQUENCE: 13
cggtcgacac catggagaca gacacactcc tgttatgggt actgctgctc tgggttcca        59

<210> SEQ ID NO 14
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 14
gtactgctgc tctgggttcc aggttccact ggggacatcc agatgaccca g                51
```

METHODS OF INDUCING IMMUNE TOLERANCE USING IMMUNOTOXINS

This application for letters patent claims priority under 35 U.S.C. § 119(e) of provisional patent application serial number 60/015,459, filed on Apr. 15, 1996, now abandoned, having the same title of invention and the same inventors as the present application and claims priority to provisional patent application number 60/008,104, filed on Oct. 30, 1995, now abandoned. This application also claims priority to and is a continuation in part of U.S. Ser. No. 08/739,703, filed Oct. 29, 1996.

BACKGROUND OF THE INVENTION

1. Field of The Invention

This invention generally relates to an immunotoxin and to techniques for inducing immunological tolerance in primates. It appears to be especially well suited to provide a method for inhibiting rejection of transplanted organs. The invention further relates to a method of treating T cell leukemias or lymphomas, graft-versus-host diseases, and autoimmune diseases by administering an immunotoxin.

2. Background Art

The number of organ transplants performed in the United States is approximately 19,000 annually and consists predominantly of kidney transplants (11,000), liver transplants (3,600), heart transplants (2,300), and smaller numbers of pancreas, lung, heart-lung, and intestinal transplants. Since 1989 when the United Network for Organ Sharing began keeping national statistics, approximately 190,000 organ transplants have been performed in the United States. A large but difficult to ascertain number of transplants were performed in the United States prior to 1989 and a similarly large number of transplants are performed in Europe and Australia and a smaller number in Asia.

Transplant tolerance remains an elusive goal for patients and physicians whose ideal would be to see a successful, allogeneic organ transplant performed without the need for indefinite, non-specific maintenance immunosuppressive drugs and their attendant side effects. Over the past 10 years the majority of these patients have been treated with cyclosporin, azathioprine, and prednisone with a variety of other immunosuppressive agents being used as well for either induction or maintenance immunosuppression. The average annual cost of maintenance immunosuppressive therapy in the United States is approximately $10,000. While the efficacy of these agents in preventing rejection is good, the side effects of immunosuppressive therapy are considerable because the unresponsiveness which they induce is nonspecific. For example, recipients can become very susceptible to infection. A major goal in transplant immunobiology is the development of specific immunologic tolerance to organ transplants with the potential of freeing patients from the side effects of continuous pharmacologic immunosuppression and its attendant complications and costs.

Anti-T cell therapy (anti-lymphocyte globulin) has been used in rodents in conjunction with thymic injection of donor cells (Posselt et al. *Science* 1990; 249: 1293–1295 and Remuzzi et al. *Lancet* 1991; 337: 750–752). Thymic tolerance has proved successful in rodent models and involves the exposure of the recipient thymus gland to donor alloantigen prior to an organ allograft from the same donor. However, thymic tolerance has never been demonstrated in large animals, and its relevance to tolerance in humans in unknown.

One approach to try to achieve such immunosuppression has been to expose the recipient to cells from the donor prior to the transplant, with the hope of inducing tolerance to a later transplant. This approach has involved placement of donor cells (e.g. bone marrow) presenting MHC Class I antigens in the recipient's thymus shortly after application of anti-lymphocyte serum (ALS) or radiation. However, this approach has proved difficult to adapt to live primates (e.g. monkeys; humans). ALS and/or radiation render the host susceptible to disease or side-effects and/or are insufficiently effective.

If a reliable, safe approach to specific immunologic tolerance could be developed, this would be of tremendous value and appeal to patients and transplant physicians throughout the world with immediate application to new organ transplants and with potential application to transplant recipients with stable function. Thus, a highly specific immunosuppression is desired. Furthermore, there is a need for a means for imparting tolerance in primates, without the adverse attributes of using ALS or radiation. Moreover, the goal is to achieve more than simply delaying the rejection response. Rather, an important goal is to inhibit the rejection response to the point that rejection is not a factor in reducing average life span.

The present invention meets this need by providing a method of inducing immune tolerance.

SUMMARY OF THE INVENTION

It is an object of this invention to provide an immunotoxin for treating immune system disorders.

It is a further object of the invention to provide a method of treating an immune system disorder not involving T cell proliferation, comprising administering to the animal an immunotoxin comprising a mutant diphtheria toxin moiety linked to an antibody moiety which routes by the anti-CD3 pathway, or derivatives thereof under conditions such that the disorder is treated. Thus, the present method can treat graft-versus-host disease.

It is a further object of the invention to provide a method of inducing immune tolerance. Thus, the invention provides a method of inhibiting a rejection response by inducing immune tolerance in a recipient to a foreign mammalian donor tissue or cells, comprising the steps of: a) exposing the recipient to an immunotoxin so as to reduce the recipients's peripheral blood T-cell lymphocyte population by at least 80%, wherein the immunotoxin is anti-CD3 antibody linked to a diphtheria protein toxin, wherein the protein has a binding site mutation; and b) transplanting the donor cells into the recipient, whereby a rejection response by the recipient to the donor organ cell is inhibited, and the host is tolerized to the donor cell.

The objects of the invention therefore include providing methods of the above kind for inducing tolerance to transplanted organs or cells from those organs. This and still other objects and advantages of the present invention will be apparent from the description which follows.

BRIEF DESCRIPTION OF THE DRAWINGS

FIG. 1 shows nude mice bg/nu/xid maintained in a semi-sterile environment are preconditioned with 400 cGy whole body $^{137}$CS γ radiation on day −7. On day 0, $2.5\times10^{7}$ Jurkat cells (human T cell leukemia CD3+, CD4+, CD5+) are injected subcutaneously with $1\times10^{7}$ HT-1080 feeder cells (human sarcoma) which have received 6000 cGy. Jurkat cells were passaged every other week in mice as subcutaneous tumors and dissociated by collagenase/dispase prior to inoculation. This cell population exhibits a 40% inhibition of protein synthesis after 5 hours exposure to $10^{11}$M anti-CD3-DT. Clones isolated from this population by infinite dilution exhibit varying sensitivity to anti-CD3-DT (4 less sensitive, 3 more sensitive) corresponding to a 1.5 log variation in dose response curves. Immunotoxin treatment is given by intraperitoneal injection starting on day 7 when the tumor is visibly established. Evaluation takes place on day 37.

FIG. 2 shows that the epitopes involved in human serum's inhibition of toxicity lie in the last 150 amino acids of DT. A schematic diagram of the DT mutants CRM9, CRM197 and MSPΔ5 is presented (A). The A- and B-subfragments and their relative size and position are shown. The filled circle represents a point mutation as described in the text. Goat (B) or human (C) serum (human serum was a pool from all samples with positive ELISA for anti-DT antibodies) was incubated with increasing molar concentrations of CRM197 (-O-), MSPΔ5 (-X-) or the B-subfragment (-Δ-) of DT for 30 minutes at room temperature. To this reaction, UCHT1-CRM9 was added to a final concentration of $1 \times 10^{-10}$ M. This mixture was then diluted 10-fold onto Jurkat cells in a protein synthesis inhibition assay as described in the Materials and Methods. Immunotoxin incubated with medium only inhibited protein synthesis to 4% of controls. The results are representative of two independent assays.

FIG. 3 shows that sFv-DT390 maintains specificity for the CD3 complex but is 16-fold less toxic than UCHT1-CRM9 to Jurkat cells. A) Increasing concentrations of sFv-DT390 (-Δ-) or UCHT1-CRM9 (-O-) were tested in protein synthesis inhibition assays as described in the Materials and Methods. The results are an average of four separate experiments. B) Increasing concentrations of UCHT1 antibody were mixed with a $1 \times 10^{-10}$ M UCHT1-CRM9 (-O-) or $3.3 \times 10^{-10}$ M sFv-DT390 (-Δ-) and then added to cells for a protein synthesis inhibition assay.

FIG. 4 shows the schematic flow sheet for generation of the single chain antibody scUCHT1 gene construct. PCR: polymerase chain reaction; L: linker; SP: signal peptide. P1 to P6, SP1, and SP2 are primers used in PCR, and listed in table 1.

FIG. 5 shows the western blotting analysis of the single chain antibody scUCHT1. scUCHT1 was immunoprecipitated, and separated on 4–20% SDS/PAGE gradient gel. After transferring to Problott™ membrane, scUCHT1 was visualized by an anti-human IgM antibody labeled with phosphatase. scUCHT1 secreted was mainly a dimeric form. Lane 1–3 representing electrophoresis under reducing conditions, and 4–6 non-reducing conditions. Lane 1 and 6 are human IgM; lane 1: IgM heavy chain. The light chain is not visible, because the anti-IgM antibody is directed at the heavy chain; lane 6: IgM pentamer is shown as indicated by the arrow. Lane 2 and 4 scUCHT1 from COS-7 cells; 3 and 5 scUCHT1 from SP2/0 cells.

FIG. 6 shows that scUCHT1 had the same specificity and affinity as its parental antibody UCHT1. In the competition assay, $^{125}$I-UCHT1 was used as tracer in binding Jurkat cells. scUCHT1 from COS-7 (□) and SP2/0 cells (Δ),or unlabeled UCHT1 (o) with indicated concentrations were included as competitor. Results were expressed as a percentage of the $^{125}$I-UCHT1 bound to cells in the absence of competitors.

FIG. 7 shows that scUCHT1 did not induce human T cell proliferation response. scUCHT1 from COS-7 (Δ) and SP2/0 (o) cells and UCHT1 (□) were added to human PBMCs at indicated concentrations and T cell proliferation was assayed by [3H]thymidine incorporation. UCHT1 induced a vigorous proliferation response. On the contrary, scUCHT1 had little effect at any doses.

DETAILED DESCRIPTION OF THE INVENTION

Figure 1:
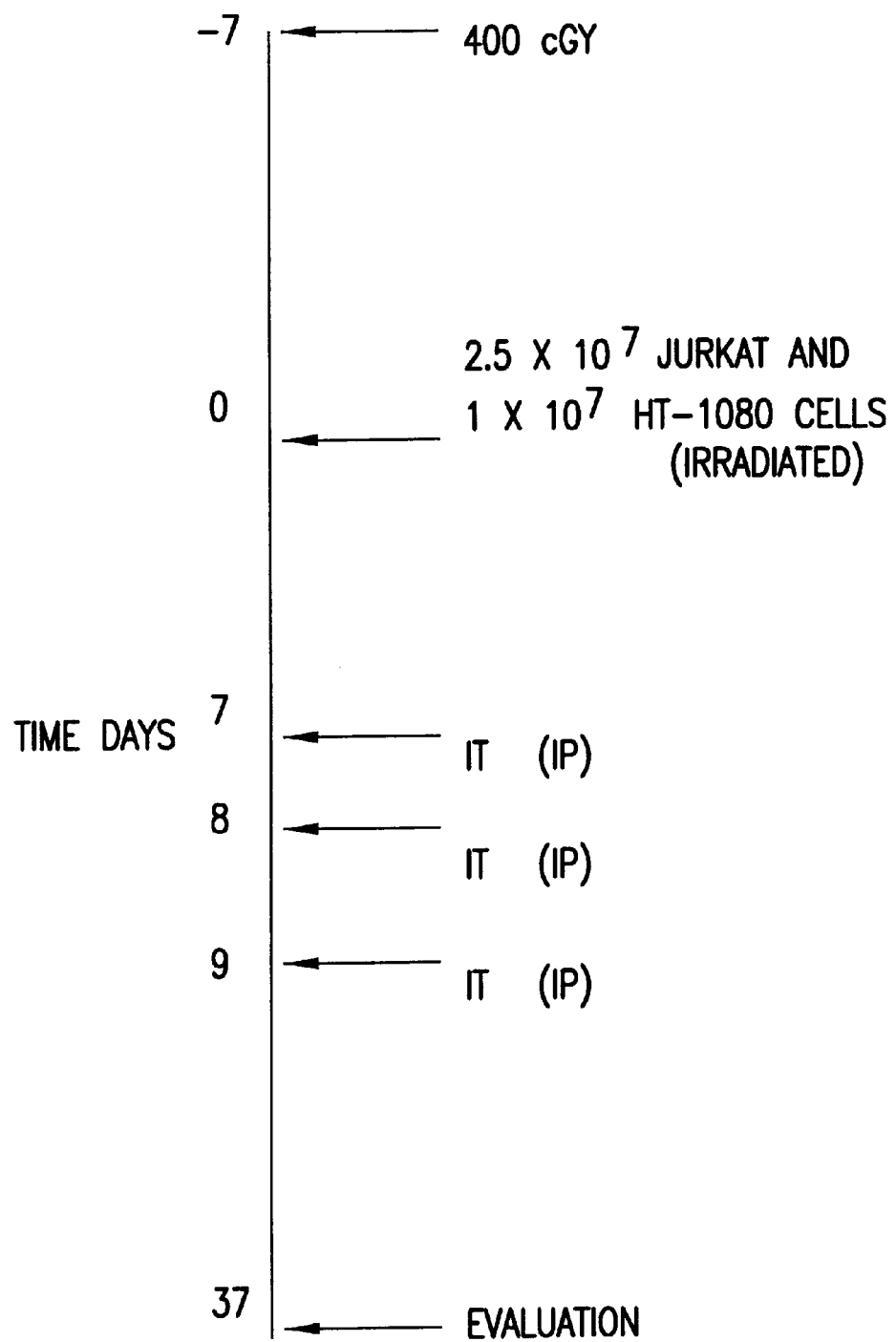

The invention provides immunotoxins and methods of using them to induce immune tolerance and to treat disease. Immunotoxin.

The present invention relates to an immunotoxin. More specifically, an immunotoxin, comprising a mutant diphtheria toxin moiety linked to a single chain variable region antibody which routes by the anti-CD3 pathway is provided. The immunotoxin can be divalent. The immunotoxin can be a fusion protein produced recombinantly. The antibody moiety of the immunotoxin can comprise the human CH2 and CH3 regions. These regions can be from the antibody UCHT1 so that the antibody moiety is scUCHT1, which is a single chain CD3 antibody having human CH2 and CH3 regions and mouse variable regions as shown in the figures. These are the first instances of a sc anti-CD3 antibodies. Numerous DT mutant toxin moieties are described herein, for example DT390. Thus, as just one specific example the immunotoxin, the invention provides scUCHT1-DT390. Derivatives of this immunotoxin are designed and constructed as described herein.

The toxin moiety retains its toxic function, and. membrane translocation function to the cytosol in full amounts. The loss in binding function located in the C terminus of the protein diminishes systemic toxicity by, reducing binding to non-target cells. Thus, the immunotoxin can be safely administered. The routing function normally supplied by the toxin binding function is supplied by the targeting antibody anti-CD3. The essential routing pathway is (1) localization to coated pits for endocytosis, (2) escape from lysosomal routing, and (3) return to the plasma membrane. Any antibody which can route in this manner will be effective with the toxin moiety, irrespective of the epitope to which the antibody is directed. Thus, a wide variety of cell types can in principle be targeted. When antibodies dissociate from their receptors due to changes in receptor configuration induced in certain receptors as a consequence of endosomal acidification, they enter the lysosomal pathway. This can be prevented or minimized by directing the antibody towards an ecto-domain epitope on the same receptor which is closer to the plasma membranes (Ruud, et al. (1989) *Scand. J. Immunol.* 29:299; Herz et al. (1990) *J. Biol. Chem.* 265:21355). Other DT binding site mutants can be used to form derivatives by changing amino acids in the C-terminus which can reduce the binding function as long as the translocation function is maintained. Specific examples are described in the Examples.

In another embodiment, the present invention relates to an anti-CD3-CRM9 immunotoxin or derivatives thereof The design of successful derivatives of anti-CD3-CRM9 depend upon understanding how the unique concentration of anti-CD3-CRM9 achieves its biological effect.

An example of a series of derivatives which is likely to be effective are antibody-CRM9 conjugates directed at unique Vα and Vβ gene segment products of the T cell receptor. Some of these epitopes appear to be biased towards specific autoimmune processes. Such conjugates should be useful in specific autoimmune diseases (Kappler et al. (1987) *Cell* 49:263; Urban et al. (1988) *Cell* 54:577).

Relatedly, the invention provides an anti-Vβ-CRM9 immunoconjugate such as anti-Vβ$_{f2}$-CRM9. Also provided is an anti-Vα-CRM9 immunoconjugate. Both of the conjugates can be placed in a pharmaceutically acceptable carrier for administration to a subject. Both acid-cleavable and non-cleavable protein cross-linking reagents can be used in the construction of antibody-diphtheria toxin binding-site mutant conjugates like anti-CD3-CRM9 (Neville et al. (1989) *J. Biol. Chem.* 264:14653–14661); preferred are non-cleavable crosslinkers, such as bismaleimidohexane and m-maleimidobenzoyl-N-hydroxysuccinimide ester. The synthesis of acid-cleavable protein cross-linking reagents based on orthoester, acetal, and ketal functionalities has been described (Srinivasachar and Neville (1989) *Biochemistry* 28:2501–2509). The unique feature of these functionalities is that their observed hydrolytic rate constants increase 10-fold for each drop in pH, a consequence of specific $H_3O^+$ catalysis leading to a carbonium ion intermediate (Cordes and Bull (1974) *Chem. Rev.* 74:581–603). Moreover, these functionalities are resistant to base catalysis permitting manipulation and storage at alkaline pH. The cross-linking reagents react with proteins via heterobifunctional groups (maleimide and N-hydroxysuccinimide ester) or homobifunctional groups (bis-maleimide). The maleimide cross-linking is accomplished by prior protein thiolation with iminothiolane. Cross-linked proteins exhibit first-order dissociation under acid conditions. The $t_{1/2}$ at pH 5.5 varies between 0.1 and 130 h for a series of six different cleavable cross-linkers (Srinivasachar and Neville (1989) *Biochemistry* 28:2501–2509).

Figure 16:
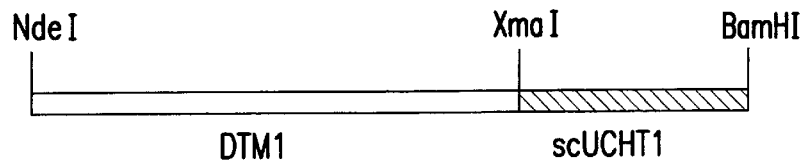
FIG. 16 shows the cloning scheme used to obtain scUCHT1 fusion protein with DTM1 and DT 483.
Figure 16:
Figure 16:
Figure 16:
Figure 16:
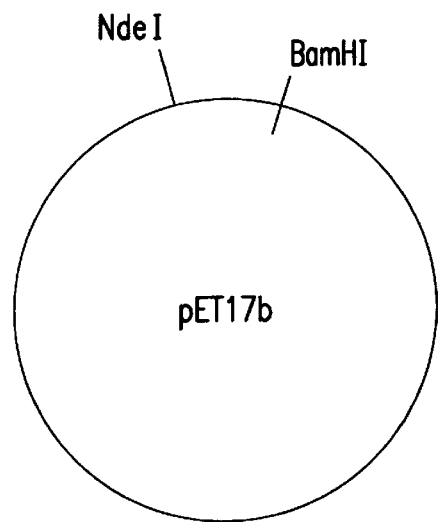
Figure 17:
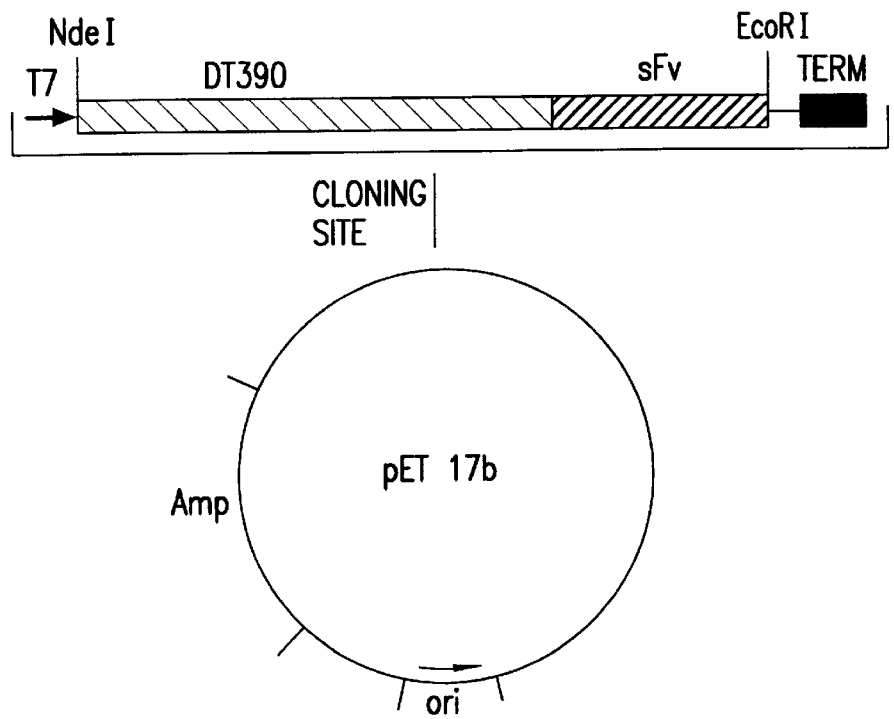
FIG. 17 shows the cloning scheme used to obtain scUCHT1 fusion protein with DT 390.
Figure 18:
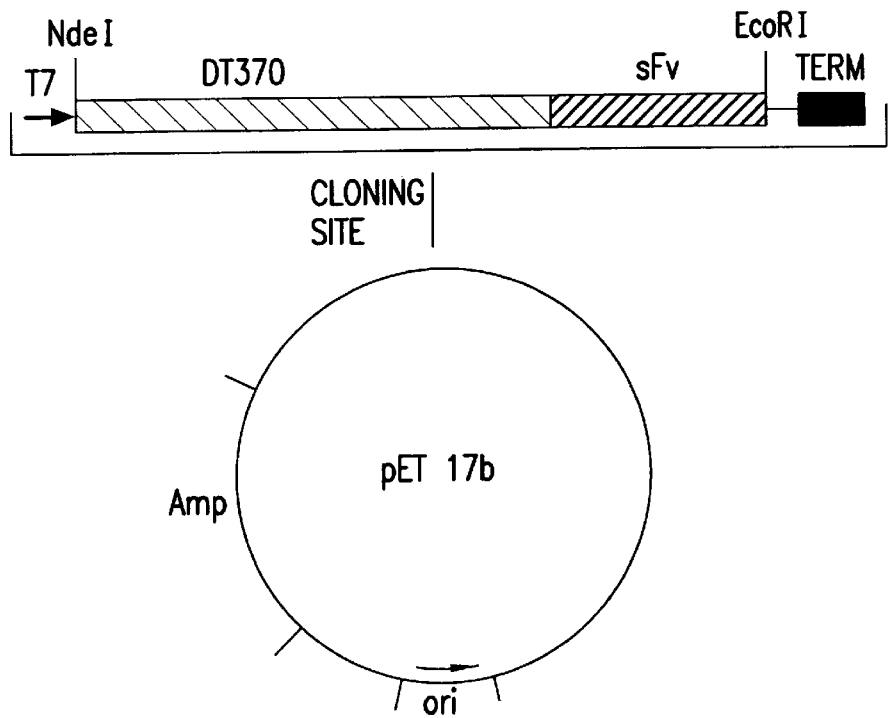
FIG. 18 shows the cloning scheme used to obtain scUCHT1 fusion protein with DT 370.

The mutant diphtheria toxin moiety can be a truncated mutant, such as DT390, DT383, DT370 or other truncated mutants, as well as a full length toxin with point mutations, such as DTM1, as described in Examples 9–11. scUCHT1 fusion proteins with DTM1 and DT483 (see FIG. 16), DT390 (FIG. 17) and DT370 (FIG. 18) have been cloned and expressed in *E. coli*. The antibody moiety can be scUCHT1 or other anti-CD3 antibody having the characteristics set forth herein. Thus, one example of an immunotoxin for use in the present methods is UCHT1-DT390. The described immunotoxins can be used in all the methods of the invention.

Other examples of immunotoxins include anti-Vβ-CRM9 and anti-Vα-CRM9. For example, the antibody-CRM9 conjugate used in any of the methods herein can be an anti-Vβ-CRM9 such as anti-Vβ$_8$-CRM9. In addition, the antibody-CRM9 conjugate can be an anti-Vα-CRM9. In one embodiment, the anti-Vβ-CRM9 is anti-Vβ$_{12}$-CRM9 and the disease is human immunodeficiency virus disease or the Acquired Immunodeficiency Syndrome (AIDS). Other Vα and Vβ targets associated with particular autoimmune diseases exist. For example, pulmonary sarcoidosis showed increased usage of the Vβ$_8$ subset in blood and lung lymphocytes (Moller et al. (1988) *J. Clin. Invest.* 82:1183–1191). In multiple sclerosis, preferential use of the Vβ$_{5.2}$ subset in brain plaque lesions has been identified and rearrangements Of Vα$_{1, 2, 7, 8, and 10}$ were also prominent (Oksenberg et al. (1993) *Nature* 362:68–70).

The antibody-toxin constructs of the invention can be expected to be effective as immunotoxins, because the relevant parameters are known. The following discussion of parameters is relevant to the use of the immunotoxin in tolerance induction. The relevant binding constants, number of receptors and translocation rates for humans have been determined and used. Binding values for anti-CD3-CRM9 for targeted and non-targeted cells in vitro are described above. Rates of translocation for the anti-CD3-CRM9 conjugate to targeted and non-targeted cells in vitro are described in references cited at page 2 (Greenfield et al. (1987) *Science* 238:536; Johnson et al. (1988) *J. Biol. Chem.* 263:1295; Johnson et al. (1989) *J. Neurosurg.* 70:240; and Neville et al. (1989) *J. Biol. Chem.* 264:14653). The rate limiting translocation rate to targeted cells in vitro is recited at page 5, wherein it is shown that the conjugate is translocated to about 40% of the target cells present as measured by inhibition of protein synthesis in about 40% of cells. Inhibition of protein synthesis is complete in cells into which the conjugate translocates.

Parameters determined in in vivo studies in nude mice include the following: Tumor burden is described in Example 1 as a constant mass equal to 0.1% of body weight;

the receptor number and variation of receptor number are described in Example 3; "favorable therapeutic margin" is defined as an in vivo target cell 3 log kill at 0.5 MLD (minimum lethal dose) comparison of efficacy with an established treatment of 0.5 MLD immunotoxin equivalent (group 1) to a radiation dose of 500–600 cGy (groups 8 and 9).

The parameters determined in vitro allowed the prediction of success in the in vivo nude mouse study. The prediction of in vivo success was verified by the data in Examples 3–4. Using the target cell number from the mouse study as being equivalent to the local T cell burden in a monkey or man successful T cell ablation and immunosuppression in monkeys could be predicted. This prediction has been verified by the monkey data in Examples 5 and 7–8. Using the same parameters, a scientist skilled in this field can make a prediction of success in humans with confidence, because these parameters have been previously shown to have predictive success.

In another embodiment, the present invention relates to a pharmaceutical composition comprising anti-CD3-DT mutant in an amount effective to treat T cell leukemias or lymphomas which carry the CD3 epitope, graft-versus-host disease or autoimmune diseases, and a pharmaceutically acceptable diluent, carrier, or excipient. One skilled in the art will appreciate that the amounts to be administered for any particular treatment protocol can readily be determined. Suitable amounts might be expected to fall within the range of 0.01 to 1.0 mg (toxin content) per kg of body weight.

Non-toxic mutant of diphtheria toxin.

Most human sera contain anti-DT neutralizing antibodies from childhood immunization. To compensate for this the therapeutic dose of anti-CD3-CRM9 can be appropriately raised without affecting the therapeutic margin. Alternatively, the present application provides a non-toxic DT mutant reactive with neutralizing antisera (e.g., CRM197) that can be administered in conjunction with the immunotoxin.

A non-toxic mutant of diphtheria toxin for use in the present methods can be DTM2 or CRM197. DTM2 and CRM197 are non-toxic mutants of DT, having a point mutation in the enzymatic chain. However, they have the full antigenic properties of DT and CRM9, and CRM197 is used for immunization (Barbour et al. 1993. *Pediatr Infect. Dis. J.* 12:478–84). Other non-toxic DT mutants that can be used in the present method will share the characteristic of totally lacking A chain enzymatic activity.

The purpose of administering the non-toxic toxin is to bind preexisting anti-CRM9 and anti-DT antibodies in a subject and compete with their effect and/or induce their removal from the circulation. This substantially avoids any host immune response to the immunotoxin that might interfere with the activity of the immunotoxin.

The protein synthesis inhibition assay in the presence of human serum samples or pooled human sera described in the Examples becomes an important part of the evaluation of the optimal immunotoxin for the individual patient and is provide for this purpose. This assay makes routine the systematic evaluation of additional combinations of DT point mutations and carboxy-terminal deletions for the purpose of minimizing blockade of immunotoxin in vivo by anti-human antitoxin.

The non-toxic mutant is preferably administered concurrently with or shortly before the immunotoxin. For example, the non-toxic DT mutant can be administered within an hour, and preferably about 5 minutes prior to the administration of immunotoxin. A range of doses of the non-toxic mutant can be administered. For example, an approximately 10 to 100 fold excess of non-toxic mutant over the CRM9 content of the immunotoxin to be administered can be administered by I.V. route.

Another use of the non-toxic DT mutant in the present methods is to run the recipient patient's blood through a column containing the non-toxic DT mutant to remove some or all of the patient's serum antibodies against DT.

Method of Inducing Immune Tolerance.

One embodiment to the invention provides a method of inhibiting a rejection response by inducing immune tolerance in a recipient to a foreign mammalian donor organ cell by safely exposing the recipient to an immunotoxin so as to reduce the recipients's peripheral blood T-cell lymphocyte population by at least 80%, and preferably 95% or higher, wherein the immunotoxin is an anti-CD3 antibody linked to a diphtheria protein toxin, and wherein the protein has a binding site mutation. The term "safely" in this context means that recipient is not killed by the immunotoxin. The term "donor cell" refers to a donor organ or a cell or cells of the donor organ, as distinguished from donor lymphocytes or donor bone marrow. When the donor organ or cells of the donor is transplanted into the recipient, a rejection response by the recipient to the donor organ cell is inhibited and the recipient is tolerized to the donor organ cell. Alternatively, a non-toxic DT mutant such as DTM2 or CRM197 can first be administered followed by the immunotoxin. This method can use any of the immunotoxins (e.g., anti-CD3-CRM9, scUCHT1-DT390, etc.) or non-toxic DT mutants described herein with the dosages and modes of administration as described herein or otherwise determined by the practitioner.

As further described in the Examples, the above-described method for inducing tolerance can be augmented by additional treatment regimens. For example, the method can further include administering to the thymus gland a thymic apoptosis signal before, at the same time, or after, the immunotoxin exposure step. The thymic apoptosis signal can be high dose corticosteroids (also referred to as "immunosuppressants" in this context). The thymic apoptosis signal can be lymphoid irradiation.

In a further example of the method of inducing tolerance, thymic injection of donor leukocytes or lymphocytes having MHC antigen of the same haplotype as the MHC of the donor cell can be administered to the recipient. Thymic injection of a saline solution or a crystalloid or colloid solution to disrupt thymic integrity and increase access of immunotoxin to the thymus can also be beneficial.

The present tolerance induction method can also include administering an immunosuppressant compound before, at the same time, or after, the immunotoxin exposure step. The immunosuppressant compound can be deoxyspergualin, cyclosporin or other cyclophylins, mycophenolate mofetil (Roche), FK506, IL-12 inhibitors or other known immunosuppressants. The method of inducing immune tolerance can further comprise administering donor bone marrow at the same time, or after, the exposure step.

Any one, two, or more of these adjunct therapies can be used together in the present tolerance induction method. Thus, the invention includes at least six methods of inducing tolerance using immunotoxin (IT): (1) tolerance induction by administering IT alone; (2) tolerance induction by administering IT plus other drugs that alter thymic function such as high dose corticosteroids; (3) tolerance induction by administering IT plus immunosuppressant drugs such as cyclosporin (4) tolerance induction by administering IT plus other drugs that alter thymic function, plus immunosuppressant drugs; (5) tolerance induction by administering IT and bone marrow; and (6) tolerance induction by administering IT plus bone marrow, plus other drugs that alter thymic function, plus immunosuppressant drugs. The adjunct therapy can be administered before, at the same time or after the administration of immunotoxin. Different adjunct therapies can be administered to the recipient at different times or at the same time in relation to the transplant event or the administration of immunotoxin, as further described below.

Because the immunosuppressant can be administered before the immunotoxin and/or other treatments, the present method can be used with a patient that has undergone an organ transplant and is on an immunosuppressant regimen. This presents a significant opportunity to reduce or eliminate traditional immunosuppressant therapy and its well documented negative side-effects. Also, as described below, treatment with immunosuppressants prior to transplantation could be particularly useful in cadaveric transplants. In such a setting of pre-transplant treatment with immunosuppressant, the administration of immunotoxin can be advantageously delayed for up to seven or more days post-transplantation.

An example of a schedule of immunotoxin and immunosuppressant administration for patients receiving live organ transplants is as follows:

day −7 to day 0: begin immunosuppressant treatment;

day 0: perform transplant;

day 7: begin immunotoxin and non-toxic DT toxin treatment;

day 9: end immunotoxin treatment;

day 11: end immunosuppressant treatment.

In another example, non-toxic DT mutant is administered seven days before the transplant and immunotoxin is administered seven days after the transplant.

The immunotoxin injection can also be made within a week or two prior to the donor cell treatment. If the donor organ or cell from donor organ is from a live donor, the immunotoxin is preferably administered from 15 hours to 7 days before the transplanting step. If the donor organ is kidney or kidney cells and is from a cadaver, the immunotoxin is preferably administered from 6 to 15 hours before the transplanting step. If the donor organ or cell from the donor organ is from a cadaver and is selected from the group consisting of heart, lung, liver, pancreas, pancreatic islets and intestine, the immunotoxin is preferably administered from 0 to 6 hours before the transplanting step. For practical reasons immunotoxin treatment and transplantation generally take place at about the same time (e.g., within 15 hours), because advanced planning for cadaveric transplants is difficult. Various schedules of apoptotic and immunosuppressant therapies can be used with the above methods. In any of the above scenarios, donor bone marrow, if desired, can be administered at approximately the time of the transplant or after.

The preferred doses of the immunotoxin are those sufficient to deplete peripheral blood T-cell levels to 80%, preferably 90% (or especially preferably 95% or higher) of preinjection levels. This should require mg/kg levels for humans similar to those for monkeys (e.g. 0.15 mg/kg to 0.2 mg/kg body weight), which toxicity studies indicate should be well tolerated by humans. Thus, the immunotoxin can be administered to safely reduce the recipients T cell population.

Method of Treating Graft-Versus-Host Disease.

In another embodiment, the invention relates to a method of treating an immune system disorder not involving T cell proliferation which is amenable to T cell suppression. More specifically, a method of treating graft-versus-host disease in an animal is also provided. It comprises administering to the animal an immunotoxin comprising a diphtheria toxin binding mutant moiety and an antibody moiety which routes by the anti-CD3 pathway, or derivatives thereof under conditions such that the graft-versus-host disease is treated, i.e., the symptoms of the graft-versus-host disease improve. Alternatively, as further described, a non-toxic DT mutant such as DTM2 or CRM197 (or mutants having combinations of the mutations in CRM9 and CRM197) can first be administered followed by the immunotoxin. This method can use any of the immunotoxins or non-toxic DT mutants described herein with the dosages and modes of administration as described herein or otherwise determined by the practitioner.

GVHD is a morbid complication of bone marrow transplantation which is often performed as anti-leukemia/lymphoma therapy. GVHD is caused by circulating donor T cells within the host which are acquired in bone marrow grafts unless specifically depleted prior to grafting (Gale and Butturini (1988) *Bone Marrow Transplant* 3:185; Devergie et al. (1990) ibid 5:379; Filipovich et al. (1987) *Transplantation* 44). Successful donor T cell depletion techniques have been associated with a higher frequency of graft rejection and leukemia relapses (Gale and Butturini (1988) *Bone Marrow Transplant* 3:185; Devergie et al. (1990) ibid 5:379; Filipovich et al. (1987) *Transplantation* 44). Therefore, the donor T cells appear to aid engraftment and to provide a graft-versus-leukemia effect as well as causing GVHD. Because the T cell burden following bone marrow transplantation is low for the first 14 days (<10% of normal) the log kill of donor T cells would be proportionally enhanced (Marsh and Neville (1987) *Ann. N.Y. Acad. Sci.* 507:165; Yan et al., submitted; Gale and Butturini (1988) *Bone Marrow Transplant* 3:185; Devergie et al. (1990) ibid 5:379; Filipovich et al. (1987) *Transplantation* 44). It is expected that donor T cells can be eliminated at set times during the early post transplantation period using the present method. In this way the useful attributes of grafted T cells might be maximized and the harmful effects minimized.

Method of Treating an Autoimmune Disease.

Another embodiment of the invention provides a method of treating an autoimmune disease in an animal comprising administering to the animal an immunotoxin comprising a diphtheria toxin binding mutant moiety and an antibody moiety which routes by the anti-CD3 pathway, or derivatives thereof, under conditions such that the autoimmune disease is treated, e.g., the symptoms of the autoimmune disease improve. A further method of treating an autoimmune disease in an animal comprises administering to the animal a non-toxic mutant of diphtheria toxin followed by an antibody CRM9 conjugate which routes by the anti-CD3 pathway, or derivatives thereof, under conditions such that the autoimmune disease is treated. This method can use any of the immunotoxins or non-toxic DT mutants described herein with the dosages and modes of administration as described herein or otherwise determined by the practitioner.

Method of Treating T Cell Leukemias or Lymphomas.

A further embodiment of the invention provides a method of treating T cell leukemias or lymphomas which carry the CD3 epitope in an animal comprising administering to the animal an immunotoxin comprising a binding site mutant of diphtheria toxin moiety and an antibody moiety which routes by the anti-CD3 pathway, or derivatives thereof, under conditions such that the T cell leukemias or lymphomas are treated. Alternatively, a further embodiment is a method of treating T cell leukemias or lymphomas in an animal comprising administering to the animal a non-toxic mutant of diphtheria toxin followed by an antibody-CRM9 conjugate which routes by the anti-CD3 pathway, or derivatives thereof, under conditions such that the T cell leukemias or lymphomas are treated. This method can use any of the immunotoxins or non-toxic DT mutants described herein with the dosages and modes of administration as described herein or otherwise determined by the practitioner.

Method of Treating Acquired Immunodeficiency Syndrome.

A method is provided for treating acquired immunodeficiency syndrome in an animal, comprising administering to the animal an immunotoxin comprising a diphtheria toxin binding mutant moiety and an antibody moiety which routes by the anti-CD3 pathway, or derivatives thereof under conditions such that the acquired immunodeficiency syndrome is treated. Alternatively, a method of treating acquired immunodeficiency syndrome in an animal, comprising administering to the animal a non-toxic mutant of diphtheria toxin followed by an antibody-CRM9 conjugate which routes by the anti-CD3 pathway or derivatives thereof under conditions such that the acquired immunodeficiency syndrome is treated is provided. This method can use any of the immunotoxins or non-toxic DT mutants described herein with the dosages and modes of administration as described herein or otherwise determined by the practitioner. However, anti-V$\beta_{12}$ is a likely conjugate for use in this method.

Radiation induced T cell ablation with concomitant high dose zidovudine therapy followed by bone marrow transplantation has been reported to eradicate HIV-1 infection in one case (Holland et al. (1989) *Ann. Int. Med.* 111:973). Cyclophosphamide, a T cell suppressive reagent, has been shown to be beneficial in treating murine AIDS (Simard and Joliceur (1991) *Science* 251:305). Anti-CD3-CRM9 provides extensive T cell ablation without the requirement of bone marrow reconstitution.

In any of the methods recited, a H1 histamine blocking agent such as Benadryl or Tagevil can be administered I.V. prior to administering the non-toxic mutant to minimize any possibility of an anaphylactic reaction. No evidence of anaphylactic reaction was noted in the primate experiments described in the Examples. However, the H1 histamine blocker can be administered as a precaution with no significant disadvantage.

The immunotoxin described here is more toxic on a weight basis than hemi-immunotoxins, but at tolerated doses exhibits an apparent log kill of targeted cells at target cell burdens encountered clinically. This constitutes a favorable therapeutic margin. Most human sera contain anti-DT neutralizing antibodies from childhood immunization (Johnson et al. (1989) *J. Neurosurg.* 70:240). To compensate for this the therapeutic dose of anti-CD3-CRM9 can be appropriately raised without affecting the therapeutic margin. The doses for immunotoxin and, where used, the non-toxic DT mutant are described in the Examples.

The present invention will be illustrated in further detail in the following non-limiting examples.

EXAMPLE 1

Establishment of Tumors

The experimental design of the studies that give rise to the present invention was dictated by the goal of having an animal model as closely relevant to human in vivo tumor therapy as possible. In order to minimize the host killer cell immune response, bg/nu/xid strain of nude mice were used (Kamel-Reid and Dick (1988) *Science* 242:1706). The human T cell leukemia cell line, Jurkat, was chosen because of previous studies with this line and its relatively normal average complement of CD3 receptors (Preijers et al. (1988) *Scand. J. Immunol.* 27:553). The line was not cloned so that receptor variation among individual cells existed (FIG. 1 legend). A scheme was developed whereby well established tumors of constant mass equal to 0.1% of body weight ($\approx 4\times10^7$ cells) could be achieved 7 days after inoculation of Jurkat cells (see FIG. 1 and Dillman et al. (1988) *Cancer Res.* 15:5632). This required prior irradiation and inoculation with lethally irradiated helper feeder cells (see FIG. 1 and Dillman et al. (1988) *Cancer Res.* 15:5632).

EXAMPLE 2

Guinea Pig Studies

Immunotoxin toxicity studies were performed in guinea pigs, an animal (like humans) with a high sensitivity to diphtheria toxin (mice are highly resistant to diphtheria toxin). Therapy of CRM9 conjugates was set at ½ the guinea pig minimum lethal dose. In this study, minimum lethal dose (MLD) is defined as the minimum tested dose which results in both non-survivors and survivors over a 4 week evaluation period. All animals survive when a MLD is reduced by 0.5. MLD was evaluated in guinea pigs (300–1000 g) by subcutaneous injection. The following MLDs were found and are listed as μg of toxin/kg body weight; DT, 0.15; CRM9, 30; anti-CD5-DT (cleavable), 0.65; anti-CD5-CRM9 (non-cleavable), 150. Finally, the therapeutic efficacy of the immunotoxin treatment in producing tumor regressions was compared to graded doses of whole body irradiation which resulted in similar tumor regressions.

EXAMPLE 3

Comparison of Immunotoxins

Several types of immunotoxins were compared in this study. They were synthesized as previously described by thiolating both the monoclonal antibody moiety and the toxin moiety and then crosslinking the bismaleimide crosslinkers (Neville et al. (1989) *J. Biol. Chem.* 264:14653). Purification was performed by size exclusion HPLC columns and fractions containing 1:1 toxin:antibody mol ratios were isolated for these studies. Conjugates made with an acid-labile crosslinker bismaleimidoethoxy propane were compared with a non-cleavable, bismaleimidohexane. Conjugates made with this cleavable crosslinker have been shown to hydrolyze within the acidifying endosome releasing free toxin moieties with half-times of hydrolysis measured at pH 5.5 of 36 min (Neville et al. (1989) *J. Biol. Chem.* 264:14653).

The results of this study are tabulated in Table I. Non-treatment groups such as group 10, groups treated with anti-CD5 immunotoxins (groups 5 and 6), and group 4 treated with a mixture of anti-CD3 and CRM9 did not show regression. The vascularized tumor nodules that weighed 20 mg on day 7 grew to between 1.5 to 7.8 g on day 37 and weighed between 7.9 and 11.6 on day 56. No late spontaneous regressions were noted. In contrast, group 1 consisting of treatment with anti-CD3-CRM9 non-cleavable conjugate (NC) given at 25 μg/kg on days 7, 8, and 9 (see FIG. 1 time line) showed only 1 tumor out of 6 by day 37. Some of the remaining animals were subject to autopsy and they failed to reveal residual tumor or even scaring. Tumors identified as regressed on day 37 by superficial inspection did not reappear during the course of the study (56 days).

TABLE 1

IMMUNOTOXIN AND RADIATION TREATMENT ON SUBCUTANEOUS HUMAN
T CELL TUMORS (JURKAT) IN NUDE MICE

| Group | Treatment | Dose (intraperitoneal) | Animals Bearing Tumors At Day 37/Group Animals | % Tumor Regressions |
|---|---|---|---|---|
| 1 | Anti-CD3-CRM9 (NC)[a] | 25 μg/kg. × 3d | 1/6 | 83 |
| 2 | Anti-CD3-CRM9 (NC) | 19 μg/kg. × 2d | 1/4 | 75 |
|   | Anti-CD5-CRM9 (C) | 19 μg/kg. × 2d |   |   |
| 3 | Anti-CD3-CRM9 (C) | 25 μg/kg. × 3d | 2/4 | 50 |
| 4 | Anti-CD3 + CRM9 | 25 μg/kg. × 3d | 4/4 | 0 |
| 5 | Anti-CD5-CRM9 (C) | 25 μg/kg. × 3d | 5/5 | 0 |
| 6 | Anti-CD5-DT (NC) | 25 μg/kg. × 1d | 9/9 | 0 |
| 7 | γ radiation $^{137}$Cs | 400 cGy | 2/2 | 0 |
| 8 | γ radiation $^{137}$Cs | 500 cGy | 3/6 | 50 |
| 9 | γ radiation $^{137}$Cs | 600 cGy | 0/2[b] | 100 |
| 10 | None |   | 6/6 | 0 |

[a]Anti-CD3 refers to the monoclonal antibody UCHT1 and was purchased from Oxoid USA, Inc.
Anti-CDS refers to the monoclonal antibody T101 and was a gift from Hybritech (San Diego). NC and C refer, respectively, to non-cleavable and cleavable conjugates.
[b]These animals were evaluated on days 10 and 13 at the time of death from radiation sickness.

The cleavable crosslinker confers no therapeutic advantage to anti-CD3-CRM9 immunotoxins and may be less effective (group 3). Cleavable crosslinkers confer some advantage with anti-CD5-CRM9 conjugate in vitro (5) but had no effect in this in vivo system (group 5), and lacked significant potentiating effect when administered with anti-CD3-CRM9 (group 2). The cleavable crosslinker conferred a marked therapeutic advantage to anti-CD5 wild type toxin conjugates and tumor regressions were achieved. However, in these cases the guinea pig toxic dose was exceeded. A single dose on day 7 of cleavable anti-CD5-DT at 6 μg/kg produced 8/10 tumor regressions while a cleavable conjugate made with an irrelevant antibody (OX8) produced no regressions (4/4). However, this dose exceeded the guinea pig MLD by 9 fold. A rescue strategy was tried in which the above conjugate dose was given intravenously followed by DT antitoxin 4 hours later (also intravenously). The 4 hr rescue could not raise the MLD above 0.65 μg/kg. The 1 hr rescue could not raise the MLD above 0.65 μg/kg. The 1 hr rescue raised the MLD to 36 μg/kg, however, there were no tumor regressions in 10 mice receiving 21.5 μg/kg of the cleavable anti-CD5-DT conjugate.

In groups 7–9 increasing single doses of whole body radiation (102 cGy/min) were given to animals bearing 3×3×5 mm tumors. At 400 cGy no complete regressions occurred. At 500 cGy 50% complete tumor regressions occurred. At 600 cGy 100% regression was achieved as judged on day 10 and 13 when the animals died from radiation sickness. (Groups 7–9 did not receive prior radiation and tumor takes were less than 100%). It appears that the 75 μg/kg anti-CD3-CRM9 (NC) immunotoxin is equal in therapeutic power to between 500 and 600 cGy of radiation.

EXAMPLE 4

Estimation of Cell Kill

The actual cell kill achieved by the radiation and the immunotoxin can be estimated by assuming radiation single hit inactivation kinetics along with a $D_{37}$ value for the radiation. A value for $D_{37}$ of 70–80 cGy with n=1.2–3 is not unreasonable for a rapidly dividing helper T cell. $D_{37}$ is the dose of radiation which reduces the fraction of surviving cells to 1/e as extrapolated from the linear portion of the log survivors vs. dose curve and n is the intercept at 0 dose (Anderson and Warner (1976) in *Adv. Immunol.*, Academic Press Inc., 24:257). At a dose of 550 cGy the fraction of surviving cells is calculated to be about $10^3$. Since a majority of tumors completely regress at this dose, it is estimated that both therapies are producing an approximate 3 log kill. (The remaining cells, $4 \times 10^7 \times 10^3 = 4 \times 10^4$ cells apparently cannot maintain the tumor, i.e., the in vivo plating efficiency is low, a fairly typical situation in the nude mouse xenograft system.) The reliability of this 3 log kill estimate has been verified by determining the tissue culture plating efficiency by limiting dilution of 7 day established Jurkat tumors (following dispersal) and tumors exposed 18 hours earlier in vivo to 600 cGy. Plating efficiencies were 0.14 and $1.4 \times 10^4$, respectively. (Plating efficiency is the reciprocal of the minimum average number of cells per well which will grow to form one colony.

It should be emphasized that with high affinity holo-immunotoxins the cell kill is inversely proportional to the target cell number. This presumably occurs because receptors are undersaturated at tolerated doses and free conjugate concentration falls with increasing target cell burden (Marsh and Neville (1987) *Ann. N.Y. Acad. Sci.* 507:165; Yan et al. (1991) *Bioconjugate Chem.* 2:207). To put this in perspective, the tumor burden in this study is almost equal to the number of T cells in a mouse ($\approx 10^8$). It can be expected that a tolerated dose of anti-CD3-CRM9 immunotoxin can achieve an in vivo 3 log depletion of a normal number of CD3 positive T cells.

EXAMPLE 5

Cell Depletion in Rhesus Monkeys Induced by FN18-CRM9

FN18-CRM9 conjugate

Conjugation of anti-Vβ and anti-Vα IgG monoclonal antibodies to CRM9 is performed by the same methods used to conjugate anti-CD3 to CRM9 using a non-cleavable linker such as bismaleimidohexane and previously described in detail (Neville et al. (1988) *J. Biol. Chem.* 264:14653–61). The monoclonal antibody FN18 is the monkey equivalent of the human anti-CD3 (UCHT1) and is known to bind the same CD3 receptor epitopes (ε and γ) as bound by the human CD3 antibody and is the same isotype as the human CD3 antibody. Thus, in terms of the parameters relevant for predicting successful T cell depletion, the present CD3-CRM9 conjugate and FN18-CRM9 are expected to have the same activity.

Administration

Conjugates can be administered as an I.V. bolus in a carrier consisting of 0.1M $Na_2SO_4$+0.01M phosphate buffer, pH 7.4 plus 1 part in 50 of serum previously obtained from the subject. The dose schedule is every other or third day for 3 to 6 days. The total dose is preferably from 25 to 200 micrograms of toxin per kg of body weight.

The actual dose of FN18-CRM9 used was equal to 0.167 of the minimum lethal dose (MLD) in guinea pigs. Since the estimation of the MLD was performed in an animal lacking an immunotoxin target cell population (guinea pigs), the true MLD of FN18-CRM9 and anti-CD3-CRM9 is expected to be higher in monkeys and humans than in guinea pigs.

T Cell Kill

Helper T cell (CD4+ cells) numbers in peripheral blood fell dramatically after the initial administration of FN18-CRM9 in two rhesus monkeys. T cell counts began to rise by day 4 (sampled just prior to the second dose of FN18-CRM9). On day 5 in monkey 8629, CD4+ cells were depressed below the limit of detection (<50 cells/$mm^3$). Cells remained below or equal to 200/$mm^3$ out to day 21. This low level of CD4+ cells is associated with profound immunodeficiency in humans and in monkeys (Nooij and Jonker (1987) *Eur. J. Immunol.* 17:1089–1093). The remarkable feature of this study is the long duration of helper T cell depletion (day 21) with respect to the last administration of immunotoxin (day 4) since intravenously administered immunotoxins were cleared from the vascular system with half-lives <9 hours (Rostain-Capaillon and Casellas (1990) *Cancer Research* 50:2909–2916), the effect outlasting circulating immunotoxin. This is in contrast to T cell depletion induced by unconjugated anti-CD3 antibodies (Nooij and Jonker (1987) *Eur. J. Immunol.* 17:1089–1093).

In monkey 1WS the second dose of conjugate only appeared to result in a diminished rate of CD4+ cell recovery. However, CD4+ cells were still fewer than normal at day 21. The blunted response of monkey 1WS to the second dose of immunotoxin was found to be due to a preexisting immunization of this animal to the toxin. Monkey 1WS had a significant pre-treatment anti-diphtheria toxin titer as revealed by a Western blot assay. This titer was markedly increased at day 5, indicative of a classic secondary response. In contrast, monkey 8629 had no detectable pre-treatment titer and only a trace titer by day 5 and a moderate titer by day 28.

The specificity of FN18-CRM9 toward T cells can be seen by comparing the total white blood cell (WBC) count in the same two monkeys. WBCs fell, but only to 45% of baseline value on day 2 compared to 6% of baseline values for the CD4+ T cell subset. Most of the fall in WBC values can be accounted for by the T cell component of the WBC population (≈40%). However, B cells are initially depleted after FN18-CRM9 although these cells recover more quickly. FN18 is an IgG, isotype and as such is known to bind to $Fc_{II}$ receptors present on B cells and macrophages with low affinity. The FN18-CRM9 depletion of B cells indicates that significant interactions between the Fc portion of the FN18 antibody and B cells is taking place.

The peripheral T cell depletion induced by unconjugated FN18 at a dose known to produce immunosuppression 0.2 mg/kg/day (Nooij and Jonker (1987) *Eur. J. Immunol.* 17:1089–1093) was compared to the immunotoxin FN18-CRM9 administered at ⅑th the FN18 dose. Peripheral CD4+ T cell depletion is more pronounced and more long-lasting with the conjugate. The demonstration that FN18-CRM9 reduces peripheral helper T cell subset (CD4+) to levels less than or equal to 200 cell/$mm^3$ for a period as long as 21 days demonstrates that this immunotoxin and its anti-human analogs are effective immunosuppressive reagents.

The demonstration that FN18-CRM9 is a potent agent for inducing T cell depletion in non-human primates demonstrates that an anti-human homolog of FN18-CRM9, UCHT1-CRM9 (Oxoid USA, Charlotte, N.C.) for example, is a potent agent for inducing T cell depletion in humans.

The Fc binding region of anti-TCR/CD3 monoclonals may or may not be needed to induce T cell depletion when the anti-TCR/CD3 monoclonals are conjugated to CRM9. The $Fc_{II}$ binding regions can be removed, for example, by forming the conjugates with F(ab')$_2$ derivatives as is indicated in the literature (Thorpe et al. (1985) *J. Nat'l. Cancer Inst.* 75:151–159). In addition, anti-TCR/CD3 IgA switch variants such as monoclonal antibody T3. A may be used (Ponticelli et al. (1990) *Transplantation* 50:889–892). These avoid rapid vascular clearance characteristic of F(ab')$_2$ immunotoxins. F(ab')$_2$ and IgA switch variants of anti-TCR/CD3-CRM9 immunotoxins are therefore derivative anti-TCR/CD3 immunotoxins. These derivatives will avoid the B cell interaction noted and can increase specificity. However, $IgG_{2a}$, switch variants will maximize T cell activation through the $Fc_I$, receptor and may be useful in certain situations where T cell activation aids immunotoxin induced toxicity.

General methods to make antibodies lacking the Fc region or to make antibodies which are humanized are set forth in Harlow and Lane, Antibodies: A Laboratory Manual, Cold Spring Harbor Laboratory, Cold Spring Harbor, N.Y., 1988. Thus, as used in the claims, antibody can mean the entire antibody or any portion of the antibody sufficient for specific antigen or receptor binding.

EXAMPLE 6

Treatment of Autoimmune Diseases Using Other Antibody-CRM9 Conjugates which Route by the Anti-CD3 Pathway Since receptor recycling is a requirement for effective CRM9 based immunotoxins and since TCR/CD3 recycles as a unit, antibodies directed at other epitopes on TCR/CD3 will constitute effective derivatives, in particular antibodies directed at the approximately 50 Vβ subset families or the approximately equal number Vα subsets can be used to conjugate CRM9 and ablate specific Vβ or Vα subsets in vivo. In addition, in some cases it will be desirable to develop specific monoclonal antibodies reacting with unique rearrangements of either the Vα or Vβ subset families.

The advantage of targeting the specific Vβ or Vα subset(s) as opposed to the entire T cell population is twofold: (1) Elimination of a Vβ subset does not create a generalized immunodeficiency, only a hole in the immune repertoire is generated. Therefore, the ability to ward off most infections and maintain immune surveillance of most malignant transformations would remain intact. (2) Immunotoxin log kill increases linearly as the target cell burden decreases, assuming dose is unchanged. A 50-fold increase in log kill can be obtained as the target is changed from the entire set of T cells to a single VP subset. However, due to (1) the high affinity of binding of these immunotoxins, (2) the very low total dose given which is below target cell receptor saturation and (3) the irreversible nature of the endocytotic process, the target cells deplete the effective dose and this depletion decreases as target burden decreases. Since the log kill is exponential in effective dose, much higher increases in log kill than 50-fold on changing the target from T cells to a Vβ subset can occur. The expected increase in log kill will only occur if the immunotoxin is specific for the defined target. Extraneous interactions with other cell types via the antibody Fc piece is preferably eliminated.

Because HIV has been shown to preferentially infect one ($V\beta_{12}$) or a few of the 20 $V\beta$ subset families providing a small T cell reservoir of HIV replication, and because HIV infection apparently involves an unknown superantigen, CRM9 based immunotoxins directed at these specific $V\beta$ subsets such as anti-$V\beta_{12}$-CRM9 can reduce the HIV virus load. In addition, total ablation of a $V\beta$ subset in the presence of an endogenous superantigen can lead to long term ablation of the subset since maturing T cells are negatively selected in the presence of endogenous superantigens. Since the specific $V\beta$ subset respon TABLE 2-continued Efficacy of Anti-CD3-CRM9 With and Without CRM197 In Rhesus Monkeys
With Positive and Negative Anti-Diphtheria Toxin Titers.

| Monkey | Weight kg | Anti-DT Titer | Treatment | Post Treatment* Lymph node T/B Cell Ratio | Day(s) of Skin Graft Survival |
|---|---|---|---|---|---|
| M93 | 5.1 | 1:1000 | anti-CD3-CRM9 | 0.57 | 11, 12 |
| C81 | 1.0 | 1:1000 | CRMi97 + anti-CD3-CRM9 | 0.20 | 14, 15 |

*All monkeys received the same dose of immunotoxin 0.1 mg/kg total in divided doses on day 0, 1 and 2. Lymph node sampled on day 3. CRM197 when given in 100 fold excess over CRM9 content.
+In this study untreated animals show this lymph node T/B ratio
$Historical controls at TNO, Rijswijk
xxAnti-CD3 given at the same mol. dose as anti-CD3-CRM9

EXAMPLE 8

Immunotoxin UCHT1-CRM9 for the Treatment of Steroid Resistant Graft-Versus-Host Disease Treatment protocols for this type of disease can be expected to last a year, with Patients being followed for at least 5 years.

Characterization of UCHT1-CRM9 and CRM197

UCHT1-CRM9 is a covalent 1:1 conjugate of anti-human CD3 IgG1 monoclonal antibody and CRM9. The conjugate is synthesized, purified, sterile filtered and assayed for concentration, biological efficacy toward target cells and non-target cell toxicity by standardized culture assays. The method of synthesis, purification assay are identical to that used for FN18-CRM9 which was used in the pre-clinical monkey studies described in Examples 5–7.

CRM9 and CRM197 are produced by the Biotechnology Unit, NIH and purified by the Cooperating Facility. UCHT1 is produced in mouse ascites fluid and is purified by affinity chromatography over Protein A Sepharose. The synthesis, purification and storage of UCHT1-CRM9 is performed in a dedicated secure area. UCHT1-CRM9 is purified in 2 mg lots which are pooled and stored at 4° C. Shelf life is documented to be five months at full biological potency but does not exceed 4 months for this study. Preferably, most of the immunotoxin is used within 3 months of synthesis.

Patient Population

The patient population consists of individuals suffering from steroid resistant GVHD whose prognosis is poor. Patients are assayed for anti-CRM9 (anti-DT) titers and antibodies to murine immunoglobulin. Patients having anti-CRM9 titers of 1:1000 and below are treated according to the present protocol. Patients who have a history of receiving murine immunoglobulins or who exhibit positive anti-Ig titers may require special consideration.

Dosage of CRM9 Immunotoxin and Non-Toxic Mutant

UCHT1-CRM9 is administered at a dose which is 1/10 or less of the estimated minimum lethal dose (MLD) in a T lymphopenic patient. The MLD is expected to be at least 0.15 mg/kg (CRM9 content) based on the MLD of 0.15 mg/kg of IgG1-CRM9 in guinea pigs which lack a target cell population for the IgG1. (The presence of target cells in humans raises the MLD by providing a sink for the immunotoxin.) The optimal dose schedule has been found in monkeys to be administration on 3 consecutive days in 3 equally divided doses, and this schedule can be used throughout the treatment period. This permits administration of the total dose before any rise in pre-existing antitoxin titers due to a secondary response. In addition, the initial repopulation from the thymus is also eliminated, thus, further lowering the total T lymphocyte pool. Therefore, a total of 0.0125 mg/kg in three equally divided doses is given to the patient. This dose does induces T cell depletion in monkeys so that monitoring of T cell subsets and signs and symptoms of GVHD is relevant at the lowest dose. For the administration of this dose patients with anti-CRM9 titers of 1:100 or less will be treated. This permits pretreatment doses of CRM197 at 0.33 mg/kg or 1/10 the dose easily tolerated in monkeys. A second dosage group can include patients selected for antitoxin titers of 1:330 or less to whom CRM197 will be given at 1.0 mg/kg. A third dosage group can include patients with 1:1000 antitoxin titers or less will be given CRM197 at 3.3 mg/kg, a dose expected to be tolerable in humans, because it is easily tolerated by monkeys (see Example 7). The monkey MLD data should be very similar to humans on a per weight basis. However, GVHD patients are expected to be more like guinea pigs, because they have a smaller target cell population compared to non-GVHD patients.

Dose escalation can be tested by increasing the dose by a factor of 1.5. The following table exemplifies such a dose escalation test. For example three patients are used in each dosage group. There is a 3 to 4 week delay between each patient so that any late toxicity is detected before a dosage group is completed:

| Patient # | CRM9 Dose each day mg/kg | Total Dose mg/kg | Week ending |
|---|---|---|---|
| 1,2,3 | 0.00417 | 0.0125 | 12 |
| 4,5,6 | 0.00636 | 0.019 | 24 |
| 7,8,9 | 0.0083 | 0.028 | 36 |
| 10,11,12 | 0.0125 | 0.042 | 48 |

Assuming each patient weighs on the average 70 kg, the first dosage group will consume 2.6 mg of the CRM9 immunotoxin, and will be supplied as a pool of two 2 mg batches. The second group will consume 3.9 mg and will also be supplied as 2 pooled batches. The third group will require 5.9 mg and will be supplied as three pooled batches. The fourth group will require 8.9 mg and will be supplied as three pooled batches and an additional two pooled batches.

Administration

Prior to administering CRM197 a H1 histamine blocking agent such as Benadryl or Tagevil is given I.V. to minimize any possibility of an anaphylactic reaction (for Benadryl 4 mg/kg). The CRM197 is administered I.V. in a 5 mg/ml sterile filtered solution in phosphate buffered saline pH 7.4 (PBS) over a 5 min time period. The immunotoxin is then given I.V. at 0.2 mg/ml over 2 min time period in a sterile filtered solution of 0.90 mM sodium sulfate and 10 mM sodium phosphate pH 7.4.

Measurements of Biological Parameters

The following parameters can be measured at various intervals during treatment (as exemplified by the schedule below):

A Cytokines, TNF alpha, gamma IFN, IL-6
B Routine clinical chemistries
C WBC, Hct, diff; lymphocyte subsets CD3, CD4, CD8, CD2, CD16, CD20
D Body Weight
E Immune function assays. ELISA assays of serum to monitor antibody responses to UCHT1 (primary response) and CRM9 (secondary response). ELISA assays to monitor antibody responses to polio and DPT reimmunizations done at 1 year following bone marrow transplantation.

| (before IT) | Day 0 | A,B,C,D,E | Also A 2 hrs post |
|---|---|---|---|
| | Day 1 | A,C,D | |
| | Day 2 | A,C,D | |
| | Day 3 | A,B,C,D | |
| | Day 4 | C,D | |
| | Day 7 | A,C,D | |
| | Day 10 | B,C | |
| | Day 14 | A,C,D | |
| | Day 21 | C,D | |
| | Day 28 | A,B,C,D,E | |
| | Day 45 | C,D | |
| | Day 60, | B,C,D,E | |

EXAMPLE 9

An Anti-CD3 Single-Chain Immunotoxin with a Truncated Diphtheria Toxin Avoids Inhibition by Pre-Existing Antibodies in Human Blood The present Example examines the effect of human serum with pre-existing anti-DT antibodies on the toxicity of UCHT1-CRM9, an immunotoxin directed against CD3 molecules on T-lymphocytes. Sera with detectable anti-DT antibodies at 1:100 or greater dilutions inhibited the immunotoxin toxicity. Experiments with radiolabeled-UCHT1-CRM9 indicate that anti-DT antibodies partially block its binding to the cell surface as well as inhibit the translocation from the endosome to the cytosol. The inhibitory effect could be adsorbed using a full-length DT mutant or B-subfragment. A C-terminal truncation mutant could not adsorb the inhibitory effect, suggesting that the last 150 amino acids contain the epitope(s) recognized by the inhibitory antibodies.

Therefore, an anti-CD3 single-chain immunotoxin, sFv-DT390, was made with a truncated DT. The $IC_{50}$ of sFv-DT390 was $4.8 \times 10^{-11}$ M, 1/16 the potency of the divalent UCHT1-CRM9. More importantly, sFv-DT390 toxicity was only slightly affected by the anti-DT antibodies in human sera. "sFv" and "scUCHT1" both are singe chain antibodies containing the variable region.

Mutated full-length and truncated diphtheria toxin (DT) molecules are used for making immunotoxins. These immunotoxins show strong cytotoxic effects to their target cells, and some of them have already been used in clinical trials (1–7).] Previously, an immunotoxin directed against the CD3e molecule of the T-cell receptor complex, a pan T-cell marker was constructed. This construct is made with a monoclonal antibody of mouse-origin, UCHT1, and a binding site mutant of diphtheria toxin (DT), CRM9 (8). The immunotoxin, UCHT1-CRM9, is capable of regressing established xenografted human T-cell (Jurkat) tumors in nude mice (9). A rhesus monkey analog of UCHT1-CRM9, FN18-CRM9 was capable of not only depleting circulating T-cells but also depleting resident T-cells in the lymph nodes. This immunotoxin also delayed skin allograft rejection as compared to antibody treatment and non-treatment controls.

In contrast with ricin and Pseudomonas exotoxin (PE) based immunotoxins, there is a potential problem using UCHT1-CRM9, or other DT-based immunotoxins, in the treatment of human diseases. Most people have been immunized against DT. Therefore these people have a pre-existing anti-DT antibody titer which could potentially inhibit or alter the efficacy of these immunotoxins. This limitation also occurred in rhesus monkey studies. FN18-CRM9 could deplete T cells in the blood, but to a much lesser extent in animals with anti-DT antibodies, and the T cells repopulated several days earlier compared to those monkeys without anti-DT titers. In order to overcome this antibody mediated inhibition, the first examination of the effect and the mechanism of human sera containing anti-DT antibodies on UCHT1-CRM9 toxicity was done.

A DT point-mutant, a truncation mutant and DT-subfragments were used in an attempt to neutralize the anti-DT effect in human sera. Based on the neutralization data, a single-chain immunotoxin was constructed with a C-terminal deletion mutant of DT which is expected to bypass the inhibitory effect of the pre-existing anti-DT antibodies.

Cells

Jurkat cells (ATCC) were maintained in RPMI 1640 supplemented with 10% fetal calf serum, 25 mM sodium bicarbonate and 50 µg/ml of gentamycin sulfate.

Serum and adsorbing molecules

Goat anti-DT serum was provided by Dr Randall K. Holmes (USUHS, Bethesda, Md.). Human serum samples were provided by Dr. Henry McFarland (NINDS, NIH, Bethesda Md.). CRM197, an A-subfragment mutant (Gly 52 to Glu) of DT (see FIG. 2A), with no enzymatic activity (10) is available from Biocine-IRIS (Siena, Italy). MSPΔ5, a truncation mutant (amino acid 385) of DT with an additional 5 amino acids at the C-terminus was provided by Dr. Richard Youle (NINDS, NIH, Bethesda Md.). Purification of the DT B-subfragment has been described (11). Immunotoxins-UCHT1-CRM9 synthesis has been described (12).

The recombinant immunotoxin, sFv-DT390, was generated in two phases. First the coding sequences for the variable light ($V_L$) and variable heavy ($V_H$) chain regions of the UCHT1 antibody were amplified by a two step protocol of RT-PCR using primers based on the published sequence (13). The 5' $V_L$ primer added a unique NcoI restriction enzyme site while the 3' $V_H$ primer added a termination codon at the J to constant region junction and an EcoRI site. The $V_L$ region was joined to the $V_H$ region by single-stranded overlap extension and the two regions are separated by a $(Gly_3Ser)_4$ linker that should allow for proper folding of the individual variable domains to form a function antibody binding site (14). Second, genomic DNA was isolated from a strain of C. diphtheriae producing the DT mutant CRM9 (C7[β$^{htox-201tox-9h}$]) as described (15). This DNA was used for PCR. The 5' primer was specific for the toxin gene beginning at the signal sequence and added a unique NdeI restriction site. The 3' primer was specific for the DT sequence terminating at amino acid 390 and added an NcoI site in frame with the coding sequence. The PCR products were digested with the appropriate restriction enzymes and cloned into the E. coli expression plasmid pET-17b (Novagen, Inc., Madison, Wis., USA) which had been linearized with NdeI and EcoRI. The resulting plasmid was used to transformed E. coli BL21/DE3 cells. Cells were grown to an $OD_{590}$ of 0.5, induced with 0.5 M IPTG (Invitrogen, San Diego, Calif., USA) and incubated for an additional 3 hours. The sFv-DT390 protein was isolated in the soluble fraction after cells were broken with a French Press and the lysate subjected to centrifugation at 35,000×g.

Protein synthesis inhibition assay

Inhibition assays were performed as described (12) with the following modifications. Immunotoxins were incubated for 30 minutes with the indicated serum sample or leucine free medium at room temperature prior to addition to cells. In some experiments the serum was pre-incubated for 30 minutes with an adsorbing molecule at the given concentrations to bind the antibodies. The immunotoxin/serum mixture was incubated with Jurkat cells ($5\times10^4$ cells/well in 96 well plate) for 20 hours. A 1 hour pulse of [$^3$H]-leucine (4.5 µCi/ml) was given before cells were collected onto filters with a Skatron harvester. Samples were counted in a Beckman scintillation counter. Each experiment was performed in 4 replicates. Results were calculated into a mean value, and recorded as a percentage of control cells.

Serum antibody detection

Anti-DT antibodies were detected in human serum by ELISA. CRM9 (10 µg/ml) was adsorbed to Costar 96-well EIA/RIA flat bottom plates (Costar, Cambridge, Mass., USA) for 2 hours and then washed in phosphate buffered saline (PBS) containing 0.1% Tween 20. Each well was then incubated with PBS containing 3% gelatin to prevent non-specific binding of antibodies to the plastic. Serum samples were diluted in PBS containing 0.1% Tween 20 and 0.3% gelatin prior to addition to the plate. After 1 hour incubation, the wells were washed as above, and incubated for an additional hour with protein A/G-alkaline phosphatase (1:5,000; Pierce, Rockford, Ill., USA). Wells were washed, and phosphatase substrate (Pierce) was added following the manufacturer's directions. After 30 minutes color development was stopped with NaOH and the optical density (OD) was measured with a kinetic microplate reader (Molecular Devices Corporation, Palo Alto, Calif., USA). Each sample was performed in triplicate. Results are presented as O.D. values and antibody titers.

Endocytosis assay

UCHT1-CRM9 was iodinated using the Bolton-Hunter reagent (NEN Dupont, Wilmington, Del., USA) as described (16). Jurkat cells were washed twice with binding medium (RPMI 1640 supplemented with 0.2% bovine serum albumin, 10 mM Hepes (pH 7.4) and without sodium bicarbonate). Cells ($1.5\times10^6$) were incubated for 2 hours on ice with $^{125}$I-UCHT1-CRM9 ($1\times10^{-9}$ M) that had been pre-incubated with serum or binding medium. Unbound antibody was removed by washing the cells twice in PBS (pH 7.4) with centrifugation and resuspension. Duplicate samples were incubated for 30 minutes on ice or at 37° C. One sample from each temperature point was centrifuged at 800×g to separate the total cell associated (pellet) from the exocytosed or dissociated counts (supernatant). Both fractions were counted in a Beckman a γ-counter. To determine the amount of internalized immunotoxin, cells from the second sample at each temperature were incubated in low pH medium (binding medium containing 10 mM morpholinoethanesulfonic acid, all of which was titrated to pH 2.0 with HCl) for 5 minutes to dissociate the surface bound $^{125}$I-immunotoxin (17). Samples were centrifuged at 800×g to separate the internalized (pellet) from the membrane bound (supernatant). Both fractions were counted in a Beckman γ-counter (Beckman, Fullerton, Calif., USA).

Serum with anti-DT antibodies inhibits UCHT1-CRM9 toxicity

Since humans are immunized against DT, the presence of anti-DT antibodies in the serum was determined by ELISA (Table 3). In a limited sample population, 80% of the serum samples had an anti-DT antibody titer of 1:100 or above. The vaccination status of the donors was not available. To determine the effect of these antibodies on UCHT1-CRM9 toxicity, the immunotoxin was pre-incubated with different concentrations of serum and the toxicity of the mixture was assayed (Table 3). Serum samples without a significant ELISA O.D. (2 fold above background) were incapable of affecting UCHT1-CRM9 toxicity at high concentrations of serum (1:10). However, serum samples with a positive ELISA result could neutralize the cytotoxic effect at 1:10 dilution, and those with a high ELISA O.D. (7–11 fold above background) inhibited toxicity even at a 1:100 dilution. Similar results were seen in assays conducted with monkey serum samples.

TABLE 3

Human serum with anti-DT antibodies inhibits the toxicity of UCHT1-CRM9 and the inhibition correlates with the anti-DT titer

| | ELISA | | Protein Synthesis[b] (% control) | | |
|---|---|---|---|---|---|
| Sample | O.C. (X ± S.D.) | Titer | 1:10 | 1:100 | 1:1,000 |
| 10010 | 0.738 ± 0.017 | 1:750 | 97 ± 3 | 79 ± 8 | 2 ± 0 |
| 10011 | 0.568 ± 0.048 | 1:500 | 104 ± | 13 ± 2 | 2 ± 0 |
| 10012 | 0.491 ± 0.025 | ND[c] | 96 ± 3 | 19 ± 2 | 2 ± 0 |
| 10013 | 0.411 ± 0.052 | 1:500 | 105 ± 8 | 7 ± 1 | 2 ± 0 |
| 10014 | 0.390 ± 0.047 | 1:500 | 96 ± 2 | 7 ± 0 | 2 ± 0 |
| 10015 | 0.353 ± 0.008 | 1:250 | 125 ± 6 | 6 ± 4 | 2 ± 0 |
| 10019 | 0.359 ± 0.019 | 1:250 | 101 ± 7 | 6 ± 1 | 2 ± 0 |
| 10016 | 0.141 ± 0.015 | 1:100 | 22 ± 1 | 3 ± 0 | 2 ± 0 |
| 10017 | 0.100 ± 0.006 | <1:100 | 4 ± 0 | 3 ± 0 | 2 ± 0 |
| 10018 | 0.071 ± 0.001 | <1:100 | 2 ± 0 | 2 ± 0 | 2 ± 0 |
| Goat | 1.450 ± 0.013 | 1:10$^5$ | | 102 ± 19 | 104 ± 3 |

[a]ELISA was performed in tripiicate for each serum sample as described under "Materials and Methods." The O.D. values were derived from 1:100 dilutions and presented as a mean value ± SD. The background value was 0.060 ± 0.02. titers are recorded as the highest serum dilution that showed a positive reaction in ELISA.
[b]UCHT1-CRM9 ($2 \times 10^{-10}$) was incubated with different dilutions of serum for 30 min. The mixture was then added to cells as described under "Materials and Methods." Four replicates were performed for each sample. Data are presented as a mean value ± S.C. in percentage of the control counts. UCHT1-CRM9 inhibited protein synthesis to 2.0% of controls. The goat anti-DT serum couid be diluted to 1:10,000 and still completely inhibited the toxicity of UCHT1-CRM9.
[c]ND, not done Sera do not inhibit endocytosis of UCHT1-CRM9

The inhibitory effect of serum on UCHT1-CRM9 toxicity could be due to prevention of the immunotoxin binding to the cell surface or the endocytosis of UCHT1-CRM9 into the cell. Endocytosis assays were conducted using $^{125}$I-UCHT1-CRM9 to determine if either of these processes were affected by anti-DT antibodies present in sera. The results indicate that the presence of serum (goat anti-DT or human) reduces as much as 80% of the immunotoxin counts binding to the cell surface (Table 4). While this is a significant reduction in binding, limiting 90% of input immunotoxin (one log less UCHT1-CRM9) in toxicity assays reduces protein synthesis to <25% of controls (see FIG. 3).

In contrast, the inhibitory effect of serum containing anti-DT antibodies is 100%. Therefore the effect of the anti-DT antibodies is not all at the level of inhibition of binding to the cell surface. The pre-incubation of $^{125}$I-UCHT1-CRM9 for 2 hours on ice and subsequent washing at room temperature resulted in 18 to 25% of the total cell associated counts internalized (Table 4). After incubation for 30 minutes at 37° C., there is a doubling of internalized counts both with and without serum, indicating that the same percentage of labeled immunotoxin is endocytosed. The identical dilutions of serum were incubated with non-labeled UCHT1-CRM9 and used in protein synthesis inhibition assays. The results demonstrate that the ratio of immunotoxin to serum used was capable of completely inhibiting the toxicity (Table 4), although the endocytosis of UCHT1-CRM9 was not affected.

TABLE 4

Inhibition of UCHT1-CRM9 toxicity by serum does not correlate with inhibition of endocytosis.

| Serum Sample | Time (37° C.) | % Bound | % of Bound internalized | Protein Synthesis (% Control) |
|---|---|---|---|---|
| — | 0 | 100 | 23.6. | N.D.[a] |
| — | 30 | 100 | 58.8 | 3 ± 1 |
| Human | 0 | 20 | 18.1 | N.D.[a] |
| Human | 30 | 19 | 35.9 | 105 ± 5 |
| — | 0 | 100 | 25.3 | N.D.[a] |
| — | 30 | 100 | 54.0 | 3 ± 1 |
| Goat | 0 | 37 | 24.4 | N.D.[a] |
| Goat | 0 | 33 | 50.7 | 92 ± 14 |

[$^{125}$I]-UCHT1-CRM9 (2 × 10$^{-9}$ M) was incubated with medium or anti-DT serum (1:4 dilution of human sample 10010 or 1 1:1,000 dilution of goat serum; Table 3) for 30 minutes at room temperature. This mixture was added to Jurkat cells (1.5 × 106) for 2 hours on ice (final concentration of [$^{125}$I]-UCHT1-CRM9 was 1 × 10–10). The cells were then washed and endocytosis assays performed as described in Materials and Methods. The % Bound value represents the cell associated counts divided by the cell assocciated counts divided by the cell associated counts without serum. Non-labled UCHT1-CRM9 was incubated with the above dilutions of sera and the resulting mixture was used in protein synthesis inhibition assays. The results shown are representative of two independent assays.
n.d.: not done.

The inhibitory effect of anti-DT antibodies can be removed by adsorption

Figure 2A:
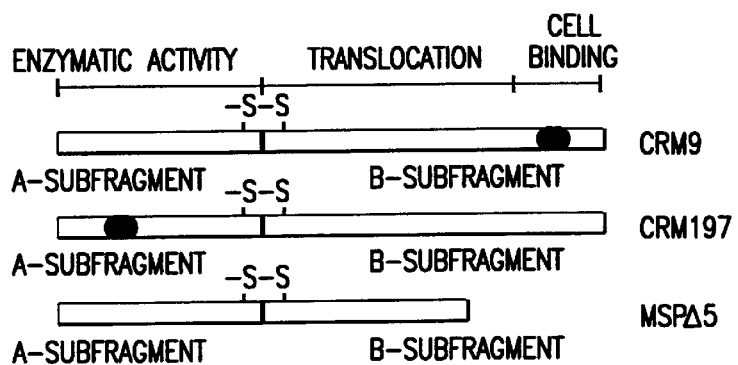
Figure 2B:
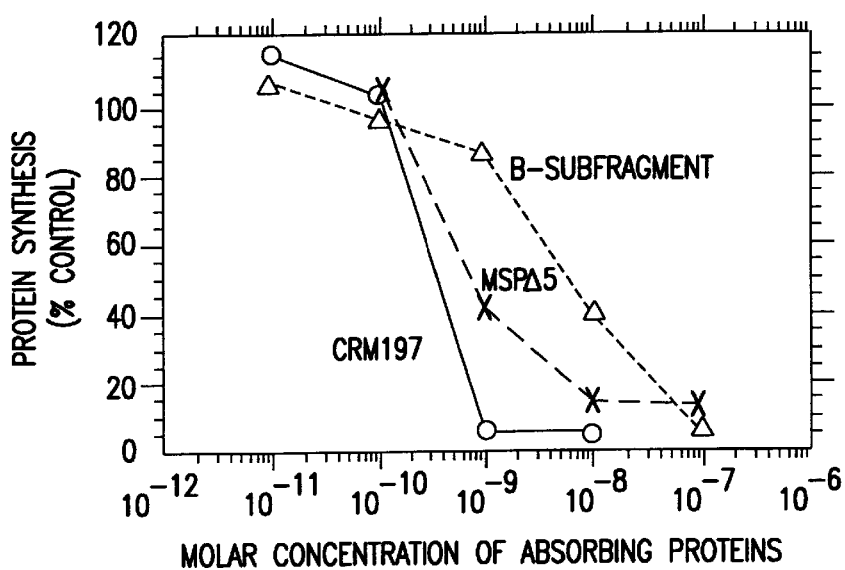
Figure 2C:
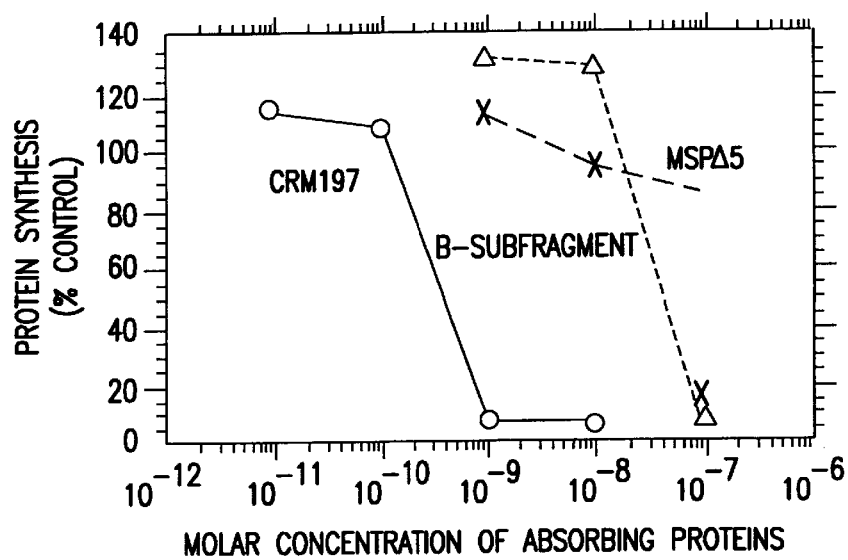

To prevent the inhibitory effect of serum as well as gain insight into the mechanism by which serum inhibits toxicity, experiments were designed to adsorb the protective anti-DT antibodies from the serum. The serum (a pool of all human sera with positive anti-DT ELISA or goat anti-DT) was pre-incubated for 30 minutes with increasing concentrations of CRM197 (an A-chain mutant of DT with no enzymatic activity), MSPΔ5 (a truncation mutant missing the last 150 amino acids) and the purified A- and B-subfragments of DT (FIG. 2A). The adsorbed serum was then incubated with UCHT1-CRM9 in protein synthesis inhibition assays. CRM197, the full length DT-like construct, was capable of completely adsorbing the protective antibodies from both goat (FIG. 2B) and pooled human serum (FIG. 2C). The B-subfragment of DT is also capable of complete adsorption, however ~100 fold more is required. The A-subfragment of DT had little or no effect on either serum, although the serum samples were demonstrated to contain antibodies reactive to both the A- and the B-subfragments by Western Blot analysis. Of interest were the results seen with MSPΔ5, the truncation mutant. Adsorption of goat serum with MSPΔ5 gave a dose dependent removal of the serum's protecting effect (FIG. 2B). However, this adsorption could not bring toxicity down to levels obtained when CRM197 or the B-subfragment was used.

In contrast to the results observed with the goat serum, MSPΔ5 had little effect on pooled human serum (FIG. 2C). These results suggest that the pre-existing anti-DT antibodies important for the protecting effect in human serum are mainly directed against the last 150 amino acids of DT.

sFv-DT390 is not inhibited by anti-DT antibodies present in human sera.

Figure 3A:
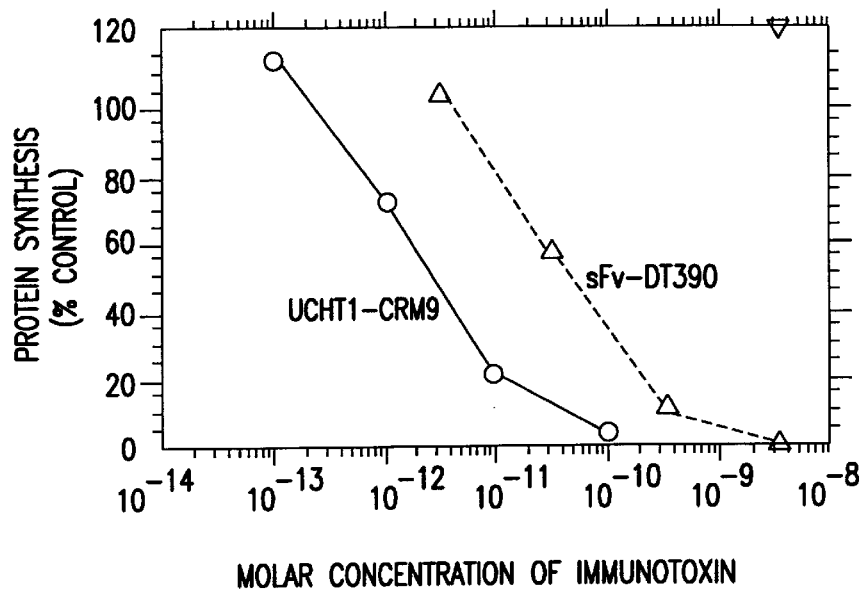
Figure 3B:
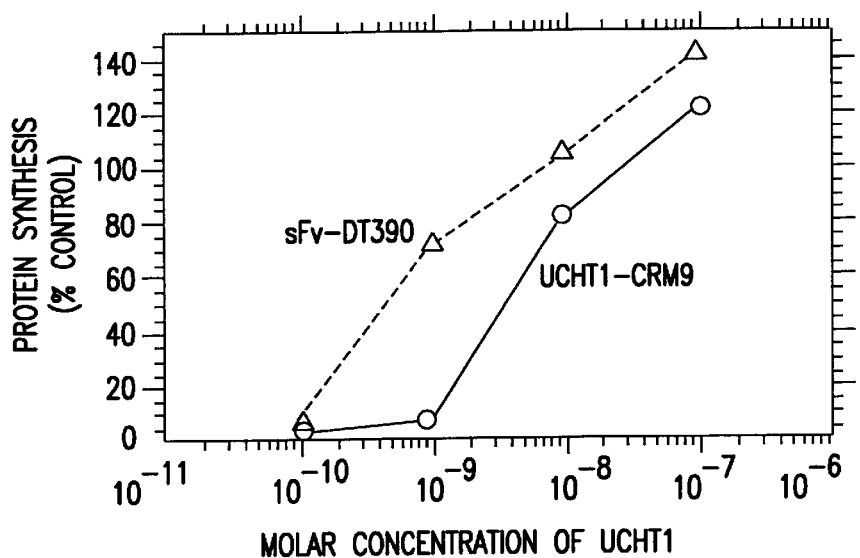

Having observed that the epitope(s) recognized by the antibodies important for protection lay in the C-terminal 150 amino acids, a single-chain immunotoxin was generated with the first 390 amino acids (out of 535) of DT. Position 390 was chosen for 2 reasons: first, the 3 dimensional structure of DT suggested that this position was an external point on the molecule away from the enzymatic domain (18), and second, fusion toxins have been generated with longer DT subfragments with no reports of serum effects (19). The DNA encoding the first 390 amino acids of DT was ligated to DNA encoding the anti-CD3εsFv ($V_L$ linked to $V_H$ using a (Gly$_3$Ser)$_4$ linker sequence). The predicted molecular weight for the fusion protein is 71,000 Daltons and has been confirmed by Western Blot analysis of both in vitro transcribed and translated protein as well as protein isolated from E. coli using goat anti-DT antibodies. The toxicity of sFv-DT390 protein, isolated from E. coli strain BL21/DE3, was compared to UCHT1-CRM9 in protein synthesis inhibition assays (FIG. 3A). The IC$_{50}$ (concentration required to inhibit protein synthesis to 50% of controls) of sFv-DT390 was 4.8×10$^{-11}$ M compared to 2.9×10$^{-12}$ M for UCHT1-CRM9, a 16-fold difference. To demonstrate the specificity of the sFv-DT390 construct, competition experiments were performed using increasing concentrations of UCHT1 antibody as competitor (FIG. 3B). The results showed that approximately ⅛ antibody is needed to compete the sFv-DT390 toxicity to 50% as compared to UCHT1-CRM9. The antibody was capable of totally competing toxicity of both constructs thereby showing their specificity. The immunotoxins were then subjected to protein synthesis assays in the presence of increasing dilutions of serum (Table 5).

UCHT1-CRM9 toxicity was completely inhibited with a 1:10 dilution of the human sera but at a 1:100 dilution toxicity was equivalent to controls without serum. In contrast, the sFv-DT390 immunotoxin is only partially inhibited with the 1:10 dilution of the human sera and the 1:100 dilution no effect on the toxicity. Both immunotoxins are completely inhibited by goat anti-DT serum (1:1,000 dilution). These results indicate that the sFv-DT390 immunotoxin partially evades the pre-existing anti-DT antibodies present in most human sera.

These results indicate that the pre-existing anti-DT antibodies present in human serum inhibit the toxicity of the immunotoxin UCHT1-CRM9. This inhibition of toxicity was also observed with goat anti-DT serum, however less goat serum was needed to completely inhibit toxicity. The experiments were designed in such a way to mimic the in vivo situation. The peak concentration of circulating immunotoxin currently being tested in animal models is 1×10$^{-9}$ M. The immunotoxin concentration incubated with the 1:10 dilution of human serum was 1×10$^{-10}$ M, thus approximating in vivo conditions. The inhibition of toxicity correlates with the serum antibody levels as determined by ELISA (Table 4), indicating that sera with higher anti-DT titers have a stronger inhibitory effect. Similarly, the goat anti-DT serum which gave the highest ELISA value could be diluted 10,000 times and still completely inhibited UCHT1-CRM9 toxicity. Since this correlation exists, there is no indication that any other component of the serum inhibits the toxicity of UCHT1-CRM9.

Furthermore, the data show that a titer of 1:100 dilution is necessary for an inhibition of the immunotoxin toxicity. A construct in which the first 486 amino acids of DT were fused to interleukin-2, $DAB_{486}IL-2$, was used in lymphoid malignancy patients. A partial response to $DAB_{486}IL-2$ was observed in several patients who had a anti-DT titer below 1:100 dilution prior to the treatment.

Intoxication of cells by immunotoxins can be subdivided into four general stages: 1) specific binding to the cell surface, 2) endocytosis into the cell, 3) translocation of enzymatic domain of the toxin out of the endosome and 4) enzymatic inactivation of the target molecule. The results presented indicate that, while the amount of immunotoxin reaching the cell surface is lower in the presence of serum, the same percentage of bound immunotoxin is endocytosed. Taking into account the reduced amount of immunotoxin bound to the cell, the amount of endocytosed immunotoxin should intoxicate the cells to below 25% of controls. However, the immunotoxin had no effect on protein synthesis in the presence of serum containing anti-DT antibodies. Since the A-subfragment of DT could not adsorb the protective effect of serum while the B-subfragment could, the effect of serum is not likely to be at the level of inhibiting enzymatic activity of the toxin. Therefore, the anti-DT antibodies probably affect the translocation of the A-subfragment into the cytosol.

CRM197, B-subfragment, and MSPΔ5 could adsorb the protecting anti-DT antibodies from the goat and rhesus monkey sera. However, among the 3 DT mutants, MSPΔ5 could not prevent the UCHT1-CRM9 toxicity in the presence of the human sera, showing a difference in the anti-DT antibody repertoire among humans, goat and rhesus monkeys. This difference does not seem to be due to immunization routes, because monkeys used in the present study were not immunized for DT and presumably acquire the antibodies after a natural infection with toxigenic strains of C. diphtheriae. There have been reports showing that rhesus monkeys and humans shared a similar antibody repertoire (21), but the present results suggest that the effect of antibodies from the host for whom immunotoxin treatment is intended should be useful.

To overcome the blocking effect of the pre-existing anti-DT antibodies in human sera, there are basically two pathways existing. One is to neutralize the antibodies with non-toxic DT mutants, and the other is to modify the DT structure used for making immunotoxin (3). The antibody neutralization pathway has been tested in monkey studies of FN18-CRM9 treatment as described above.

The present results showed that although antibodies against both A- and B-subfragments existed in human sera, MSP5 could not neutralize the pre-existing protective anti-DT antibodies, and therefore could not prevent the inhibition of the cytotoxicity of UCHT1-CRM9. However, it did block the inhibitory effect of the goat and monkey sera. This prompted the construction of the present recombinant immunotoxin, sFv-DT390. The $IC_{50}$ of sFv-DT390 is $4.8 \times 10^{-11}$ M, 1/16 as potent as UCHT1-CRM9. Like many other single-chain constructs, sFv-DT390 is monovalent as compared to immunotoxins generated with full length, bivalent antibodies. The reduced toxicity in sFv-DT390 could be explained primarily on this affinity difference. Immunotoxins generated with purified F(ab)' fragments of antibodies also show an in vitro loss in toxicity (generally a 1.5 log difference) when compared to their counterparts generated with full length antibodies (22). The toxicity of sFv-DT390 is comparable to that reported for DAB486IL-2 (23). From the present data some advantages of sFv-DT390 are expected. First, sFv-DT390 is is only 1/3 of the molecular weight of UCHT1-CRM9. The molar concentration of sFv-DT390 will be 3 times higher than that of UCHT1-CRM9 if the same amount is given (for example, 0.2 mg/kg). Therefore, their difference in potency could be reduced to approximately 5 times. Second, in an in vitro experiment (Table 5), the same molar concentration of sFv-DT390 and UCHT1-CRM9 was used for serum inhibition test, although the former is only 1/16 potent compared to the latter. The pre-existing anti-DT antibodies in human sera could only partially block the toxicity of sFv-DT390 while the effect of UCHT1-CRM9 was completely blocked. Thus, sFv-DT390 is expected to bypass the anti-DT antibodies in in vivo situations while UCHT1-CRM9 cannot. Third, sFv-DT390 contains only the variable region of UCHT1, and is expected to have less immunogenicity in human anti-mouse antibody (HAMA) responses than the native murine antibody UCHT1. Finally, the production cost of sFv-DT390 is much lower than that of UCHT1-CRM9. Based on these reasons, sFv-DT390, or others with similar properties, are expected to be useful in the treatment of T-cell mediated diseases in humans, especially in anti-DT positive individuals and in patients who need repeated treatments. To obtain evidence supporting this assumption, it is only necessary to construct a rhesus monkey analog of sFv-DT390, and test it in monkey models as described in previous examples.

TABLE 5

Anti-DT antibodies present in human sera have reduced effect on sFv-DT390 toxicity.

| | | Protein synthesis (% Control) | | | | | |
|---|---|---|---|---|---|---|---|
| | ELISA value | UchT1CRM9 | | | sFv-DT390 | | |
| Serum Sample | (±S.D.) | 1:10 | $1:10^2$ | $1:10^3$ | 1:10 | $1:10^2$ | $1:10^3$ |
| 10012 | 0.491 ± 0.025 | 119 ± 24 | 8 ± 2 | $ND^a$ | 47 ± 9 | 21 ± 8 | ND |
| Pooled | 0.331 ± 0.015 | 108 ± 17 | 7 ± 1 | $ND^a$ | 49 ± 7 | 16 ± 7 | ND |
| Goat | 1.450 ± 0.013 | ND | ND | 94 ± 21 | ND | ND | 8 ± 11 |

TABLE 5-continued

Anti-DT antibodies present in human sera have reduced effect on sFv-DT390 toxicity.

| | | Protein synthesis (% Control) | | | | | |
|---|---|---|---|---|---|---|---|
| | ELISA value | UchT1CRM9 | | | sFv-DT390 | | |
| Serum Sample | (±S.D.) | 1:10 | $1:10^2$ | $1:10^3$ | 1:10 | $1:10^2$ | $1:10^3$ |

[a]Not done
UCHT1CRM9 or sFv-DT390 ($2 \times 10^{-9}$ M) was incubated with the indicated dilutions of serum for 30 min. The mixture was then added to cells as described under "Materials and Methods." The final concentration of immunotoxin on cells was $1 \times 10^{-10}$ M. Four replicates were performed for each sample. Data are presented as a mean value ± S.D. in percentage of the control counts. UCHT1-CRM9 inhibited protein synthesis to 5% of controls while the sFv-DT390 inhibited protein synthesis to 18% of controls. The ELISA value was determined using a 1:100 dilution of serum. The results are representative of two independent experiments.

EXAMPLE 10

Expression and Characterization of A Divalent Chimeric Anti-human CD3 Single Chain Antibody Murine anti-CD3 monoclonal antibodies (mAbs) are used in clinical practice for immunosuppression. However, there are two major drawbacks of this treatment: the associated cytokine release syndrome and human anti-mouse antibody response. To overcome these side effects, a chimeric anti-human CD3 single chain antibody, scUCHT1 was generated. It is an IgM variant of the UCHT1 described in Example 9. scUCHT1 consists of the light and heavy variable chain binding domains of UCHT1 and a human IgM Fc region ($CH_2$ to $CH_4$). The method used was reported by Shu et al. [37] and is further described below. The following data show that the engineered chimeric anti-CD3 single chain antibody (scUCHT1) will be useful in clinical immunosuppressive treatment.

Oligonucleotide primers and DNA amplification

P3 have a 25 bp complementary overlap and each encoded a part of a linker peptide $(Gly_4Ser)_3$. The single chain variable fragment ($V_L$-linker-$V_H$) was created by recombinant amplification of $V_L$ and $V_H$ using primers P1 and P4. A mouse kappa chain signal sequence was added at the $V_L$ 5'-end by PCR, first with primers SP2 and P4, and then with primers SP1 and P4. The human IgM Fc region ($CH_2$ to $CH_4$) was amplified from the plasmid pBlue-huIgM (kindly provided by Dr. S. V. S. Kashmiri, National Cancer Institute, Bethesda. This gene fragment was about 1.8 kb. The $V_L$-linker-$V_H$-CH2 region which is important for antigen recognition was confirmed by sequence analysis. Finally, the single chain variable fragment and the human IgM Fc region were cloned into plasmid pBK/CMV (Stratagene, La Jolla, Calif., USA). Using the generated pBK/scUCHT1 plasmid as template, an in vitro transcription-translation assay yielded a product of 75 kDa, the expected size.

TABLE 6

Sequences of oligonucleotide primers used for PCR amplification

| Primers | Sequences | RE sites |
|---|---|---|
| | 5'                                                                                    3' | |
| P1(UCHT1 VL5) (SEQ ID NO. 7) | GACATCCAGATACCCAGACC | |
| P2(UCHT1 VL3) (SEQ ID NO. 8) | CCTCCCGAGCCACCGCCTCCGCTGCCTCCGCCTCCTTTTATCTCCAGCTTG(T)GTC(G)CC | |
| P3(UCHT1 VH5) (SEQ ID NO. 9) | GCAGCGGAGGCGGTGGCTCGGGAGGGGGAGGCTCGGAGGTGCAGCTTCAGCAGTCT | |
| P4(UCHT1 VH3) (SEQ ID NO. 10) | GC<u>AAGCTT</u>GAAGACTGTGAGAGTGTGCCTTG | Hind III |
| P5(HuIgM-CH2) (SEQ ID NO. 11) | GTCTCTTCA<u>AAGCTT</u>ATTGCC(T)GAGCTGCCTCCCAAA | Hind III |
| P6(HuIgM-CH4) (SEQ ID NO. 12) | GAC<u>TCTAGA</u>TCAGTAGCAGGTGCCAGCTGTGT | Xba I |
| SP1 (SEQ ID NO. 13) | CG<u>GTCGAC</u>ACCATGGAGACAGACACACTCCTGTTATGGGTACTGCTGCTCTGGGTTCCA | Sal I |
| SP2 (SEQ ID NO. 14) | GTACTGCTGCTCTGGGTTCCAGGTTCCACTGGGGACATCCAGATGACCCAG | |

Figure 4:
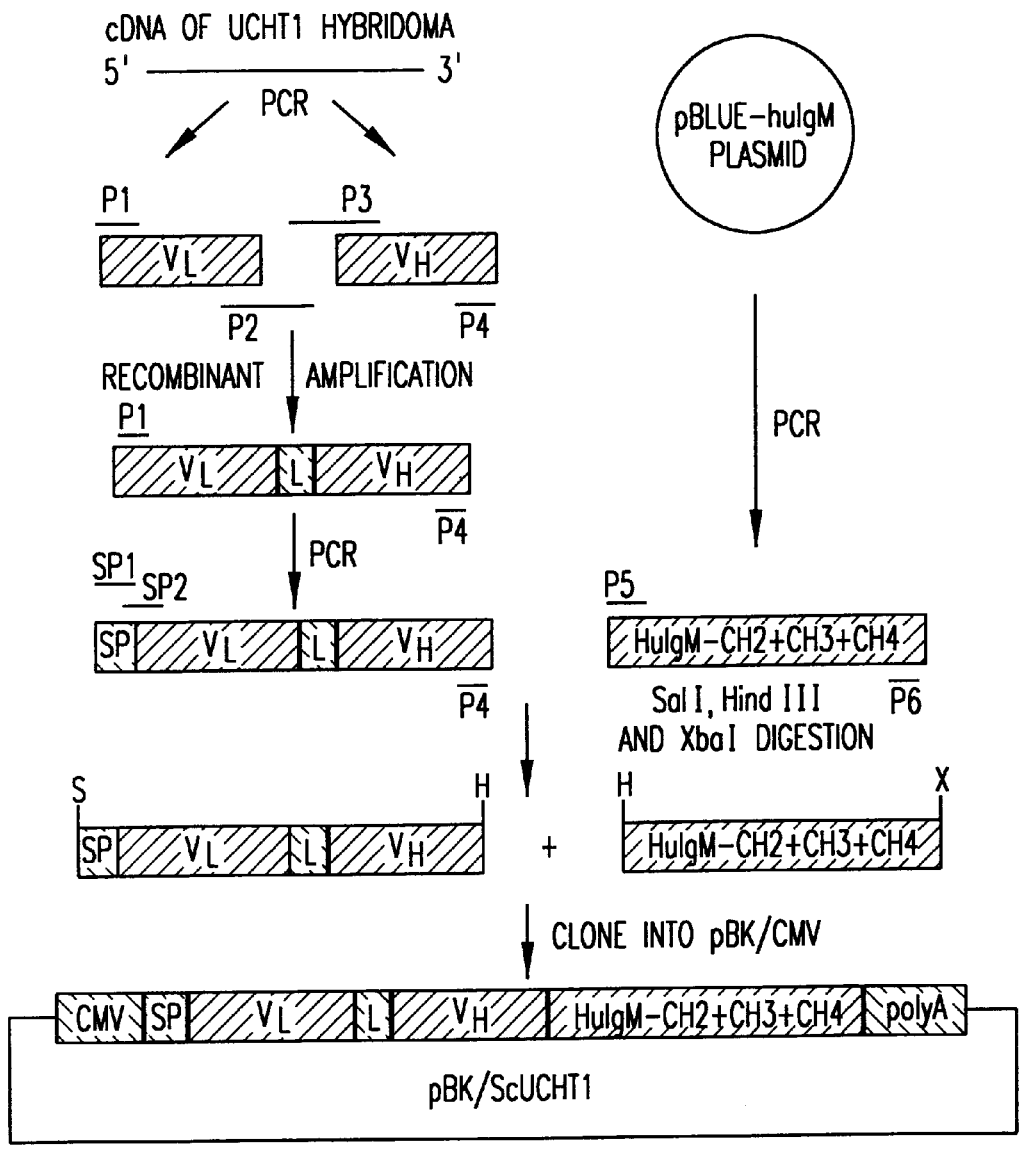

Primers used for the antibody engineering are listed in Table 6, and the primer sequences are based on published data [13]. The procedures of cloning scUCHT1 is schematically depicted in FIG. 4. mRNA isolated from UCHT1 hybridoma cells (provided by Dr. P. C. Beverley, Imperial Cancer Research Fund, London was reverse transcribed into cDNA. The $V_L$ and $V_H$ regions of UCHT1 were amplified with polymerase chain reaction (PCR) from the cDNA using primer pairs P1, P2 and P3, P4 respectively. Primers P2 and Expression in COS-7 and SP2/0 cells The gene fragment encoding scUCHT1 was then cloned into an expression vector pLNCX [36]. The scUCHT1 gene construct was introduced into COS-7 cells with a calcium-phosphate method [32], and introduced into SP2/0 myeloma cells by electroporation [33]. Cells transfected were selected with 500 μg/ml G418 (GIBCO/BRL, Gaithersburg, Md., USA) in DMEM medium. The drug resistant transfectants were screened for scUCHT1 secretion by an anti-human IgM ELISA technique. Transfectants secreting scUCHT1 were cloned by limiting dilution.

Figure 5:
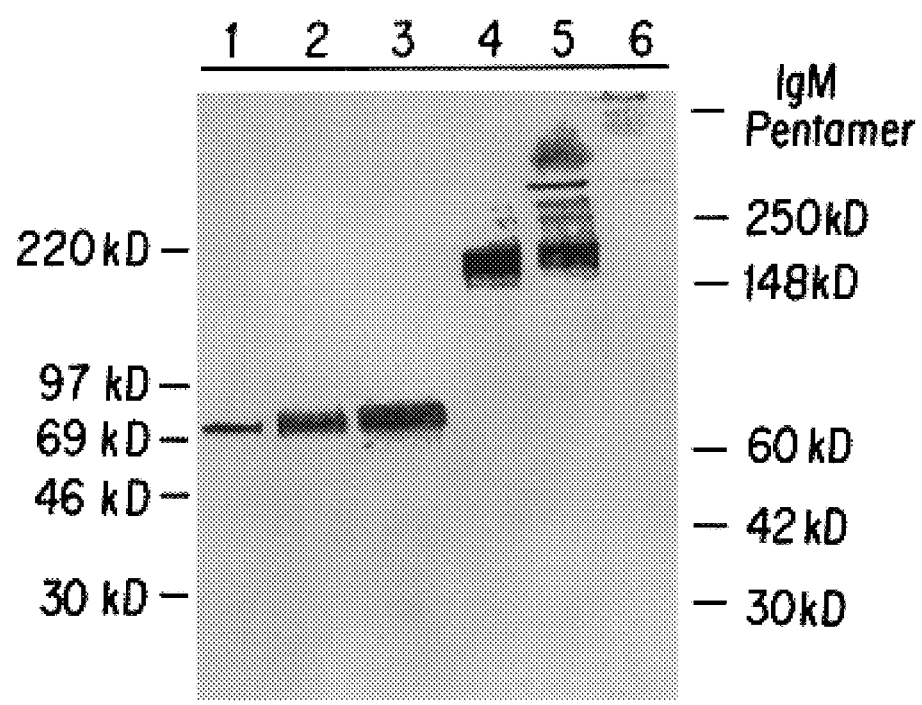

Two stable clones, COS-4C10 and SP2/0-7C8, which could produce about 0.5 mg/ml scUCHT1 in culture medium, were selected for further evaluation. The culture supernatant of COS-4C10 and SP2/0-7C8 cells was analyzed by immunoblotting using anti-human IgM antibody (FIG. 5). Human IgM antibody was included as a control in the analysis. Under reducing conditions, scUCHT1 produced by COS-7 and SP2/0 cells had a similar electrophoretic mobility to that of the control human IgM heavy chain (75 kDa). Under non-reducing conditions, scUCHT1 from COS-7 cells appeared as a single band of approximately 150 kDa, which was thought to be a homodimer of the single chain antibody. SP2/0 cells mainly produced a protein of similar size with some higher molecular weight products.

In constructing scUCHT1, the domain orientation of sFv, $V_H$-$V_L$, which Shu et al. used to $V_L$-$V_H$ orientation, was changed so that the heavy chain constant domains were linked to the $V_H$ domain. In mammalian cells, secretion of immunoglobulin molecules is mediated by light chain, and free light chain is readily secreted [38]. However, free heavy chain is generally not secreted [39]. In a bacterial expression system, the yield of secreted sFv with a $V_L$-$V_H$ domain orientation was about 20-fold more than that obtained with a $V_H$-$V_L$ domain orientation [40]. It was reasoned that $V_L$ at the $NH_2$-terminal position and $V_H$ linked to heavy chain constant region in scUCHT1 construct might enhance the secretion of this immunoglobulin-like molecule in mammalian cells. In fact scUCHT1 was efficiently produced by both COS-7 and SP2/0 cells. Hollow fiber culture should increase its production. Moreover, scUCHT1, the IgM-like molecule, has a secretory tailpiece with a penultimate cysteine (Cys 575) which is involved in polymerization and also provides retention and degradation of IgM monomers [41–43]. Replacing the Cys 575 with serine might also greatly improve the yield.

scUCHT1 secreted from COS-7 cells was shown to be a divalent form by immunoblotting, suggesting a disulfide bond linkage of two monovalent molecules. The disulfide bond is likely situated between the CH2 and CH3 regions, where the Cys 337-Cys 337 disulfide bond is thought to exist. Cys 337 is believed to be sufficient for assembly of IgM monomers, and was neither sufficient nor necessary for formation of polymers. However, Cys 575 was necessary for assembly of IgM polymers, and Cys 414 was not required for formation of IgM monomers or polymers [44]. This divalent form of the single chain antibody should increase its binding affinity. While scUCHT1 produced from SP2/0 cells was mainly in the divalent form, a small fraction of the antibody had a higher molecular weight, nearly comparable to that of the human IgM pentamer, the natural form of secreted human IgM.

Western blotting analysis of scUCHT1 scUCHT1 was precipitated from the culture supernatant using goat anti-human IgM-Agarose (Sigma, St. Louis, Mo., USA), and separated on 4–20% SDS-PAGE gradient gel under reducing and non-reducing conditions. The separated proteins were transferred to ProBlottTM membrane (Applied Biosystems, Foster City, Calif., USA) by electroblotting at 50 volts for 1 hour. The membrane was blocked and incubated with alkaline phosphatase labeled goat anti-human IgM antibody (PIERCE, Rockford, Ill., USA) following the manufacturer's instruction. Color development was carried out with substrate NBT/BCIP (PIERCE).

Purification of scUCHT1

Culture supernatant was mixed with anti-human IgM-Agarose, and incubated at 40° C. with shaking overnight, and then the mixture was transferred to a column. The column was washed with washing buffer (0.01 M Na-phosphate, pH 7.2, 0.5 M NaCl) until the OD280 of flow-through was <0.01. scUCHT1 was eluted with elution buffer (0.1 M glycine, pH 2.4, and 0.15 M NaCl). The fractions were neutralized with 1 M Na-phosphate (pH 8.0) immediately, and then concentrated and dialyzed against PBS.

Competitive binding assay

Figure 6:
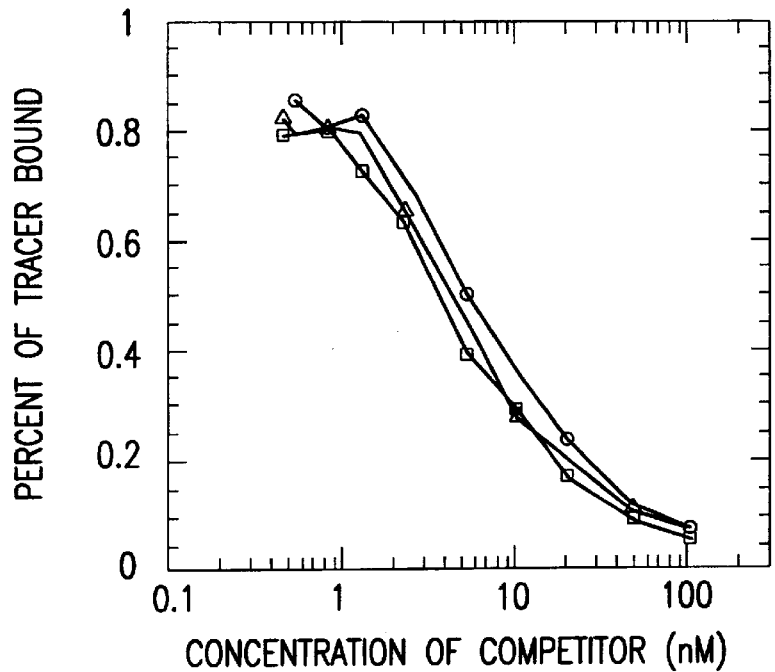

The parental antibody UCHT1 was iodinated using Bolton-Hunter Reagent (NEN, Wilmington, Del., USA) as described previously [34]. The $^{125}$I-labeled UCHT1 was used as tracer and diluted with DMEM medium to 0.3–0.6 nM. UCHT1 and the purified scUCHT1 from COS-7 and SP2/0 transfectant cells were used as competitors. Human CD3 expressing Jurkat cells were suspended in DMEM medium ($2 \times 10^7$/ml). 50 μl of such cell suspension ($1 \times 10^6$) was incubated with 50 μl diluted tracer and 50 ml diluted competitors on ice for 2 hours. Afterwards, cells were pelleted, and counted in a gamma counter. Results were expressed as a percentage of the $^{125}$I-UCHT1 bound to cells in the absence of competitors (FIG. 6).

scUCHT1 from both COS-7 and SP2/0 cells could specifically inhibit the binding of $^{125}$I-UCHT1 to Jurkat cells in a dose dependent way. As the concentration of the competitors (UCHT1, scUCHT1 from COS-7 and SP2/0 cells) increased from 1 to 100 nM, the tracer ($^{125}$I iodinated UCHT1) bound to Jurkat cells decreased from 80% to nearly 0%. No significant difference was observed among the affinity curves of UCHT1 and scUCHT1 from COS-7 and SP2/0 cells. This indicates that the engineered antibody scUCHT1 has nearly the same affinity as UCHT1. Moreover, scUCHT1 contains human IgM constant region, and is expected be less immunogenic than UCHT1. The degree of its immunogenicity might vary due to the murine variable region of scUCHT1. Humanized variable regions by CDR-grafting or human variable regions can be used to further reduce its immunogenicity [31].

T-cell proliferation assay

Figure 7:
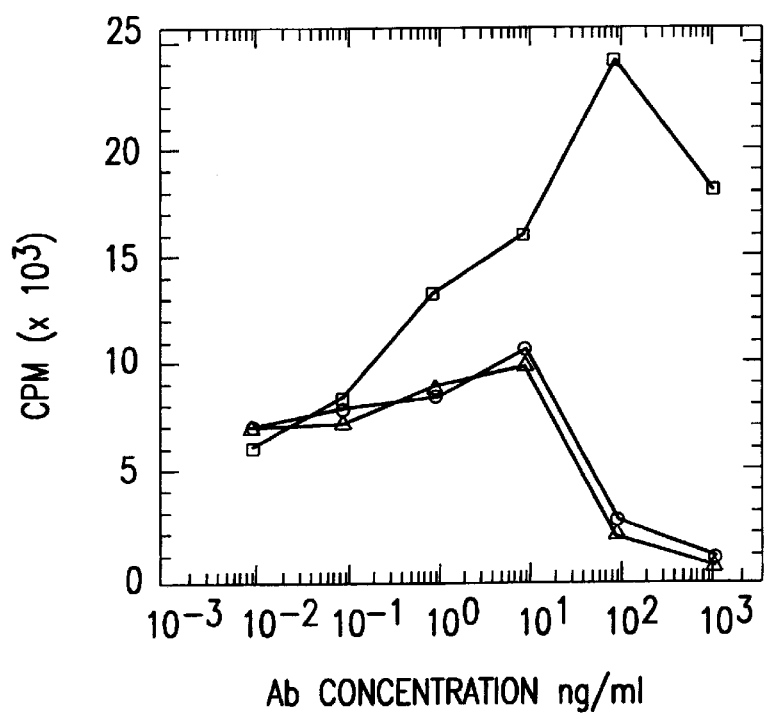

T-cell proliferation in response to UCHT1 and scUCHT1 was tested on human PBMCs from a healthy donor (FIG. 7). Human peripheral blood mononuclear cells (PBMCS) were isolated from blood of a healthy adult by density centrifuge over Ficoll-Hypaque gradient [34]. The PBMCs were resuspended in RPMI 1640 supplemented with 10% FCS and aliquoted to 96-well U-bottom plates at $5 \times 10^4$ cells/well. Increasing amounts of anti-CD3 antibodies (UCHT1, scUCHT1) were added. After 72 hours of culture at 37° C. in a humidified atmosphere containing 5% $CO_2$, 1 μCi [$^3$H]thymidine (NEN) was added to each well. 16 hours later, cells were harvested and [$^3$H]thymidine incorporation was counted in a liquid scintillation counter.

The parental antibody UCHT1 started to induce proliferation at 0.1 ng/ml, and peaked at 100 ng/ml. A small drop in CPM was observed as the concentration increased to 1,000 ng/ml. However, [$^3$H]thymidine incorporation in PBMCs incubated with scUCHT1 was only slightly increased in the range of 0.1–10 ng/ml, and when the concentration was higher than 10 ng/ml, the incorporated counts decreased and were close to 0 counts at 1,000 ng/ml.

Measurement of TNF-α and IFN-γ

TNF-α and IFN-γ productions of human PBMCs induced by UCHT1 and scUCHT1 were measured with ELISA. $4 \times 10^5$ PBMCs were cultured with serial dilutions of anti-CD3 antibodies (UCHT1, scUCHT1) in 96-well flat-bottom plates in RPMI 1640 supplemented with 10% FCS. Supernatant was collected at 36 hours for TNF-α and 72 hours for IFN-γ after the start of the culture [35]. TNF-α and IFN-γ were measured with ELISA kits (Endogen Inc. Cambridge, Mass., USA) following the manufacturer's instruction.

Figure 8A:
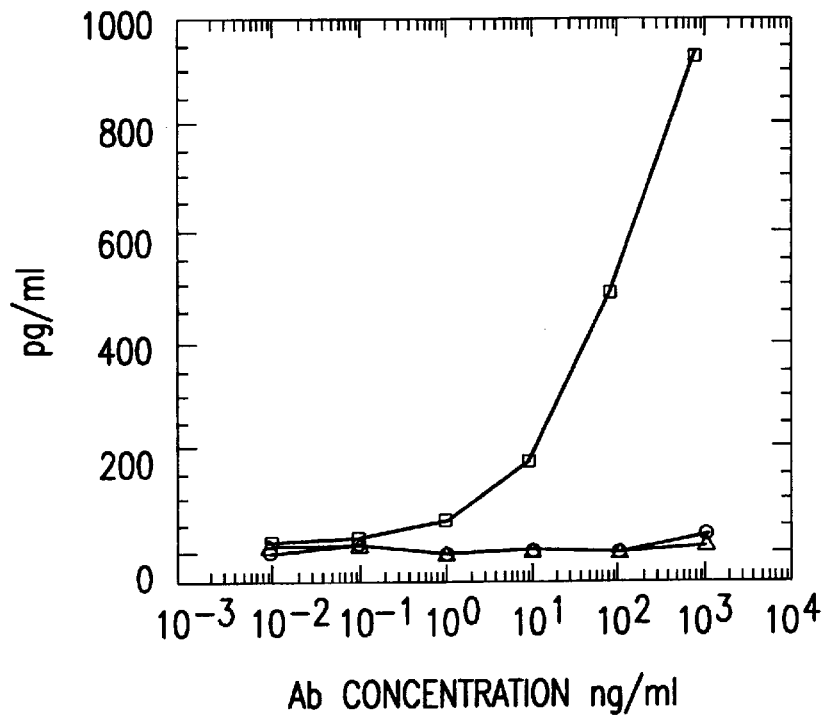
FIG. 8a shows that UCHT1 and scUCHT1 had little effect on TNF-α secretion, and. scUCHT1 from both COS-7 (Δ) and SP2/0 (o) cells and UCHT1 (□) were added to cultures of human blood mononuclear cells. Culture supernatant was harvested and used for ELISA determination of TNF-α and IFN-γ as described in materials and methods.
Figure 8B:
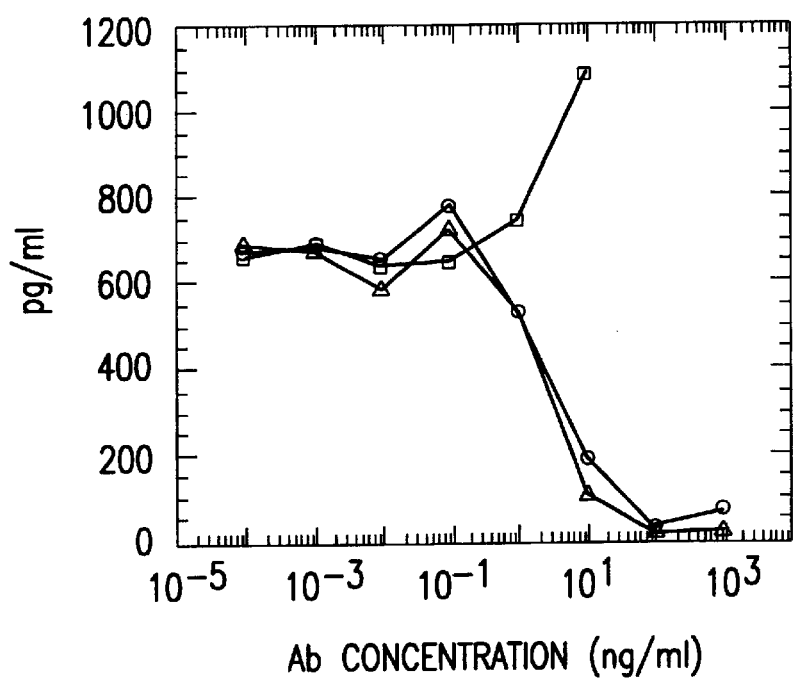
FIG. 8b shows that UCHT1 and scUCHT1 inhibited the basal production of IFN-γ. scUCHT1 from both COS-7 (Δ) and SP2/0 (o) cells and UCHT1 (□) were added to cultures of human blood mononuclear cells. Culture supernatant was harvested and used for ELISA determination of TNF-α and IFN-γ as described in materials and methods.

The native antibody UCHT1 induced production of both TNF-α and IFN-γ in a dose dependent way (FIG. 8a and 8b). Higher concentration of UCHT1 induced higher production of TNF-α and IFN-γ. On the contrary, scUCHT1 did not induce secretion of TNF-α at any concentration (FIG. 8a), and inhibited IFN-γ production when its concentration was higher than 0.1 ng/ml (FIG. 8b). At the time of supernatant harvesting, the PBMCs cultured with UCHT1 and scUCHT1 were also checked with trypan blue exclusion test. Cells were shown to be alive in both situations. In TNF-α and IFN-γ ELISA assays, an unrelated human IgM was included and it did not affect the TNF-a and IFN-g production.

Anti-CD3 mAbs can induce T cell activation and proliferation both in in vitro and in vivo situations [45]. Crossing-linking of anti-CD3 antibody between T cells and FcR expressing cells is an essential step in this process [46]. T cell activation therefore reflects an efficient interaction of the mAb with a human FcR. Previous data of in vitro study indicated that T cell activation resulted in increased production of TNF-α, IFN-γ, and IL-2 [24]. Human IgG Fc receptors (FcγR I, FcγR II, FcγR III) are distributed on human monocytes, T, B lymphocytes, and NK cells [47]. FcγR I and FcγR II can recognize both mouse and human IgG. In accordance with the above observation, UCHT1 was potent in induction of T cell proliferation and TNF-α and IFN-γ release. Human IgM Fc receptor (FcμR) was reported to be present mainly on a small fraction of B lymphocytes, NK cells, and possibly a helper subset of T lymphocytes [47, 48]. Pentamer form of IgM and an intact CH₃ domain are required for optimal binding to FcμR. Monomeric or dimeric subunits of IgM are less efficient in binding to FcμR [49, 50]. Cross-linking of IgM to FcμR on T cells inhibited the mitogen-induced T cell proliferation, and FcμR may function as a negative signal transducing molecule [51, 52].

Therefore, it can specifically bind to human CD3 molecule and FcμR. It is conceivable that scUCHT1 can cross-link human B and T cells, and possibly T and T cells. In an in vitro assay, scUCHT1 from both COS-7 and SP2/0 cells had little effect in the T cell proliferation assay at low concentrations (below 10 ng/ml), and became inhibitory as the concentration increased. In accordance with these results, scUCHT1 did not induce TNF-α production and even inhibited the basal yield of IFN-γ.

The present chimeric anti-CD3 single chain antibody scUCHT1 possesses high human CD3 binding specificity and affinity, and does not induce T cell proliferation and cytokine release. Moreover, it has a human IgM Fc fragment, which should decrease the possibility of inducing human anti-mouse antibody response. Thus, scUCHT1 can be used for clinical immunosuppressive treatment.

EXAMPLE 11

Cloning the Full-length of DT Gene for the Construction of DTM2

Corynebacteriophage beta (*C. diphtheriae*) tox 228 gene sequence was from genebank. (*Science* 221, 885–858, 1983). The sequence is 2220 bp. There are 300 bp of 5' untranslated region (1 to 300) including the promoter sequence around (−180 to −10), 1682 of coding region (301–1983) including signal peptide (301 to 376), A chain (377 to 955) and B chain (956 to 1983), and 3' untranslated region (1984 to 2220).

The full-length DT was amplified in two fragments. The pelB leader sequence (ATG AAA TAC CTA TTG CCT ACG GCA GCC GCT GGA TTG TTA TTA CTGCGCT GCC CAA CCA GCG ATG GCC 3') SEQ ID NO:1) was added to the 5' end of the DT coding sequence to all the constructs during polymerase chain reaction by primer EcosignalDT-1 and EcosignalDT-2. The upstream fragment of 311 bp (from position 301 to 546 bp) was amplified by oligo EcosignalDT-2 and p546R with CRM9 DNA as a template and the downstream fragment of 1471 bp was amplified by p514S and p1983R with the DTM1 DNA as template. Then, the combined PCR product of full-lenth DT was amplified with primer EcosignalDT-1 and p1983R. As a result, the amplified DT coding sequence (position 376 to 1983 bp) acquired the pelB leader sequence added to the 5' end and contains the two mutant sites [(508 Ser to Phe) and (525 Ser to Phe)] as DTM1 does.

Primers:

EcosignalDT-1 5' ATG AAA TAC CTATTG CCT ACG GCA GCC GCT GGA TTG TTA TTA CTC GCT GCC CAA 3' (SEQ ID NO:2)

EcosignalDT-2 5' GGA TTG TTA TTA CTC GCT GCC CAA CAA GCG ATG GCCGGC GCT GAT GATGTT GTT GAT TC 3' (SEQ ID NO:3) p546R: 5' CGGTAC-TATAAAACTCTTTCCAATCATCGTC 3' (SEQ ID NO:4) p514S: 5' GACGATGATTGGAAAGAGTTT-TATAGTACCG 3' (SEQ ID NO:5) p1983R: 5'AGATCTGTCGA/ CTCATCAGCTTTTGATTTCAAAAAATAGCG 3' (SEQ ID NO:6).

A mutant residue was introduced at position 52. The glycine (GGG) at position 52 wild type DT was substituted by glutamic acid (GAG). The two primers p546R and p514S carried the mutant codon (GGG to GAG). The PCR products of these two primers contained the substituted codon (GAG) instead of codon GGG. The jointed double stranded DNA of the two fragments (1683 bp) were cloned into pET 17b by restriction site NdeI and BamHI.

The data show that anti-human blocking antibodies are specifically directed at the toxin C-terminus. Although a specific sequence derived from the UCHT1 VLVH regions is described, anyone skilled in the art could make sequence variations in VLVH domains which can be designed to increase the affinity of the sc-anti-CD3-antibody conferring a more favorable therapeutic ratio to fusion immunotoxins using this derivative. Such modifications are within the scope of the present teaching. The disadvantage of the monovalent antibody VLVH construct, is that it has a lower affinity for T cells compared to the chemically coupled conjugate which utilizes a divalent antibody.

These are believed to be the first instances of a sc anti-CD3 antibodies. IgM was chosen since very few B cells or macrophages contain IgM Fc receptors. (Binding of immunotoxin to cells other than T cells reduces the specificity of the anti-T cell immunotoxin and this situation is purposefully avoided). However, using a bacterial expression system no carbohydrate is attached to the antibody which also eliminates Fc receptor binding. Thus, substituting other human IgG constant domains would be a routine modification and should be claimed.

Figure 9:
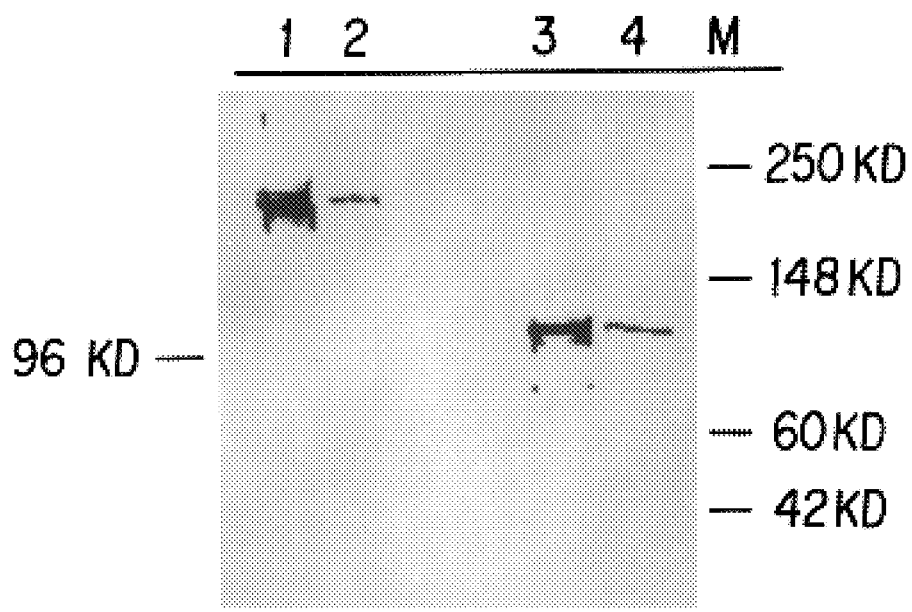
FIG. 9 is a western blot showing the secreted scUCHT1 immunotoxin.
Figure 10:
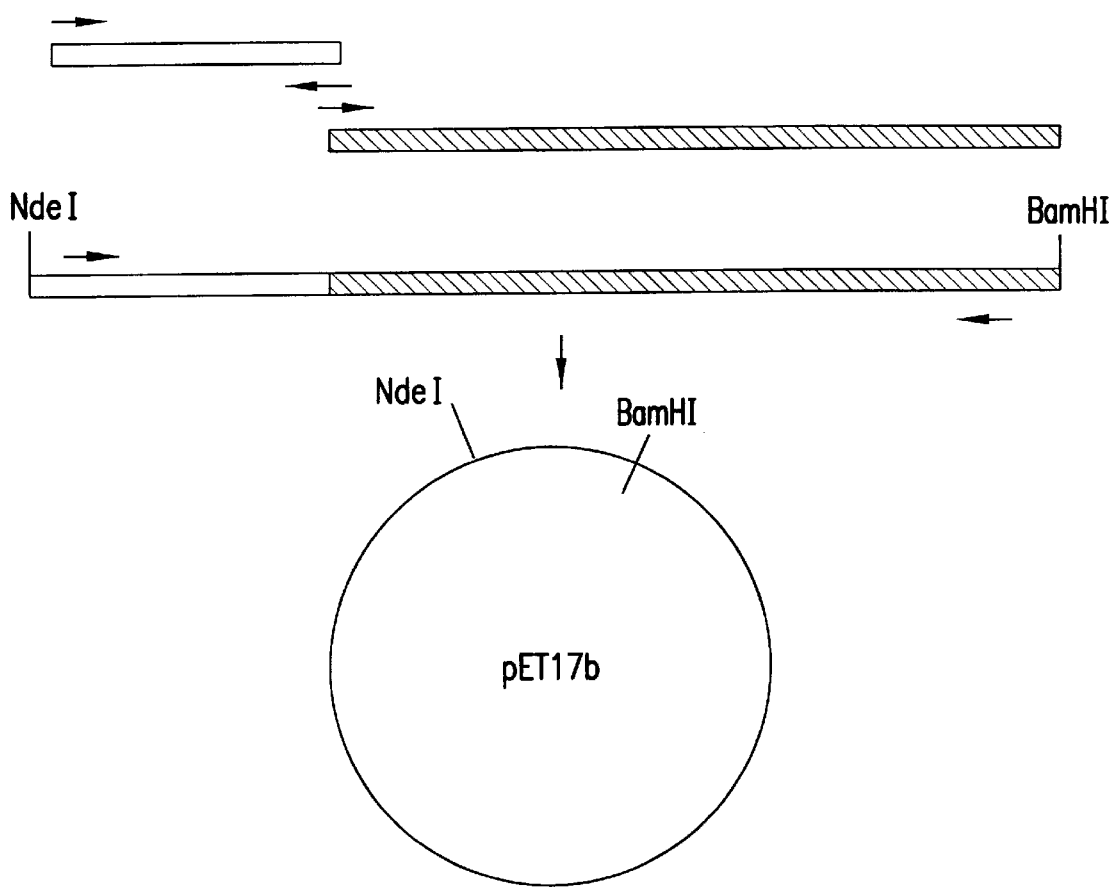
FIG. 10 shows a PCR amplification scheme.
Figure 11:
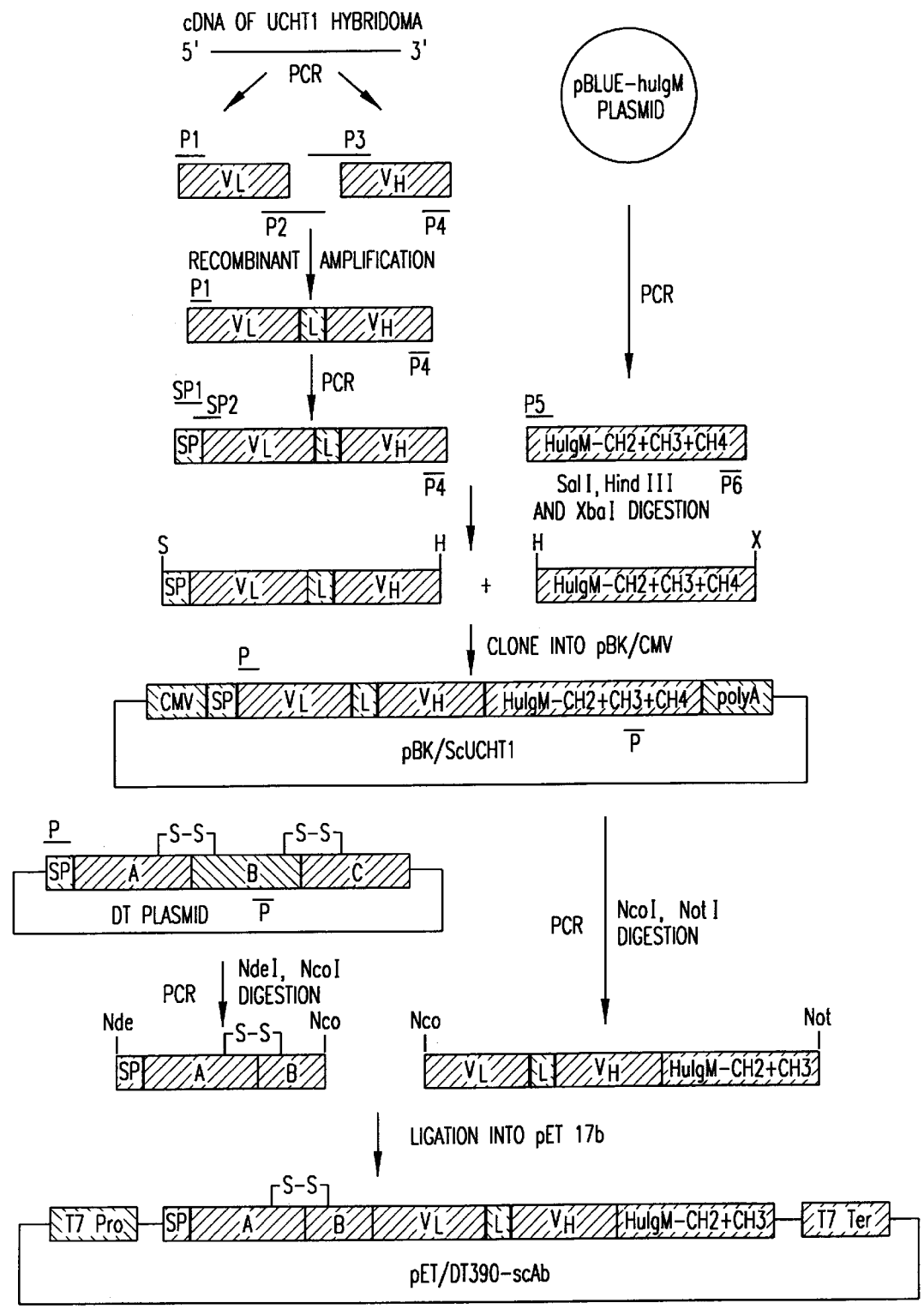
FIG. 11 shows one clone expressing the divalent immunotoxin fusion protein shown in FIG. 13.
Figure 12:
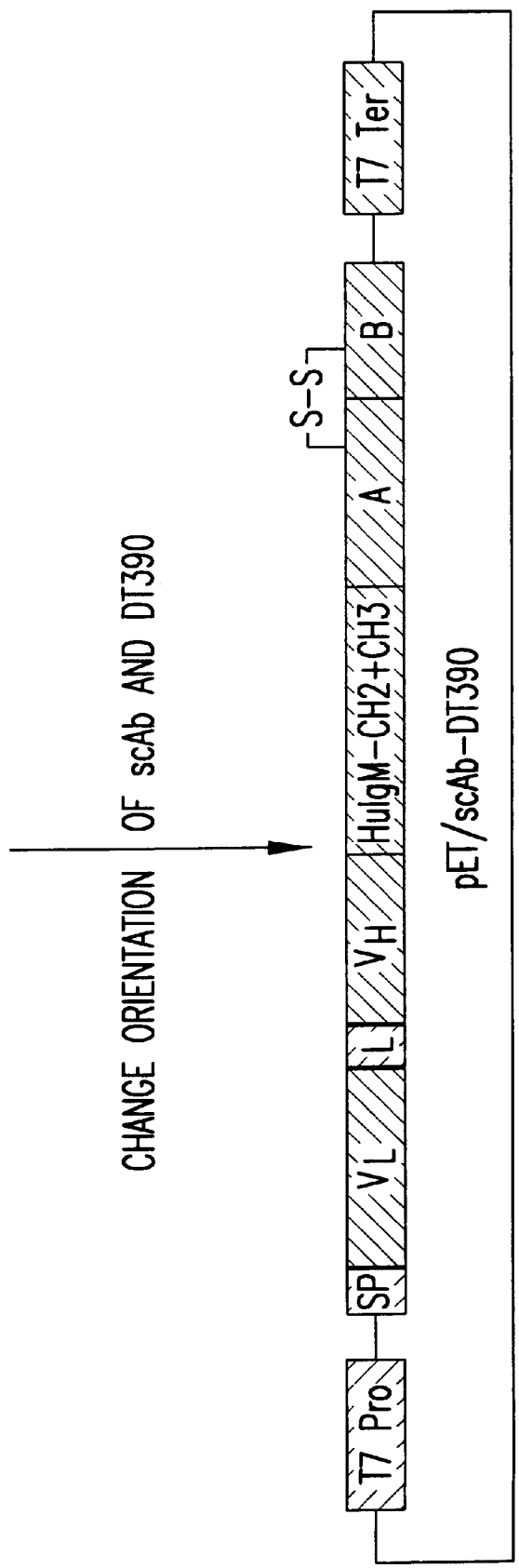
FIG. 12 shows another clone expressing a divalent immunotoxin fusion protein shown in FIG. 14.
Figure 13:
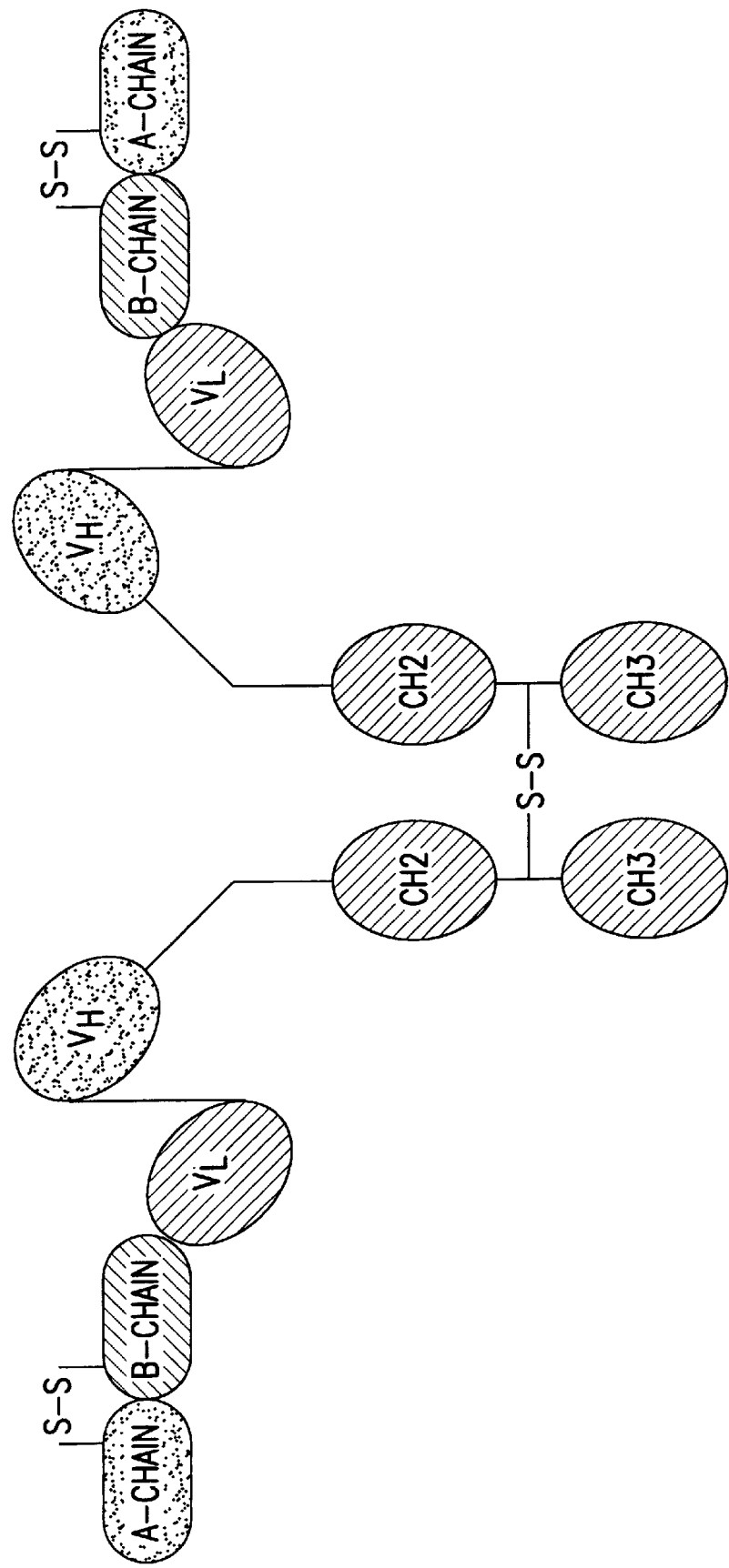
FIG. 13 is a schematic of a divalent fusion immunotoxin.
Figure 14:
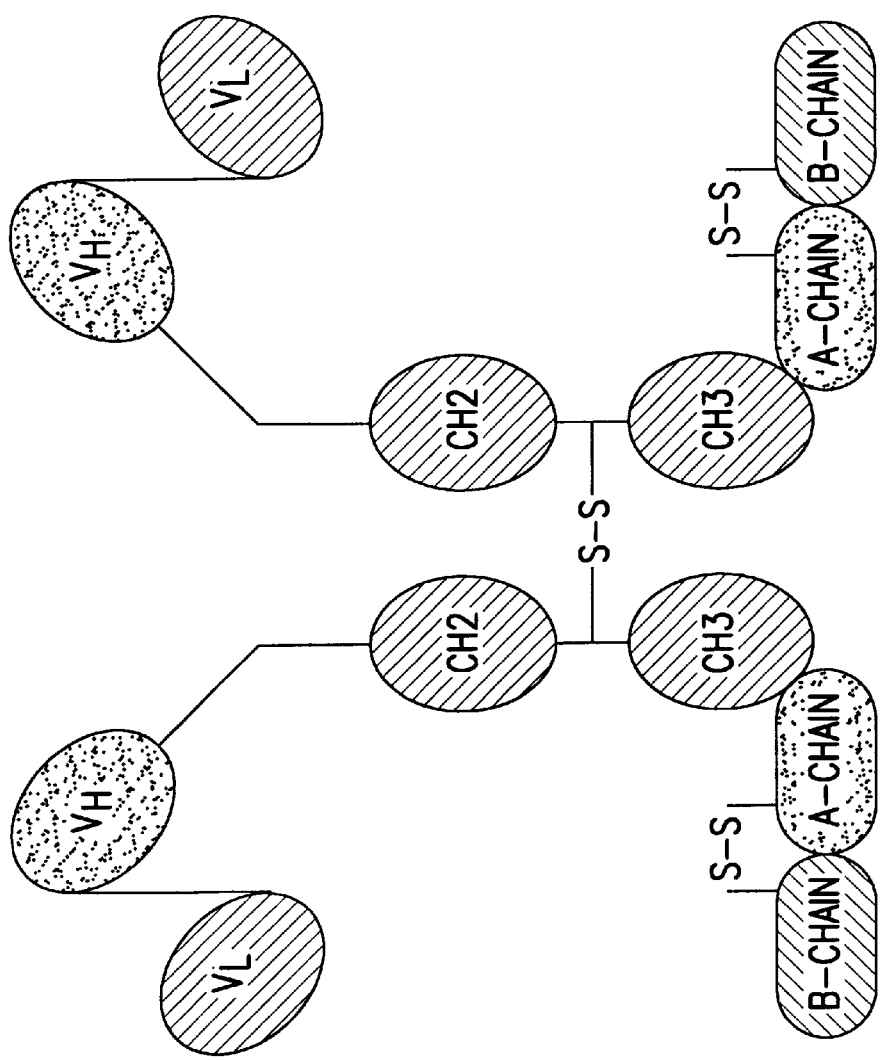
FIG. 14 is a schematic of a divalent fusion immunotoxin.
Figure 15:
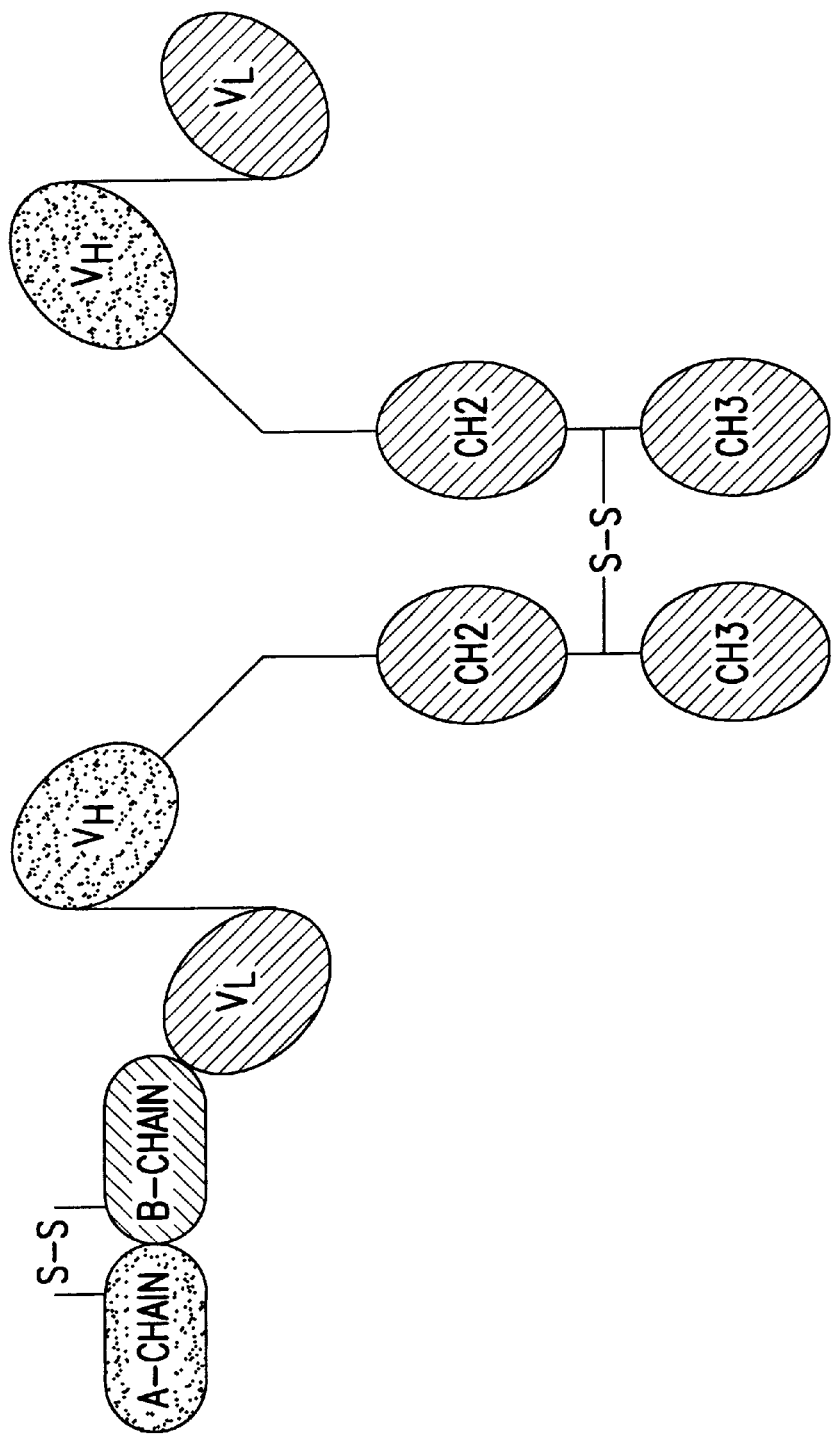
FIG. 15 is a schematic of a divalent fusion immunotoxin.

A variety of divalent fusion protein immunotoxins are provided. These have been expressed in *E. coli*, and Western blots of reduced and non-reduced SDS gels confirm that most of the immunotoxin is secreted as the dimeric (divalent) species (FIG. 9). The position of the toxin has been varied in an attempt to minimize stearic hindrance of the divalent antibody site, yet provide the best interactions with the CD3 receptor to facilitate toxin translocation across the membrane. FIG. 10 diagrams PCR amplification. FIGS. 11 and 12 show two different clones expressing divalent immunotoxin fusion proteins cartooned in FIGS. 13 and 14, respectively. Another variation is shown in FIG. 15. The clone producing this consists of a clone constructed by using the single chain antibody followed by a stop codon and the single chain immunotoxin, all under one promotor (Better et al. *Proc. Natl. Acad. Sci.* 90:457–461, January 1993). After secretion and oxidation of the interchain disulfide, 3 species are present: sc divalent antibody, divalent fusion immunotoxin, and a divalent sc antibody containing only one toxin. This species is isolated by size separation and is the species cartooned in FIG. 15. The advantage of this species is that stearic hindrance to the divalent antibody domains is limited by the presence of only one toxin domain. Other variations are routine to construct given the methods described herein and in the art. Those diagramed are considered to be the most likely to exhibit divalent character. Numerous orientations of toxin relative to antibody domains can be made and many are expected to be effective.

In addition, the length of the toxin C-terminus has been varied to provide optimization between two competing functions. The numbers after DT refer to the number of amino acid residues counting the amino terminus of the toxin A chain as 1. The full length toxin is called DTM1 and was provided by Dr. Richard Youle NINDS, NIH (Nicholls et al. *J. Biol. Chem.* 268(7):5302–5308, 1993). It has point mutations S to F at positions 508 and 525. This full length toxin mutant has the essential mutation of CRM9, S to F at 525 which reduces binding to the DT receptor by 3–4 logs without abolishing the translocation function. The other mutation S to F at 508 has been added because of previous restrictions on cloning mutant DT that can revert to wild type toxin with a minimum lethal dose of 0.1 microgram/kg by means of a single base pair reversion. Other mutations can be routinely made in the C terminus to perform this function (Shen et al. *J. Biol. Chem.* 269(46):29077–29084, 1994). They are: F530A; K526A; N524A; V523A; K516A Y514A. A clone having a single point mutation in DT reducing toxicity by 10–100 fold can be made providing that the clone contains an antibody fragment fusion protein, because chemical conjugation of antibody to DT has been shown to reduce systemic wild type toxin toxicity by 100 fold (Neville et al. *J. Biol. Chem.* 264(25):14653–14661, 1989). Therefore, the present invention provides a full length mutant DT sequence with the 525 S to F mutation alone as well as those listed above. These same mutations are also contemplated for the B chain mutant site in DTM2 and can be made similarly. Previous data with chemical conjugation has shown that the longer the C-terminus the better the translocation function (Colombatti et al. *J. Biol. Chem.* 261(7):3030–3035, 1986). However, the shorter the C-terminus the less effect of circulating anti-toxin blocking antibodies. Since patients have different levels of blocking antibodies which can be measured (see toxicity assay in), the optimal immunotoxin can be selected for individual patients. scUCHT1 fusion proteins with DTM1 and DT483 (see FIG. 16), DT390 (FIG. 17) and DT370 (FIG. 18) have been cloned and expressed in *E. coli*. Each of these variations as well as the divalent scUCHT1 fusion proteins using each of these toxin domains are provided.

The present invention provides an improvement on CRM197 (a non-toxic toxin mutant described in U.S. Ser. No. 08/034,509, filed Sep. 19, 1994) referred to herein as DTM2. DTM2 has the same mutation as CRM197 plus two mutations in the C-terminus which block binding (see sheet and FIG. 9). This is expected to reduce the likelihood of immune complex disease which could result when CRM197 becomes bound to cells and then is further bound by circulating antitoxin. Kidneys are particularly susceptible. DTM2 can not bind to cells thereby lessening the possibility of tissue damage. In addition DTM2 is made for high level production by including the pelB secretory signal for production in *E. coli* or a iron independent mutated promoter DT sequence cloned from CRM9 DNA for production in *C. diphtheriae*. The essential feature of DTM2 is the S to F mutation at 525 and the G to E mutation at 52, and a construct containing these two mutations is provided.

All of the constructs reported here can be expressed in *E. coli* using pelB signal sequences or other appropriate signal sequences. Expression can also be carried out in *C. diphtheriae* using appropriate shuttle vectors (Serwold-Davis et al. *FEMS Microbiol. Letters* 66:119–14, 1990) or in protease deficient strains of *B. subtilis* and using appropriate shuttle vectors (Wu et al. *Bio. Technol.* 11:71, January 1993).

EXAMPLE 12

Thymic Injection and Tolerance Induction in Primates

Without thymic treatment, rhesus monkey renal allografts reject at a mean of 7 days. Renal allografts in rhesus monkeys (age 2–5 years; 2–3 kg body weight) were performed. The experimental protocol consisted of first selecting MHC class I disparate rhesus monkey donors and recipients. Donor lymphocytes were injected into the recipient thymus gland 7 days prior to renal allografting from the same donor. Recipients received the immunotoxin of the present invention by intravenous injection. Renal allografts were performed and recipients underwent native nephrectomy.

Immunotoxin

Techniques for preparing anti-CD3-CRM9 (where the antibody is directed at the human T-cell receptor complex "CD3") have previously been described. See U.S. Pat. No. 5,167,956 and D. Neville et al., 89 P.N.A.S. USA 2585–2589 (1992). A hybridoma secreting UCHT1 was kindly provided by Dr. Peter Beverly, Imperial Cancer Research Fund, and was grown in ascites fluid and purified over immobilized Protein A. This is an IgGl.

FN18, also an IgGl, is the rhesus analog of UCHT1 and shares with it the property of being a T-cell mitogen in the presence of mixed mononuclear cells. FN18 was produced in hollow fiber and purified over Protein A. The strain of *C. diphtheriae* used for production of CRM9, C7 (βh tox-201 tox-9 h') was obtained from R. Holmes, Uniformed Services University of Health Sciences, Bethesda, Md. See also V. Hu et al., 902 Biochimicia et Biophysica Acta 24–30 (1987).

Antibody-CRM9 was recovered from the supernatant of 30 liter fermentation runs under careful control of iron concentration. See S. L. Welkos et al., 37 J. Virol. 936–945 (1981). CRM9 was purified by membrane concentration, ammonium sulfate precipitation and chromatography over DEAE. See S. Carroll et al., 165 Methods In Enzymology 68 (1988).

Large scale purification of immunotoxin was accomplished by HPLC size exclusion chromatography on MODcol (1266 Andes Blvd., St. Louis, Mo. 63132) "2×10" column packed with Zorbax (DuPont Company) GF-250 5 μm, 150 Å. Fractions containing 1:1 toxin:antibody mol ratios were isolated for these studies.

Immunotoxins were synthesized as previously described by thiolating both the monoclonal antibody moiety and the toxin moiety and then crosslinking with bismaleimidohexane. See D. Neville et al., 264 J. Biol. Chem. 14653–14661 (1989). CRM9 was nicked and the monomer (Carroll et al.) was isolated by the MODcol column described above prior to thiolation.

While CRM9 is a presently preferred mutant diphtheria toxin protein, other preferred embodiments include diphtheria mutants with a mutation in the DT binding region, such as DT390, should also be suitable (as the concept behind the immunotoxin is to replace the normal binding function with the antibody provided T-cell binding function, with minimal conformational change).

T-Cell Ablation

Monoclonal antibody FN18 (specific for rhesus monkey T lymphocytes) coupled to the immunotoxin CRM9 was used to deplete peripheral blood T-cells to levels below 200 cells/M13 in adult rhesus monkeys (measured six days after the injection). Some modest B cell depletion occurred. Following depletion, complete T-cell recovery takes about three to four weeks in a juvenile rhesus monkey model using this agent. Surprisingly, notwithstanding this fast recovery, donor T-cells injected into the thymus still were not impaired in their ability to produce tolerance.

Four monkeys received 0.2 mg/kg of immunotoxin, in three divided doses (24 hours apart from each other). Another monkey received 0.133 mg/kg immunotoxin in two divided doses (24 hours apart from each other), and the other monkey received 0.1 mg/kg in two divided doses (24 hours apart from each other). Two days after the last dose of immunotoxin, all monkeys except the last had at least 80% (actually greater than 99%) depletion of T cells both in the peripheral blood and in the lymph nodes. The lowest dose used in the last monkey reduced, but did not substantially eliminate either peripheral blood or lymph node lymphocytes.

Lymphocytes

Lymphocytes to be donated are preferably pooled from axillary and cervical lymph nodes of a single donor. The nodes are harvested, strained through a mesh to separate the lymphocytes, diluted with saline, and then injected. Alternatively, a representative “cocktail” of lymphocytes from several primates other than the donor, at least one of which turns out to be the same haplotype as the likely donor, should also work (if the donor is not available early enough).

Transplantation

Table 7 summarizes the outcome of renal transplants performed following thymic injection of donor lymph node lymphocytes (mixture of T and B cells) combined with immunotoxin therapy. Cells injected intrathymically consisted of the pooled axillary and inguinal lymph node lymphocytes in the numbers listed.

TABLE 7

Renal Allograft Survival by Treatment Group*

| Monkey | Intrathymic injection | FN18-CMR9 | Survival (days) |
|---|---|---|---|
| T4T | none | none | 5 |
| X9X | none | none | 7 |
| 1FE | none | none | 7 |
| H7C | 10.6 × 108 donor lymphocytes | none | 1 |
| W7C | 9.1 × 108 donor lymphocytes | none | 1 |
| 93023 | 7.0 × 108 donor lymphocytes | 0.2 mg/kg | >517 |
| 92108** | 1.9 × 108 donor lymphocytes | 0.2 mg/kg | 181 |
| POJ | 7.5 × 108 donor lymphocytes | 0.2 mg/kg | >340 |
| POF | normal saline | 0.2 mg/kg | >368 |
| PIP | normal saline | 0.2 mg/kg | >250 |
| W7D | none | 0.2 mg/kg | 51 |
| POG | none | 0.2 mg/kg | 84 |
| PIN | none | 0.2 mg/kg | >165 |
| X3J | none | 0.2 mg/kg | >117 |

*FN18-CRM9 was given on day -7, -6, -5 at a total dose of 0.2 mg/kg, i.v. Lymphocytes and saline were injected intrathymically on day -7.
**(acute rejection 40 days after skin graft)

Two monkeys died of pneumonia, one at 39 days and the other at 13 days. A third monkey died at 8 days of complications stemming from a urine leak. At autopsy, none of these three monkeys had any evidence of renal transplant rejection, either grossly or histologically.

Monkey #93023, which received the intrathymic injection and immunotoxin seven days prior to renal transplantation, had normal renal function more than 180 days post-transplant. A renal biopsy of his transplanted kidney at 100 days showed no evidence of rejection.

Surgical Procedures

Preferred surgical procedures include partial median sternotomy for exposure of the thymus and injection of donor lymphocytes into the thymus gland; inguinal and axillary lymphadenectomy to procure donor lymphocytes; laparotomy for procurement of the left kidney from kidney donors; and a second laparotomy for renal transplantation and native right nephrectomy. All of these procedures are performed under general anesthesia as outlined below. Serial blood draws are performed under ketamine and xylazine anesthesia as outlined below.

Thymic injection is performed through a midline chest incision beginning at the sternal notch extending down to the midportion of the sternum. The sternum is divided and retracted to expose the underlying thymus gland. The thymus gland is injected with donor lymphocytes and the sternum reapproximated and the soft tissue closed.

Donor nephrectomy is performed under general anesthesia through an upper midline incision in the abdomen. The retroperitoneal attachments of the left kidney are divided, the ureter is ligated and divided near the bladder, and the left renal artery and vein are dissected free. The left renal artery and vein are ligated adjacent to the aorta and inferior vena cava, and the kidney excised and flushed on the back table with preservation solution.

The recipient operation for renal transplantation is performed by making a midline abdominal incision under general anesthesia. The distal aorta and inferior vena cava are dissected free. The vena cava is clamped proximally and distally near its bifurcation and the donor renal vein anastomosed end-to-side to the recipient inferior vena cava using running 7-0 proline suture. The aorta is cross-clamped proximally and distally just proximal to its bifurcation and the donor renal artery anastomosed end-to-side to the aorta using running 8-0 proline. A ureteroneocystostomy is then performed by making an anterior cystotomy and anastomosing the spatulated tip of the donor ureter to the bladder mucosa using B-0 proline suture. The cystotomy is then closed. The abdomen is then closed.

Lymphadenectomy is performed through an approximately 2 cm groin incision for inguinal lymphadenectomy and a similar length incision for axillary lymphadenectomy. The lymph nodes are excised and bleeding points cauterized. The skin is then closed with running 4-0 nylon suture. It should be appreciated that kidney transplants are merely an example application. The invention should be suitable for use with a wide variety of organs (e.g. liver, heart, lung, pancreas, pancreatic islets and intestine).

In sum, surprisingly immunotoxins known to severely deplete T-lymphocytes will selectively deplete the host lymphocytes, without interfering with the donor T lymphocytes ability to cause tolerance. Further, the extreme level of depletion caused by this immunotoxin facilitates induction of tolerance.

EXAMPLE 13

Anti-CD3-CRM9 Immunotoxin Promotes Tolerance in Primate Renal Allografts

The ability of thymic injection and transient T lymphocyte depletion to permit development of donor-specific tolerance to rhesus monkey renal allografts was investigated. For T cell ablation, the immunotoxin FN18-CRM9, was used that depletes T cells from both the lymph node and blood compartments (see Example 5 and Neville et al. J Immunother 1996 (In press)). FN18-CRM9 is composed of an anti-rhesus monkey CD3 monoclonal antibody (mAb), FN18 (Neville et al., 1996), and a binding site mutant of diphtheria toxin, CRM9 (Neville et al. Proc Natl Acad Sci USA; 89: 2585–2589 (1992)). Compared to other anti-T cell agents used in clinical and experimental transplantation, FN18-CRM9 produces more effective killing of T cells, and this was the rationale for its choice as an agent to promote transplantation tolerance. Anti-CD3-CRM9 alone successfully delayed graft rejection. T cell depletion with anti-CD3-CRM9 combined with thymic injection prolonged graft survival to >150 days in five of five recipients and induced donor-specific tolerance in four of five recipients. Donor skin grafts were accepted long-term, whereas third party skin grafts were promptly rejected. These results are unique in their reliable induction of donor-specific tolerance as confirmed by skin grafting in a non-human primate model. This approach to tolerance reasonably correlates to induction of tolerance in humans.

MHC Typing and Donor-Recipient Selection

Donor-recipient pairs were selected based on maximizing MHC disparity. This was based on pre-transplant cytotoxic T lymphocyte (CTL) and mixed lymphocyte reaction (MLR) analysis (Derry H, Miller R G. Fathman C G, Fitch F W, eds. New York: Academic Press, 510 (1982) and Thomas et al. Transplantation, 57:101–115 (1994)), analysis of MHC class I differences by one-dimensional isoelectric focusing (1-D IEF) (Watkins et al. Eur J Immunol; 18:1425–1432 (1988)), and evaluation of MHC class II by PCR-based analysis.

Flow Cytometry

Two×$10^5$ lymphocytes obtained from peripheral blood or inguinal, axillary, or mesenteric lymph nodes were stained with FITC-labeled FN18 or isotype control antibody. Cells were subjected to flow cytometry on a Benton Dickenson FACSCAN.

Animals and Surgical Procedures

Outbred male juvenile rhesus monkeys (ages 1 to 3 years), virus free, were used as donors and recipients. Surgical procedures were performed under general anesthesia, using ketamine, 7 mg/kg, i.m., and xylazine, 6 mg/kg, i.m. induction, and inhalation with 1% halothane to maintain general anesthesia. Post-operatively, monkeys received butorphanol, 0.25 mg/kg, i.v., and aspirin, 181 mg, p.o., for pain control. Thymic injection was performed via a limited median sternotomy to expose the thymus gland. Seven days before renal transplantation, each lobe of the thymus was injected with donor lymphocytes suspended in 0.75 to 1.0 ml normal saline using a 27 gauge needle. Donor lymphocytes were procured from the inguinal, axillary, and mesenteric lymph nodes of the donor, counted and resuspended in normal saline for injection. Heterotopic renal transplants were performed using the donor left kidney. Following transplantation, the recipient underwent native nephrectomy. Graft function was monitored by measuring serum creatinine. Rejection was diagnosed by rise in serum creatinine to >0.07 mol/L, no evidence of technical problems, such as urine leak or obstruction at autopsy, and histologic confirmation. Monkeys were killed with a lethal dose of sodium pentobarbital if they rejected their kidney, and were autopsied. To test for tolerance, full thickness skin grafts were placed using ventral abdominal skin from donors placed onto the dorsal upper back of recipients. Grafts were evaluated daily by inspection.

Immunosuppression

FN18-CRM9 was chemically conjugated and purified as described (Neville et al. 1996). It was administered intravenously at a dose of 0.2 mg/kg in 3 divided daily doses starting 7 days prior to renal transplantation. No additional immunosuppressive drugs were given to any of the monkeys, and monkeys were not isolated from environmental pathogens.

Figure 19A:
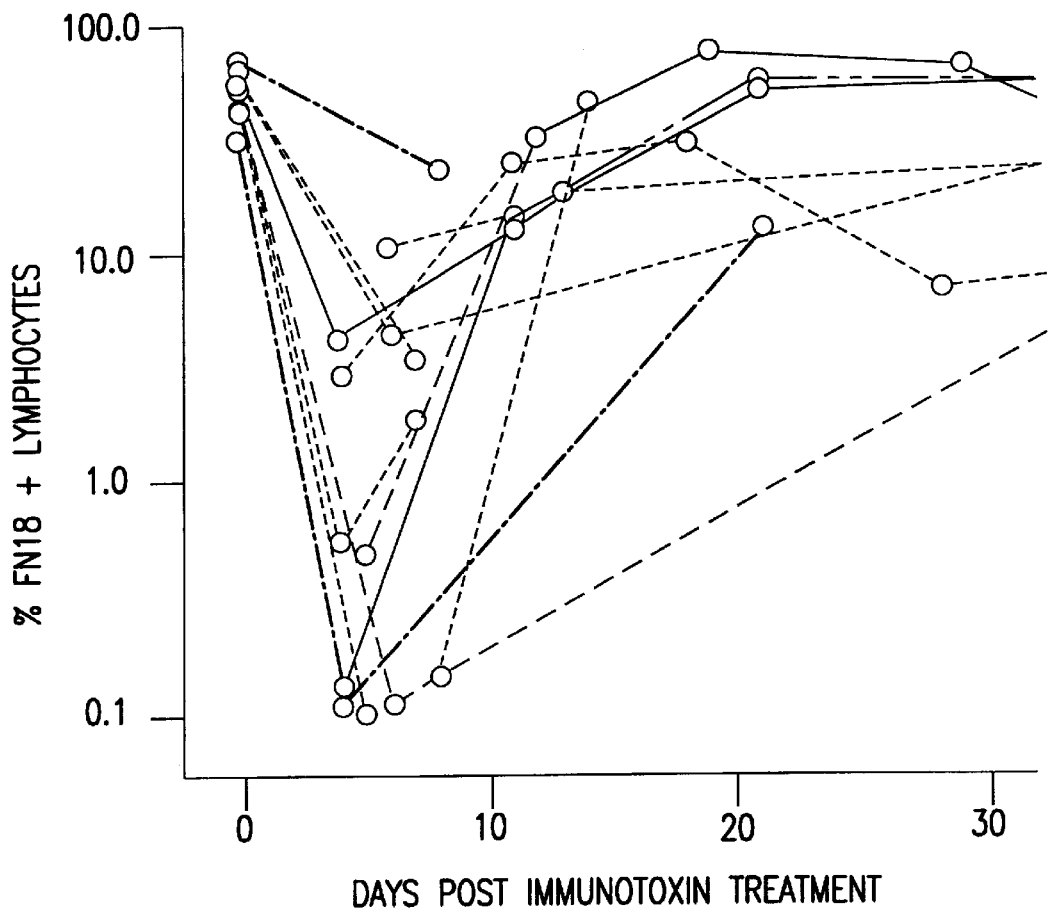
FIG. 19a shows CD3+ cell depletion and recovery in peripheral blood following immunotoxin treatment. Days refer to days after the first dose of immunotoxin.
Figure 19B:
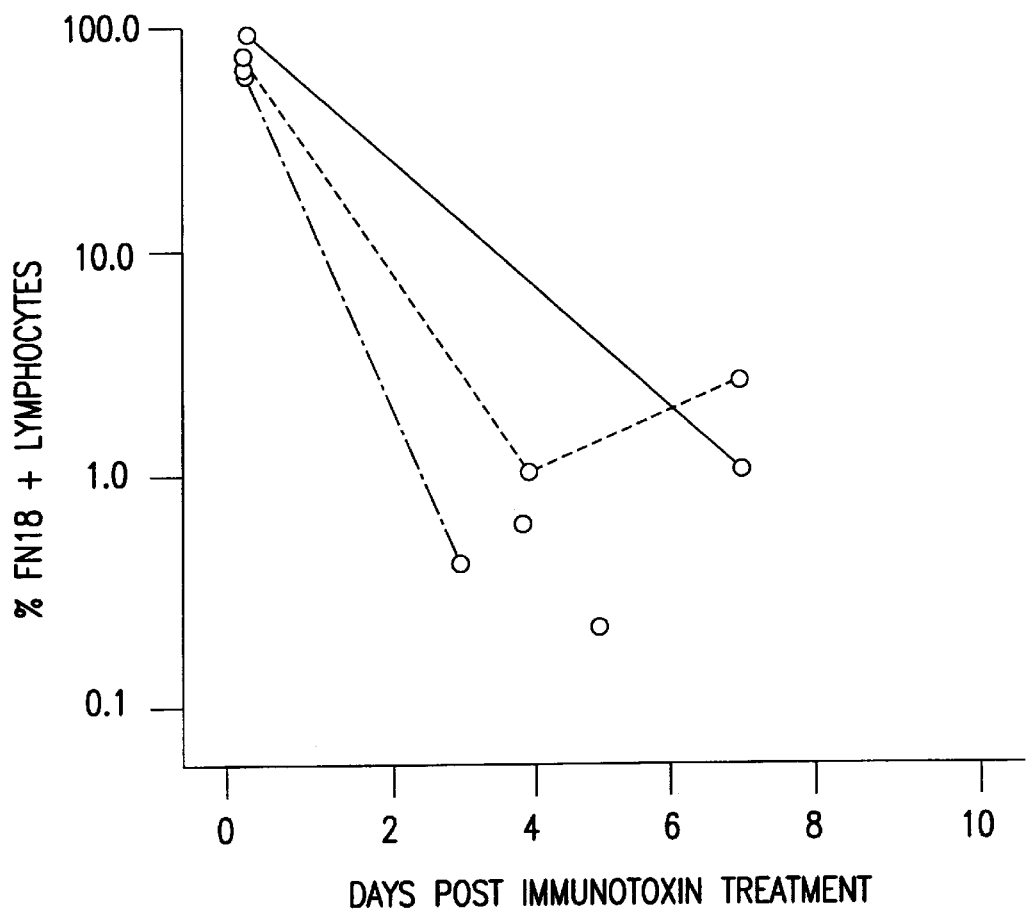
FIG. 19b shows CD3+ cell depletion in lymph nodes following immunotoxin treatment.

The effect of FN18-CRM9 on rhesus peripheral blood lymphocytes and lymph node lymphocytes is summarized in FIGS. 19a and 19b. In addition to causing transient T cell depletion from the peripheral blood, FN18-CRM9 depleted lymph node lymphocytes almost completely at the dose given and when measured 0–4 days after the third dose of drug. Absolute leukocyte counts did not change significantly with treatment. Recovery times were variable, but in general peripheral blood T lymphocytes returned toward baseline levels 2 to 4 weeks following treatment. Recovery rates varied between individual monkeys.

Untreated monkeys acutely rejected their allografts (n=3) within one week (Table 7). Monkeys receiving lymphocytes intrathymically but no anti-CD3-CRM9 developed hyperacute rejection within 24 hours (Table 7) with the typical histologic features of hemorrhage, infarction, and a dense neutrophil and lymphocyte infiltrate. Three of three recipients treated with donor lymphocytes intrathymically and anti-CD3-CRM9 had long-term graft survival (Table 7). One monkey (92108) rejected its kidney 40 days after a donor and third party skin graft were placed to test for donor-specific tolerance. This monkey rejected its third party skin graft at 10 days and a lymphocyte infiltrate in the donor skin graft developed with rejection of the renal allograft 40 days later. The other two recipients of donor lymphocytes and anti-CD3-CRM9 were successfully skin grafted from the donor with survival of these skin grafts for more than 100 days, but rejection of third party skin grafts at 10 days. All biopsies of their renal allografts showed an interstitial infiltrate but no evidence of glomerular or tubular infiltrates or injury. Two monkeys receiving normal saline injections in the thymus in combination with anti-CD3-CRM9 became tolerant of their renal allografts. Both of these monkeys rejected a third party skin graft at 10 days and have had long-term survival of donor skin grafts. The results of all skin grafts are summarized in Table 8. Renal biopsies of long-surviving tolerant recipients demonstrated focal interstitial mononuclear infiltrates without invasion or damage of tubules or glomeruli. Monkeys treated with anti-CD3-CRM9 alone developed late rejection in two cases at day 54 and day 88 and the histology of their kidneys at autopsy demonstrated a dense lymphocytic infiltrate. In two other cases, long-term unresponsiveness was observed (Table 7) to >127 days and >79 days. The thymuses of the two monkeys which rejected their grafts were markedly decreased in size at autopsy compared to age-matched controls prior to treatment, but a small thymic remnant was identified.

The data demonstrate that anti-CD3-CRM9 is a potent, new immunosuppressive agent which is capable of inducing tolerance in outbred MHC class I and class II disparate rhesus monkeys. This attribute distinguishes it from other currently known immunosuppressive agents, such as anti-thymocyte globulin, cyclosporine, or monoclonal antibodies which have more limited efficacy or safety in tolerance induction in large mammals or which require more cumbersome strategies (Powelson et al., Transplantation 57: 788–793 (1994) and Kawai et al., Transplantation 59: 256–262 (1995)). The degree of T cell depletion produced by 3 doses of the drug is more complete than that achieved by a longer course of anti-lymphocyte globulin, which generally depletes to a much lesser degree (Abouna et al., Transplantation 59: 1564–1568 (1995) and Bourdage J S, Hamlin D M, Transplantation 59:1194–1200 (1995)). Unlike OKT3, an activating antibody which does not necessarily kill T lymphocytes, anti-CD3-CRM9 is a lytic therapy with a more profound effect on T cells than OKT3 and better potential for tolerance induction. Its efficacy may be in part related to its ability to deplete T cells in the lymph node compartment, as well as in peripheral blood, since the majority of potentially alloreactive T cells reside in the lymph node compartments. The T cell depletion produced by anti-CD3-CRM9 is more complete than that achieved by any other known pharmacologic means, including total lymphoid irradiation, and it avoids the toxic side effects of radiation. Following treatment with the anti-CD3-CRM9, the thymus decreases markedly in size, although thymic cortex and medullary structures are still apparent. Anti-CD3-CRM9 appears to be safe and well tolerated in rhesus monkeys. No significant adverse drug effects were encountered. About half of the monkeys were treated with intravenous fluids for 3 to 5 days following administration to prevent dehydration. No infections were encountered in these experiments and only routine perioperative antibiotic prophylaxis was used at the time of renal transplantation and thymic injection. Cytokine release syndrome was not seen and monkeys did not develop febrile illness following drug administration.

The induction of tolerance in monkeys receiving thymic injection of either donor lymphocytes or normal saline in conjunction with anti-CD3-CRM9 suggests that thymic injection may provide an adjunct to tolerance induction using T cell depletion with anti-CD3-CRM9. Presumably, CD3+ lymphocytes present in the donor lymphocyte inoculum are also killed by the drug administered to the recipients. This would leave donor B cells to express donor MHC class I and class II in the recipient thymus. Rodent studies would suggest that it is the presence of one or both of these antigens that is crucial to promoting thymic tolerance (Goss J A, Nakafusa Y, Flye M W, Ann Surg 217: 492–499 (1993); Knechtle et al., Transplantation 57: 990–996 (1994) and Oluwole et al., Transplantation 56: 1523–1527 (1993)). Of even more interest is the observation that normal saline injected into the thymus in conjunction with anti-CD3-CRM9 produced tolerance in two of two recipients. Surprisingly, the success of this approach suggests that immunotoxin rather than thymic injection is crucial. Alternately, non-specific disruption of thymic integrity may contribute.

The observation that two of four recipients treated with anti-CD3-CRM9 alone became tolerant suggests that transient depletion of T cells by the drug is crucial in promoting tolerance. In rodents, transplant tolerance can be achieved by concomitant administration of donor antigen and anti-T-cell agents (Qin S et al., J Exp Med 169: 779–794 (1989); Mayumi H, Good R. A., J Exp Med 1989; 169: 213–238 (1989); and Wood M L et al., Transplantation 46: 449–451 (1988)), but this report demonstrates donor-specific tolerance using T cell specific therapy alone. The depletion of T cells from the lymph node compartment by anti-CD3-CRM9 may be crucial in promoting its efficacy as a tolerance inducing agent and differentiate it from anti-CD3 mAb alone which depletes the peripheral blood CD3 cells, but has a weaker effect on the lymphoid tissues (Hirsch et al., J Immunol 140: 3766–3772 (1988)).

These experiments using an outbred, MHC incompatible non-human primate model provide a rationale for tolerance strategies in human organ transplantation. The results are unique in offering a simple, reliable, and safe approach to tolerance in a model immunologically analogous to human solid organ transplantation. An anti-human CD3 immunotoxin (e.g., scUCHT1-DT390 and anti-CD3-CRM9) has been constructed and has T cell killing properties similar to FN18-CRM9 (see Neville 1992 and Neville 1996). The preliminary results reported here have broad implications for tolerance in humans.

In summary, immunotoxin treatment alone leads to marked prolongation of graft survival in 100% of the cases to date. Eliminating the thymic manipulation did not alter the success rate. No other drug or treatment regimen comes close to achieving these results in primates.

TABLE 8

Skin Graft Results

| Monkey | Interval after kidney transplant | 3rd party skin survival (days) | Donor skin survival (days) |
|---|---|---|---|
| 93023 | 182 | 10 | >367 |
| 92108 | 140 | 1040 | (and renal allograft rejection) |
| POF | 147 | 10 | >221 |
| POJ | 188 | 10 | >152 |
| PIP | 176 | 10 | >74 |

EXAMPLE 14

Immunotoxin Alone Induces Tolerance

Depletion of mature T cells can facilitate stable acceptance of MHC mismatched allografts, especially when combined with donor bone marrow infusion. Although ATG and anti-T cell mAbs eliminate recirculating cells, residual T cells in lymphoid tissue have potential to orchestrate immune recovery and rejection. Unlike pure antibodies, CD3-immunotoxin (CD3-IT) can destroy cells following direct binding and intracellular uptake without limitations of immune effector mechanisms. Thus, CD3-IT may have superior immunosuppressive activity. The action of CD3-IT in rhesus monkey kidney transplant recipients was examined.

The present example of CD3-IT is a conjugate of IgG1 mAb anti-rhesus CD3 epsilon (FN18) and a mutant diphtheria toxin CRM9 (FN18-CRM9). The B chain of CRM9 diphtheria toxin bears a mutation that markedly reduces binding to diphtheria toxin receptors, allowing specificity to be directed by anti-CD3.

CD3-IT was administered to 3–5 kg normal male rhesus monkey allograft recipients at a dose of 67 μg/kg on days −1 and 33 μg/kg on days +0 and +1 without additional immunosuppressive drugs. Recipient-donor combinations were selected to be incompatible by MLR and multiple DR allele mismatches; and all were seronegative for CRM9-reactive antibody to diphtheria toxin. Three groups received CD3-IT: (1) alone (n=3), (2) in combination with day 0 infusion of donor bone marrow DR−CD3− (n=3), (3) or with donor bone marrow and 200 cGy lymphoid irradiation given on days −1 and 0 (n=3).

Kidney allograft survival was remarkably prolonged. With CD3-IT alone, graft survival time was 57, 51, and 44 days. In combination with donor bone marrow infusion, graft survival was >400, 124, and 36 days. CD3-IT, lymphoid irradiation, and donor bone marrow resulted in graft survival of >300, 143, and 45 days. Both the 36 or 45 day graft losses were from hydronephrosis without evidence of rejection. Peripheral blood T cell counts fell selectively by 2 logs, and time to 50% recovery was 20–60 days. The peripheral blood CD3+CD4/CD8 ratio increased 2–6 fold before adjusting to baseline by 3 weeks. B cell/T cell ratios in lymph nodes were elevated >40-fold on day 5–7, reflecting a 1–2 log reduction in circulating and fixed tissue T cell compartments. LN CD4/CD8 ratios were normal at 5–7 days, but CD45RA+CD4 and CD28−CD4 cell subsets increased >1 log while CD28+CD8 cells decreased by >1 log, suggesting functional subset changes.

Anti-donor MLR responses became reduced uniformly, but specific unresponsiveness was seen only in the donor bone marrow-treated group. Peripheral blood microchimerism was detectable by allele specific PCR after donor bone marrow-infusion. These studies show CD3-IT to be an unusually effective and specific immunosuppressive agent in non-human primate transplantation and provides clinical tolerance induction strategies applicable to transplantation in humans.

EXAMPLE 15

Immunotoxin Plus Short Term Immunosuppressant Drugs Induces Tolerance in Monkeys in Models Simulating Human Cadaveric Donors The efficacy of IT in prolonging allograft survival was evaluated in a model that stimulates transplantation of organs from cadaveric donors in humans. Rhesus monkey donor-recipient pairs were selected on the basis of MHC class I and II disparity. Monkeys were given anti-CD3-CRM9 immunotoxin 0.2 mg/kg iv in three divided daily doses starting on the day of the renal allograft (group 1). In group 2, recipients also received methylprednisolone 125 mg iv daily for 3 days and mycophenolate mofetil 250 mg po daily for 3 days starting on the day of the transplant. Rejection was monitored by serum creatinine levels and confirmed histologically.

| Graft Survival (days) | | |
|---|---|---|
| Group 1 (IT alone) | Group 2 (IT + MMF + methylprednisolone) | Group 3 (untreated) |
| 79 | >90 | 5 |
| 57 | >75 | 7 |
| 51 | >60 | 7 |
| >124 | | |
| >102 | | |

The short burst of intensive anti-T cell therapy given at the time of the transplant appears to be well tolerated and to reliably result in long-term allograft survival. The mRNA cytokine profile of graft infiltrating cells obtained from renal transplant biopsies in this protocol suggests that IL-2 and γ-IF ($TH_1$ associated) are present in measurable levels and IL-4 and 10 ($TH_2$ associated) are detected at much lower levels. These results in a non-human primate model provide a strategy that can be applied to human organ transplant recipients who would benefit substantially from independence from maintenance immunosuppressive drugs.

A second group of rhesus monkeys undergoing mismatched renal transplantation received anti-CD3-CRM9 (IT) 18 hours pretransplant, 0.067 mg/kg and 0.033 mg/kg on days 0 and +1. Group 1 received only IT, n=6. Group 2, n=7, received in addition to IT deoxyspergualin (DSG) IV 2.5 mg/kg/day and solumedrol (SM), 7, 3.5 and 0.33 mg/kg IV during the IT administration. DSG was continued from 4 to up to 14 days. Plasma samples were tested by ELISA for cytokine release syndrome by measuring pre and post transplant plasma IL-12 and INF gamma levels.

| Graft Survival (days) | |
|---|---|
| Group 1 (IT alone) | Group 2 (IT + DSG + SM) |
| 10–57 n = 6 (rejections) | >155–200 n = 4 |
| | 28–45 n = 3 (rejections) |
| | 2 deaths from |
| | non-rejection causes |

Figure 20:
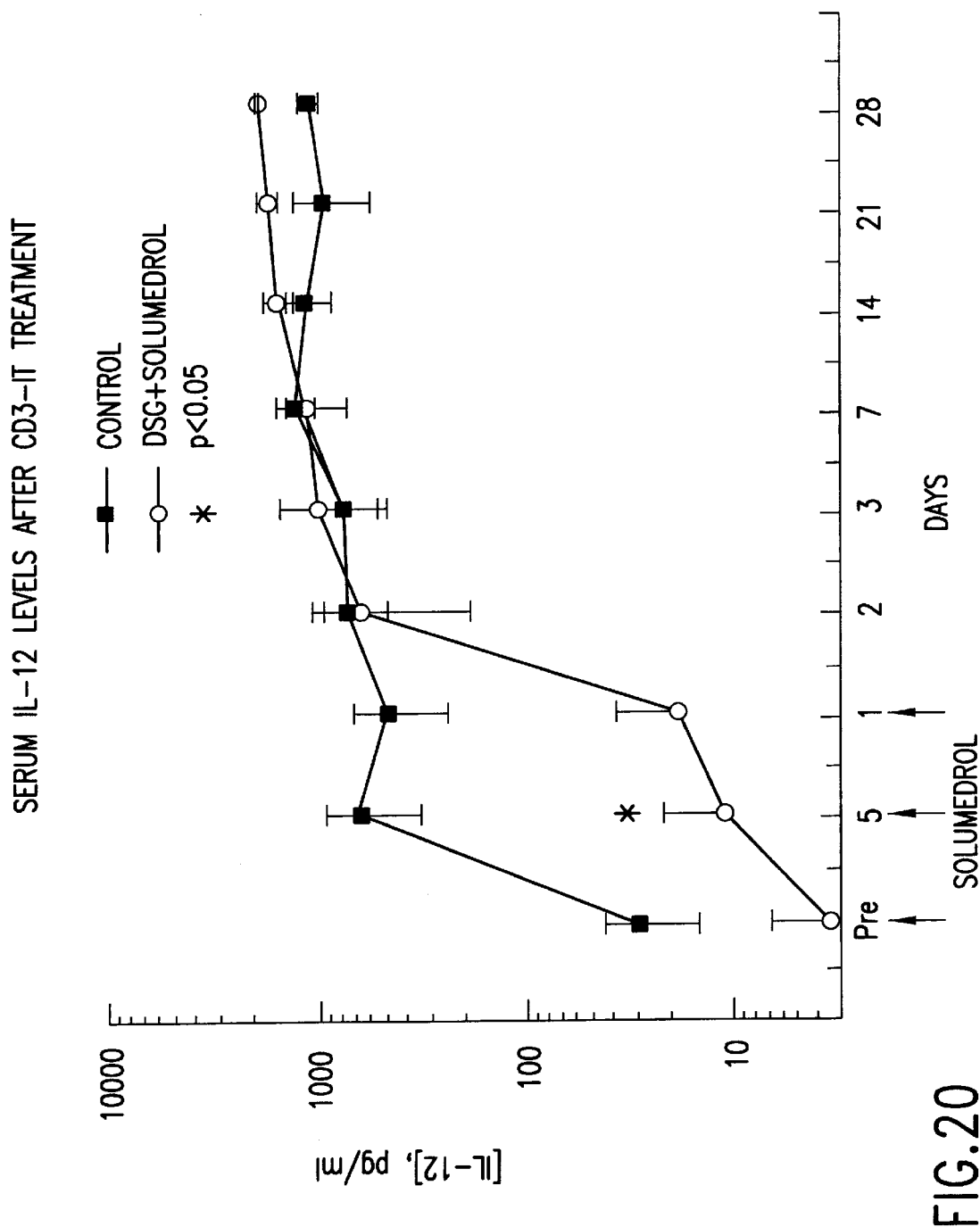
FIG. 20 shows the rise in serum IL-12 following FN18-CRM9 immunotoxin treatment in post kidney transplant monkeys with and without treatment with DSG (deoxyspergualin) and solumedrol.
Figure 21:
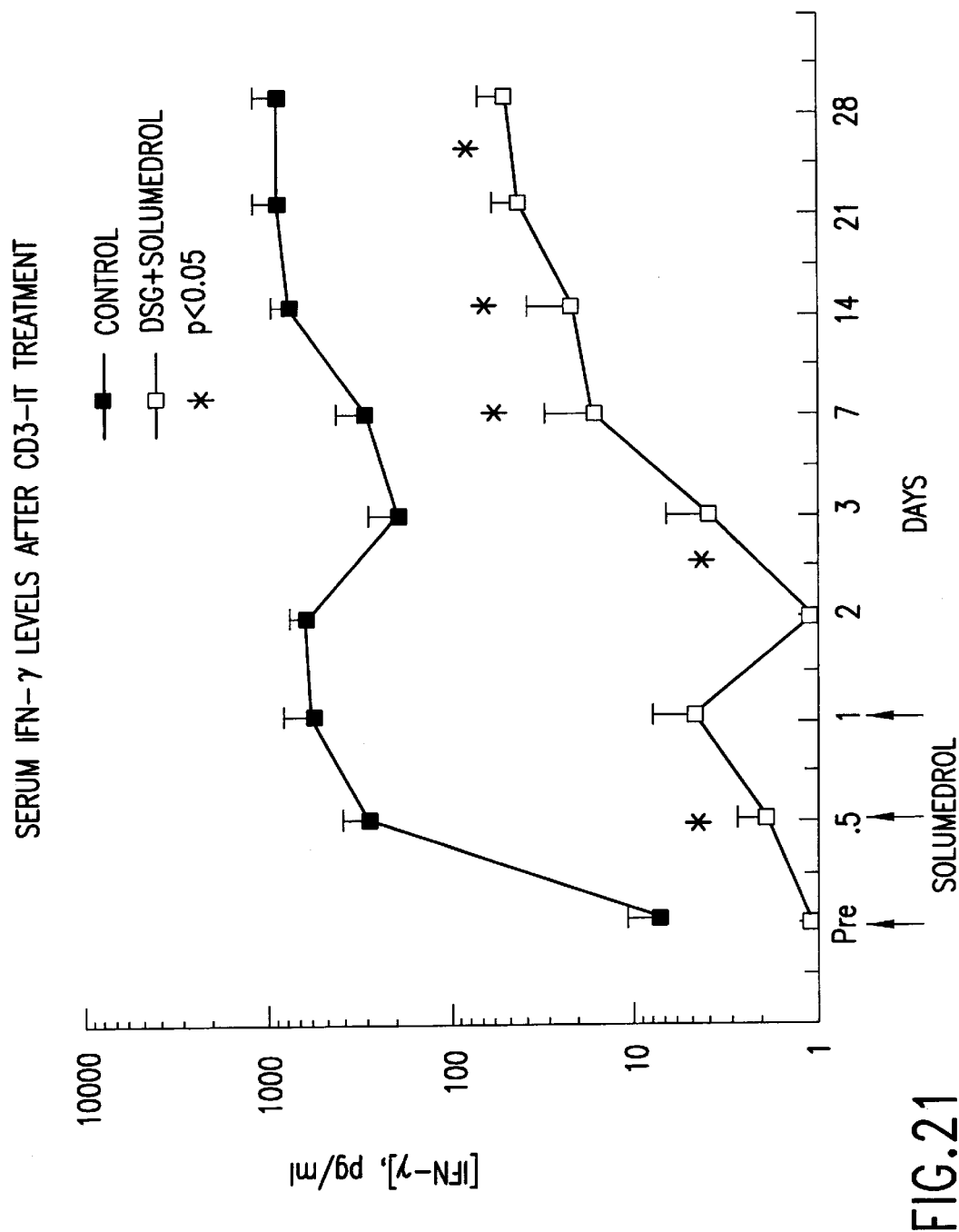
FIG. 21 shows the rise in serum IFN-gamma following FN18-CRM9 immunotoxin treatment in post kidney transplant monkeys with and without treatment with DSG and solumedrol. The treatment dramatically attenuates the rise of IFN-gamma.
Figure 22:
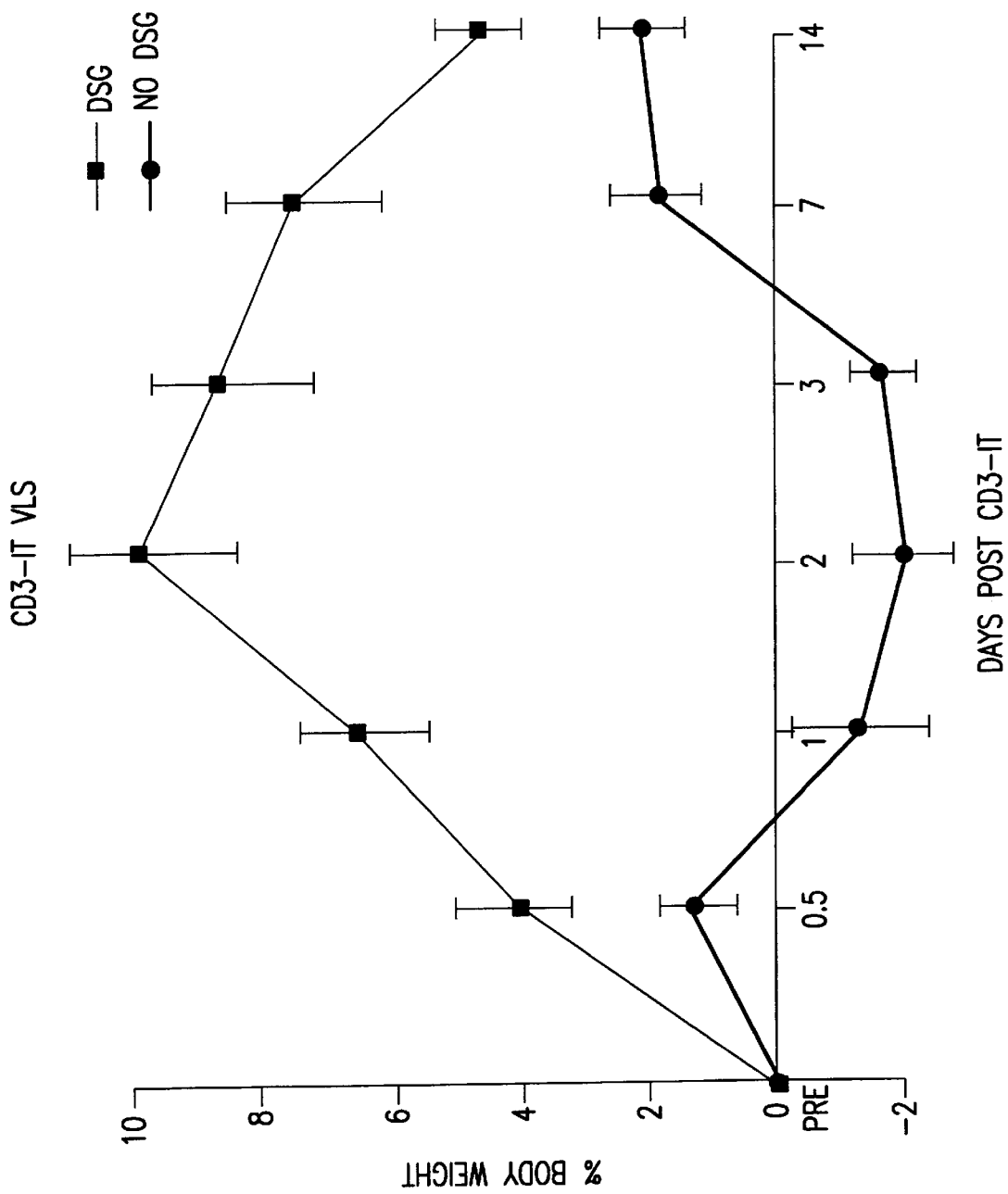
FIG. 22 shows that DSG and solumedrol treatment in the peritransplant period following immunotoxin suppresses weight gain, a sign of vascular leak syndrome related to IFN-gamma elevation.
Figure 23:
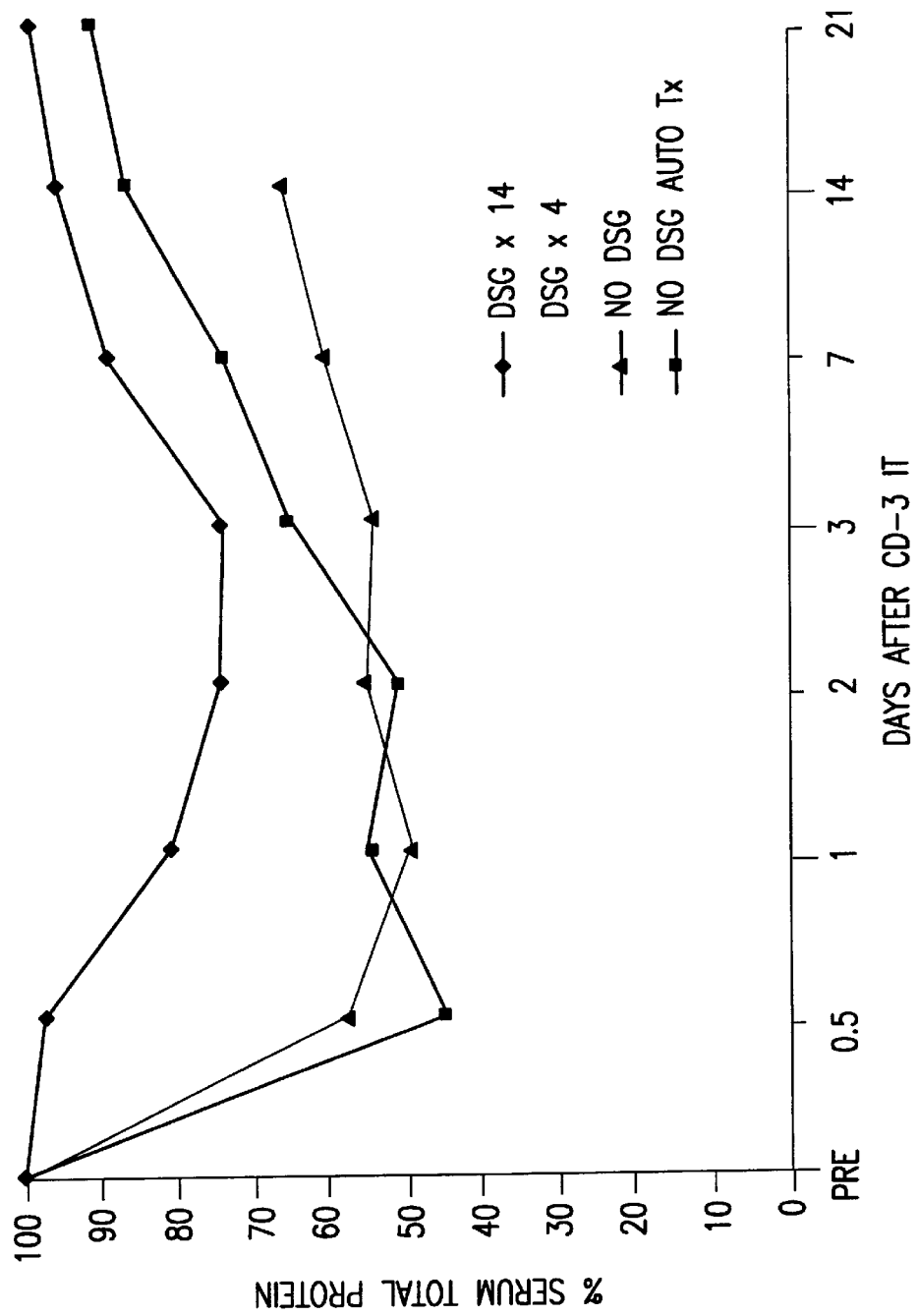
FIG. 23 shows that DSG and solumedrol treatment in the peritransplant period following immunotoxin suppresses hypoproteinemia, a sign of vascular leak syndrome related to IFN-gamma elevation.

IT, Group I, (or rhesus anti-CD3 an antibody alone) elevated both IL-12 and INF-8 gamma. DSG and solumedrol appear to block IL-12 induced activation of INF-gamma by a mechanism that may be associated with NF-kappa/beta (see FIGS. 20–21). This treatment is found to eliminate peritransplant weight gain (FIG. 22) and serum hypoproteinemia (FIG. 23), both signs of vascular leak syndrome, which in this study is associated with early graft rejection. This peritransplant treatment regimen can provide a rejection-free window for tolerance induction applicable to cadaveric transplantation.

It takes over 24 hours for IT to exert most of its lymph node T cell killing effects. Therefore, IT cadaveric transplantation protocols (protocols in which organ transplantation occurs generally within 6 hours of initial therapy and not longer than 18 hours) benefit substantially from peritransplant supplemental short term immunosuppressant agents to minimize peritransplant T cell responses to the new organ as shown by the above data.

Throughout this application various publications are referenced by numbers within parentheses. Full citations for these publications are as follows. Also, some publications mentioned hereinabove are hereby incorporated in their entirety by reference. The disclosures of these publications in their entireties are hereby incorporated by reference into this application in order to more fully describe the state of the art to which this invention pertains.

While the foregoing invention has been described in some detail for purposes of clarity and understanding, it will be appreciated by one skilled in the art from a reading of this disclosure that various changes in form and detail can be made without departing from the true scope of the invention and appended claims.

REFERENCES

1. Nicholls, P. J., Johnson, V. G., Andrew, S. M., Hoogenboom, H. R., Raus, J. C. and Youle, R. J. (1993) J Biol Chem 268, 5302–5308.
2. Neville, D. J. (1987) Ann N Y Acad Sci 507, 155–1643.
3. Williams, D. P., Parker, K., Bacha, P., Bishai, W., Borowski, M.,Genbauffe, F., Strom, T. B. and Murphy, J. R. (1987) Protein Eng 1,493–498
4. Johnson, V. G. and Youle, R. J. (1989) J Biol Chem 264, 17739–17744
5. Kreitman, R. J., Chaudhary, V. K., Waldmann, T. A., Hanchard, B., Cranston, B., FitzGerald, D. J. and Pastan, I. (1993) Leukemia 7, 553–562
6. Murphy, J. R. (1988) Cancer Treat Res 37, 123–124
7. Laske, D. W., Ilercil, O., Akbasak, A., Youle, R. J. and Oldfield, E. H. (1994) J Neurosurg 80, 520–526
8. Neville, D. J., Scharff, J. and Srinivasachar, K. (1992) J of Controlled Release 24, 133–141
9. Neville, D. J., Scharff, J. and Srinivasachar, K. (1992) Proc Natl Acad Sci USA 89, 2585–2589
10. Giannini, G., Rappuoli, R. and Ratti, G. (1984) Nucleic Acids Res 12, 4063–4069
11. Chang, T. M. and Neville, D. M. J. (1977) J Biol Chem 252, 1505–1514
12. Neville, D. J., Srinivasachar, K., Stone, R. and Scharff, J. (1989) J Biol Chem 264, 14653–14661
13. Shalaby, M. R., Shepard, H. M., Presta, L., Rodrigues, M. L., Beberley, P. C. L., Feldman, M. and Carter, P. (1992) J Exp Med 175, 217–225
14. Johnson, S. and Bird, R. E. (1991) in Methods in Enzymol, pp.88–98, Academic Press, Inc., San Diego, Calif.
15. Grimont, F. and Grimont, P. A. D. (1991) in Nucleic acid techniques in bacterial systematics, pp. 252, E. A. G. Stackebrandt M. John Wiley and Sons, LTD, West Sussex, England
16. Esworthy, R. S. and Neville, D. M. J. (1984) J Biol Chem 258, 11496–11504
17. Pelchen-Matthews, A., Armes, J. E., Griffiths, G. and Marsh, M. (1991) J Exp Med 173, 575–578
18. Choe, S., Bennett, M. J., Fujii, G., Curmi, P. M., Kantardjieff, K. A., Collier, R. J. and Eisenberg, D. (1992) Nature 357, 216–222
19. LeMaistre, C. F., Meneghetti, C., Rosenblum, M., Reuben, J., Parker, K., Shaw, J., Deisseroth, A., Woodworth, T. and Parkinson, D. R. (1992) Blood 79, 2547–2554
20. Platanias, L. C., Ratain, M. J., O'Brien, S., Larson, R. A., Vardiman, J. W., Shaw, J. P., Williams, S. F., Baron, J. M., Parker, K. and Woodworth, T. G. (1994) Leuk Lymphoma 14, 257–262
21. Higashi, K., Asada, H., Kurata, T., Ishikawa, K., Hayami, M., Spriatna, Y., Sutarman, Y. and Yamanishi, K. (1989) J Gen Virol 70,3171–3176
22. Youle, R. J. and Neville, D. M. J. (1982) J Biol Chem 257, 1598–1601
23. Williams, D. P., Snider, C. E., Strom, T. B. and Murphy, J. R.(1990) J Biol Chem 265, 11885–11889
24. Parlevliet et al. (1992) Transplant Int; 5:234–246.
25. Cosimi et al. (1981) Transplantation;32:535–9.
26. Jaffers et al. (1986) Transplantation;41:572–8.
27. Abramowicz et al. (1989) Transplantation; 47:606–8.
28. Burns et al. (1982) J Immunol;129:1451–7.
29. Parren et al. (1991) Res Immunol; 142:749–63.
30. Waid et al. (1991) Transplant Proc; 23:1062–5.
31. Khazaeli et al. (1994) J Immunotherapy; 15:42–52.
32. Chen C and Okayama H. (1987); Mol Cell Biol 7:2745–52.
33. Slavin-Chiorini et al. (1993) Int J Cancer ; 53:97–103.
34. Rigaut K D, Scharff J E, Neville D M Jr. (1995) Eur J Immunol;25:2077–82.
35. Woodle E S, Thistlethwaite J R, Jolliffe L K, et al. (1992) J Immunol;148:2756–63.
36. Miller A D, Rosman G J. (1989) BioTechniques 7:980–90.
37. Shu L M, Qi C F, Schlom J, Kashmiri SVS (1993) Proc Natl Acad Sci USA;90:7995–9.
38. Mosmann T R, Williamson A R (1980) Cell; 20:283–92.
39. Capon D J, Chamow S M, Mordenti J, et al. (1989) Nature 337:525–31.
40. Anand N N, Mandal S, MacKenzie C R, et al. (1991) J Bio Chem 266:21874–9.
41. Sitia R, Neuberger M, Alberini C M, et al. (1990) Cell;60:781–90.
42. Alberini C M, Bet P, Milstein C, Sitia R. (1990) Nature 347:485–7.
43. Fra A M, Fragioli C, Finazzi D, Sitia R, Alberini C M (1993) The EMBO Journal; 12:4755–61.
44. Wiersma E J, Shulman M J (1995); 154:5265–72.
45. Smith K G, Austyn J M, Hariri G, Beverley P C, Morris P J (1986) Eur J Immunol; 16:478–86.
46. Tax W J, Hermes F F, Willems R W, Capel P J, Koene R A (1984) J Immunol;133:1185–9.
47. Lynch, R G, Sandor M., Metzger H, ed. Washington DC: American Society for Microbiology 1990:305–34.
48. Moretta I, Webb S R, Grossi C E, Lydyard M, Cooper M D. (1977) J Exp Med;146:184–200.
49. Ferrarini M, Moretta L, Mingari M C, Tonda P, Pernis B. (1976) Eur J Immunol;6:520–1.
50. Mathur A, Lynch R G, Kohler G (1988);J Immunol; 140:143–7.
51. Pricop L, Rabinowich H, Morel P A, Sulica A, Whiteside T L, Herberman R B (1993) J Immunol; 151:3018–29.
52. Emara M, Sanfilippo F (1992) Cell Immunol; 144:143–54.

What is claimed is:

1. A method of inhibiting a rejection response in a primate recipient, by inducing immune tolerance in the primate recipient, to foreign mammalian donor cells, tissue or organ, comprising the steps of:
   a) exposing the recipient to an anti-CD3-DT immunotoxin with reduced anti-DT antibody binding so as to reduce the recipients T-cell lymphocyte population by at lest 80% in the presence or absence of anti-DT antibodies in the recipient; and
   b) transplanting the donor cells, tissue, or organ into the recipient, such that a rejection response by the recipient to the donor cell, tissue or organ is inhibited.

2. The method of claim 1, further comprising administering a corticosteroid.

3. The method of claim 2, further comprising administering an immunosuppressant compound to enhance the anti-T cell effects of the immunotoxin.

4. The method of claim 3, wherein the immunosuppressant compound is cyclosporin.

5. The method of claim 3, wherein the immunosuppressant compound is mycophenolate mofetil.

6. The method of claim 3, wherein the immunosuppressant compound is deoxyspergualin.

7. The method of claim 3, wherein the immunosuppressant compound blocks IL-12-induced induction of interferon-γ.

8. The method of claim 3, wherein the immunosuppressant is administered beginning from about 0 to 6 hours before the transplanting step.

* * * * *

UNITED STATES PATENT AND TRADEMARK OFFICE
CERTIFICATE OF CORRECTION

PATENT NO. : 6,103,235
DATED : August 15, 2000
INVENTOR(S) : David M. Neville; Stuart Knechtle It is certified that error appears in the above-indentified patent and that said Letters Patent is hereby corrected as shown below:

On the Title Page

Inventors:　　David M. Neville, Bethesda, Md.;
　　　　　　　Stuart Knechtle, Oregon, Wis.;
　　　　　　　Judith M. Thomas, Birmingham, Al.

Signed and Sealed this

Tenth Day of April, 2001

Attest:

NICHOLAS P. GODICI

*Attesting Officer*　　*Acting Director of the United States Patent and Trademark Office*